(12) United States Patent
Tsantrizos et al.

(10) Patent No.: US 11,279,719 B2
(45) Date of Patent: Mar. 22, 2022

(54) SUBSTITUTED BICYCLIC PYRIMIDINE-BASED COMPOUNDS AND COMPOSITIONS AND USES THEREOF

(71) Applicants: Youla S. Tsantrizos, Montreal (CA); Michael Sebag, Montreal (CA)

(72) Inventors: Youla S. Tsantrizos, Montreal (CA); Michael Sebag, Montreal (CA)

(73) Assignees: Youla S. Tsantrizos, Montreal (CA); Michael Sebag, Montreal (CA)

( * ) Notice: Subject to any disclaimer, the term of this patent is extended or adjusted under 35 U.S.C. 154(b) by 156 days.

(21) Appl. No.: 16/509,595

(22) Filed: Jul. 12, 2019

(65) Prior Publication Data
US 2019/0367542 A1 Dec. 5, 2019

Related U.S. Application Data

(63) Continuation of application No. PCT/CA2018/050091, filed on Jan. 26, 2018.
(60) Provisional application No. 62/528,601, filed on Jul. 5, 2017, provisional application No. 62/450,736, filed on Jan. 26, 2017.

(51) Int. Cl.
*C07F 9/38* (2006.01)
*A61P 35/00* (2006.01)
(52) U.S. Cl.
CPC ............ *C07F 9/3886* (2013.01); *A61P 35/00* (2018.01)
(58) Field of Classification Search
CPC ............................... C07F 9/3886; A61P 35/00
USPC ......................................................... 514/108
See application file for complete search history.

(56) References Cited

U.S. PATENT DOCUMENTS 9,745,331 B2   8/2017   Wiemer

FOREIGN PATENT DOCUMENTS

| EP | 2826781 A1 | 1/2015 |
|---|---|---|
| WO | 2008/073785 A2 | 6/2008 |
| WO | 2009/013545 A2 | 1/2009 |
| WO | 2010/045006 A1 | 4/2010 |
| WO | 2011/050211 A2 | 4/2011 |
| WO | 2014/008407 A1 | 1/2014 |
| WO | 2014/078957 A1 | 5/2014 |
| WO | 2014/176546 A1 | 10/2014 |
| WO | 2016/018697 A1 | 2/2016 |
| WO | 2016/081281 A1 | 5/2016 |

OTHER PUBLICATIONS

International Search Report and Written Opinion of corresponding International Application No. PCT/CA2018/050091 dated May 11, 2018, 12 pages.

Extended European Search Report of corresponding EP Appln. No. 18744659.6 dated Sep. 21, 2020, 5 pgs.
Leung et al., Thienopyrimidine Bisphosphonate (ThPBP) Inhibitors of the Human Farnesyl Pyrophosphate Synthase: Optimization and Characterization of the Mode of Inhibition, Journal of Medicinal Chemistry, 2013, vol. 56, pp. 7939-7950.
Leung, et al, Discovery of thienopyrimidine-based inhibitors of the human farnesyl pyrophosphate synthase—Parallel synthesis of analogs via a trimethylsilyl ylidene intermediate, Bioorg. Med. Chem. 2013, 21, pp. 2229-2240.
De Schutter et al., Multistage screening reveals chameleon ligands of the human farnesyl pyrophosphate synthase: implications to drug discovery for neurodegenerative diseases, Journal of Medicinal Chemistry, Jun. 23, 2014, vol. 57(13), pp. 5764-5776.
Gao, et. al., [11C]olanzapine, radiosynthesis and lipophilicity of a new potential PET 5-HT2 and D2 receptor radioligand., Bioorg. Med. Chem. Lett., 2013, vol. 23(7), pp. 1953-1956.
Chen, et. al., Microwave-Assisted Synthesis of 4-Amino-2-arylthieno[2,3-d]pyrimidines and Their Subsequent Functionalization, Synthesis, 2010, vol. 14, pp. 2413-2418.
Liebeskind et al., Heteroaromatic thioether-boronic acid cross-coupling under neutral reaction conditions, Org. Lett., 2002, vol. 4(6), pp. 979-981.
Roecker et al., Discovery of dual orexin receptor antagonists with rat sleep efficacy enabled by expansion of the acetonitrile-assisted/diphosgenemediated 2,4-dichloropyrimidine synthesis, Biorg. Med. Chem. Lett., 2014, vol. 24, pp. 2079-2085.
Shu, L. et al., Convenient Synthesis of 5,7-Dichlorothiazolo[5,4-d]pyrimidine, Heterocycles, 2012, vol. 85, pp. 1721-1726.
Zeng, Q. et al., Facile and Practical Synthesis of 2,6-Dichloropurine, Org. Proc. Res. Dev., 2004, vol. 8, pp. 962-963.
Hatcher, J. M. et al., Discovery of a Pyrrolopyrimidine (JH-II-127), a Highly Potent, Selective, and Brain Penetrant LRRK2 Inhibitor, ACS Med. Chem. Lett. 2015, 6, 584-589.

(Continued)

*Primary Examiner* — Kristin A Vajda
(74) *Attorney, Agent, or Firm* — Bereskin & Parr LLP/S.E.N.C.R.L., s.r.l.; Patricia Folkins

(57) ABSTRACT

Novel C-2-substituted bicyclic compounds of Formula I have been prepared and found to be useful as inhibitors of by inhibiting geranylgeranylation of proteins.

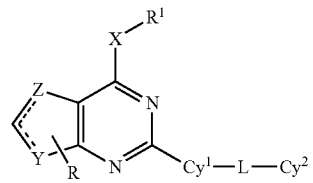

Formula I

The application is directed to these compounds, to compositions comprising these compounds and to their use, in particular as medicaments to cancer and other conditions treatable by inhibiting human geranylgeranylation pyrophosphate hGGPPS activity.

19 Claims, 11 Drawing Sheets

(56) References Cited

OTHER PUBLICATIONS

Lin et. al., Design and Synthesis of Active Site Inhibitors of the Human Farnesyl Pyrophosphate Synthase: Apoptosis and Inhibition of ERK Phosphorylation in Multiple Myeloma Cells, J. Med. Chem., 2012, 55, 3201-3215.

Park, J. et al., Human Isoprenoid, Synthase Enzymes as Therapeutic Targets, Frontiers in Chemistry 2014, 2, Article 50, pp. 1-21.

Szabo et. al., Inhibition of Geranylgeranyl Diphosphate Synthase by Bisphosphonates and Diphosphates: A Potential Route to New Bone Antiresorption and Antiparasitic Agents, J. Med. Chem. 2002, 45, 2185-2196.

Elliott, T.S. et al., The use of phosphate bioisosteres in medicinal chemistry and chemical biology, Chem. Med. Comm. 2012, vol. 3, pp. 735-751, Abstract.

Gritzalis et al., Probing the molecular and structural elements of ligands binding to the active site versus an allosteric pocket of the human farnesyl pyrophosphate synthase, Bioorg Med Chem Lett, 2015, vol. 25(5), pp. 1117-1123.

Matralis et al., Synthesis of Benzothiophene—Containing 10- and 11-Membered Cyclic Phostones, Eur. J. Org. Chem., 2016, pp. 3728-3736.

Lacbay, Unraveling the Prenylation—Cancer Paradox in Multiple Myeloma with Novel Geranylgeranyl Pyrophosphate Synthase (GGPPS) Inhibitors, J. Med. Chem., 2018, vol. 61(15), pp. 6904-6917.

Hahn et al., A Phase I Trial of the Farnesyltransferase Inhibitor L-778,123 and Radiotherapy for Locally Advanced Lung and Head and Neck Cancer, Clinical Cancer Research, vol. 8, May 2002, pp. 1065-1072.

Martin et al., A Phase I Trial of the Dual Farnesyltransferase and Geranylgeranyltransferase Inhibitor L-778,123 and Radiotherapy for Locally Advanced Pancreatic Cancer, Clinical Cancer Research, Aug. 15, 2004, vol. 10, pp. 5447-5454.

Lobell et al., Evaluation of Farnesyl: Protein Transferase and Geranylgeranyl: Protein Transferase Inhibitor Combinations in Preclinical Models, Cancer Research, Dec. 15, 2001, pp. 8758-8768.

Park et al, Pharmacophore Mapping of Thienopyrimidine-Based Monophosphonate (ThP-MP) Inhibitors of the Human Farnesyl Pyrophosphate Synthase, J. Med. Chem., 2017, vol. 60, pp. 2119-2134, Abstract.

Office Action issued in corresponding Japanese Pat. Appln. No. 2019-540325 dated Sep. 9, 2021, English translation, 4 pages.

Chen, S-H., et al. "Moiety-Linkage Map Reveals Selective Nonbisphosphonate Inhibitors of Human Geranylgeranyl Diphosphate Synthase", Journal of Chemical Information and Modeling, 2013, vol. 53, pp. 2299-2311.

(a)

(b)

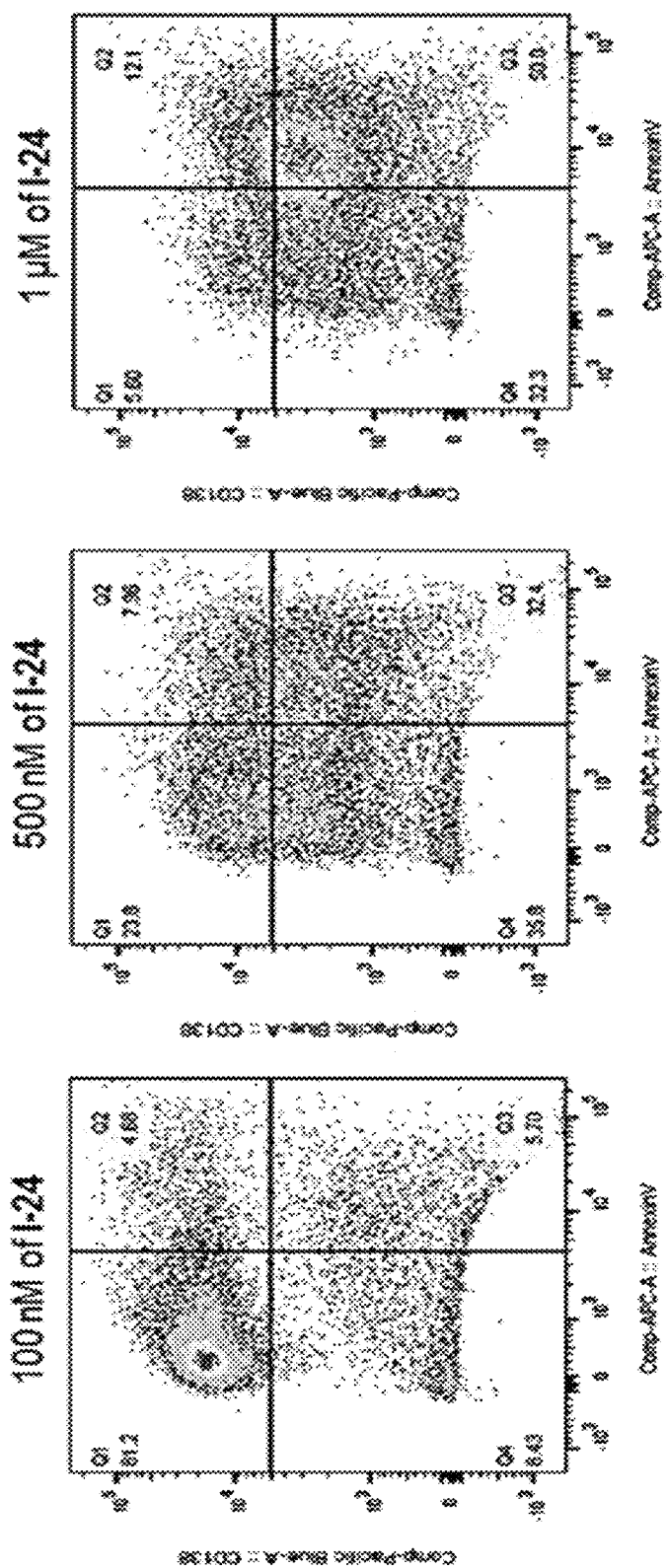

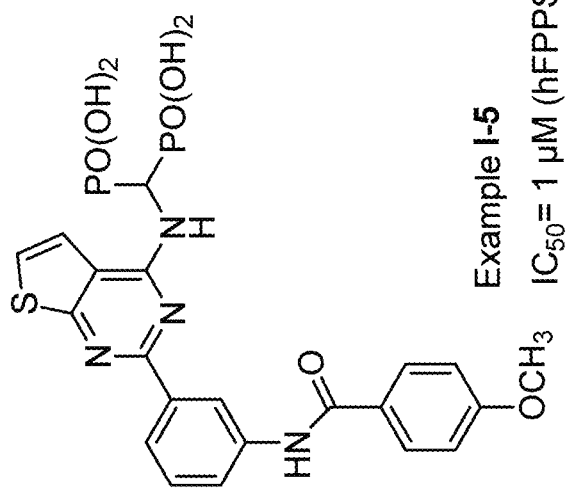
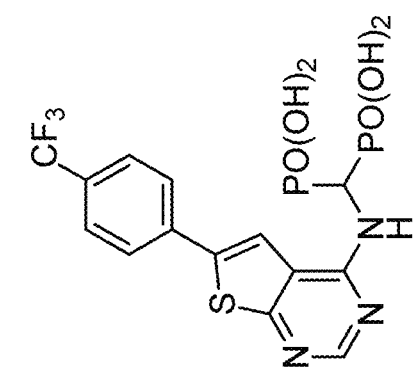
FIG. 7

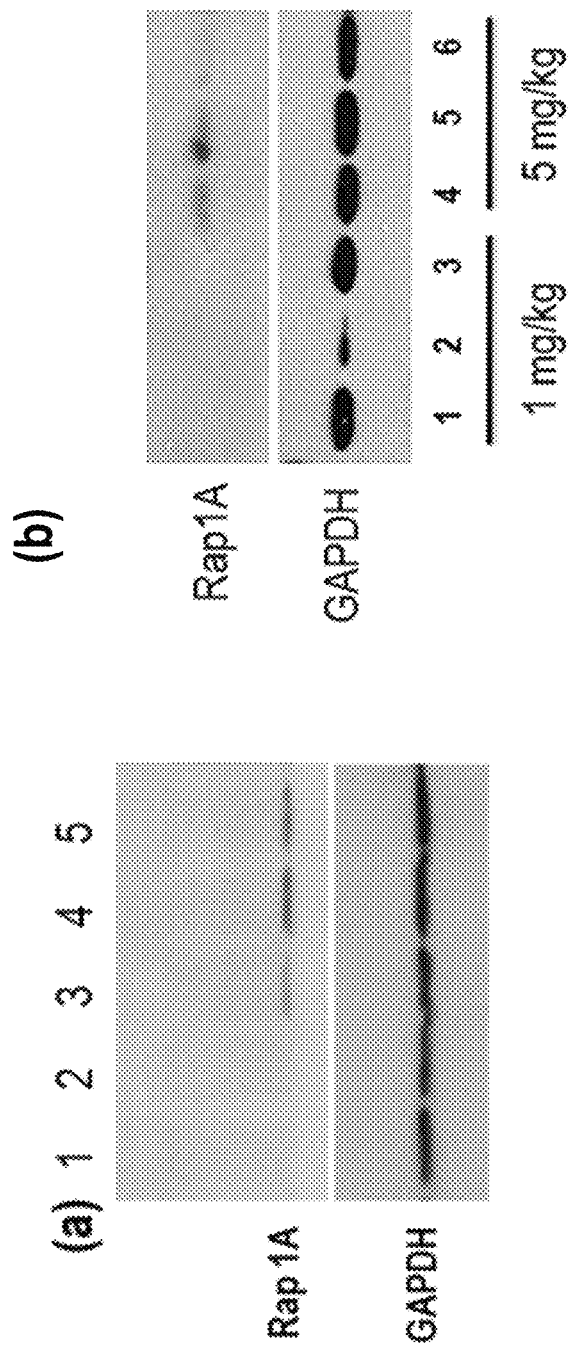

SUBSTITUTED BICYCLIC PYRIMIDINE-BASED COMPOUNDS AND COMPOSITIONS AND USES THEREOF

RELATED APPLICATIONS

This application is a continuation of co-pending International Application No. PCT/CA2018/050091, filed on Jan. 26, 2018, which claims the benefit of priority of U.S. Provisional Patent Application No. 62/528,601 filed Jul. 5, 2017, and U.S. Provisional Patent Application No. 62/450,736 filed Jan. 26, 2017 the contents of each of which are incorporated herein by reference in their entirety.

FIELD

The present application relates to novel bicyclic heterocyclic compounds, to processes for their preparation, to compositions comprising them, and to their use, for example in therapy. More particularly, the application relates to compounds useful in the treatment of diseases, disorders or conditions that are mediated by high levels of the isoprenoid metabolites, particularly, the metabolite geranylgeranyl pyrophosphate (GGPPS).

BACKGROUND

Post-translational modifications of small GTPases with farnesyl pyrophosphate (FPP; C15 isoprenoid) or geranylgeranylation pyrophosphate (GGPP; C20 isoprenoid) is commonly known as protein prenylation. Prenylation provides GTPases with the ability to associate specifically with cellular membranes which have a high concentration of signalling biomolecules and consequently, participate in a plethora of cellular functions, including cell signalings proliferation, and synaptic plasticity (FIG. 1a,b); for a recent review refer to Wang, M.; Casey, P. J. *Nature Rev./Mol. Cell Biol.* 2016, 77, 110-122.

In the past, inhibition of protein prenylation focused mainly on blocking RAS activation, especially mutated K-RAS, which is a common driver of oncogenesis, by inhibiting the transferase enzyme FTase that catalyses the attachment of FPP to the GTPases, including K-Ras, H-RAS and N-Ras proteins. However, a biochemical redundancy mechanism allows K-Ras activation by GGPP prenylation, which is catalyzed by the transferase enzyme GGTPase I; consequently, GGTPase I takes over the task of Ras prenylation, when FTase is inhibited (FIG. 1; Rowinsky, E. K. *J. Clin. Oncol.* 2006, 24, 2981-2984). It was then suspected that there are several mechanisms leading to the escape of FTase inhibition (in addition to the alternative prenylation by GGTPase I), consequently attention was re-directed to targeting GGTase I. For example, a genetics study showed that conditional deletion of the gene encoding a β-subunit of GGTase I in myeloid and lung cells, almost completely eliminated the proliferation and tumour formation that accompanies induction of K-Ras expression, leading to markedly improved survival of mice (Sjogren, A.-K. M. et al. *J. Clin. Invest.* 2007, 117, 1294-1304). This study suggested that inhibition of GGPP prenylation may be a useful strategy to treat K-Ras-induced malignancies, in addition to other human diseases that are driven by GGPP prenylation of small GTP binding proteins (commonly referred to as GTPases), such as RhoA, RhoB, RhoC, Rac1, cdc-42, R-Ras and Rap1A (Kho, Y. et al. *Proc. Natl. Acad Sci. USA* 2004, 101, 12479-12484).

Current biochemical evidence from Applicant's own research (Pelleieux, S. et al. Isoprenoids and tau pathology in sporadic Alzheimer's disease. *Neurobiology of Aging* 2018, in press) and other researcher groups [examples include (a) Eckert, G. P. et al. *Neurobiol. Disease* 2009, 35, 252; (b) Hooff, G. P. et al. *Biochim. Biophys. Acta* 2010, 1801, 896;] also suggests that high intracellular levels of isoprenoids in the brain of Alzheimer's patients is potentially involved in the accumulation of phosphorylated tau (P-Tau) protein and neuronal damage (FIG. 1b). P-Tau is the hallmark of neurofibrillary tangle formation in the brain and strongly implicated in the progression of Alzheimer's disease (He, Z. et al. *Nature Medicine* 2018, 24, 29-38).

The prenylation cascade from FPP→GGPP→RhoA-cdc42→GSK3-β→phospho-Tau (FIG. 1b) has been proposed as largely responsible for Alzheimer's-associated tau phosphorylation and tangle formation of neurons. Therefore, inhibitors of hGGPPS may be valuable therapeutics for arresting the progression of Alzheimer's disease or delaying its onset in pre-symptomatic subjects.

The human enzymes fanesyl pyrophosphate synthase (hFPPS) and human geranylgeranyl pyrophosphate synthase (hGGPPS) control strategic steps in the mevalonate pathway (FIGS. 1a and 1b) and are functionally very similar in that, during their catalytic cycle, they both bind a pyrophosphate-based substrate (DMAPP, GPP or FPP) and extend its hydrocarbon side chain via the addition of an IPP unit (FIG. 1a). Consequently, non-selective inhibition of both enzymes by compounds that are pyrophosphate mimics (e.g. bioisosteres) has been observed. In the past, drug discovery efforts was based on the presumption that selectivity in inhibiting hGGPPS over hFPPS is of little therapeutic value, since inhibition of hFPPS will inevitably lead to intracellular depletion of the required substrate for hGGPPS, thus indirectly decreasing the intracellular levels of the GGPP metabolite (FIG. 1).

Numerous nitrogen-containing bisphosphonate (A-BP) compounds that selectively inhibit hFPPS have been reported in the literature, including zoledronic acid (ZOL), a clinically useful drug for the treatment of bone diseases, such as osteoporosis and lytic bone diseases due to cancer (Melton, L. J., 3rd et al. *J Bone Miner Res* 2005, 20, 487-493). Interestingly, there is an on-going debate in the scientific and medical communities as to whether (or not) A-BP drugs that selectively inhibit hFPPS, such as ZOL, are bona fide antitumor agents. Clinical trials with breast cancer (Coleman, R. E. et al. *New Engl. J. Med.* 365, 1396-1405) and multiple myeloma (MM) patients [(a) Morgan, G. J. et al. *Lancet* 376, 1989-1999; (b) Morgan, G. J. et al. *Blood* 119, 5374-5383] treated with standard chemotherapy plus ZOL indicated improved disease-free survival, although the effects were limited. Additionally, statins that block the mevalonate pathway at the initial HMG-CoA level (FIG. 1b) were reported to reduce mortality in MM patients [(a) Mullen, P. J. et al. *Nature Rev/Cancer* 2016, 16, 716-731. (b) Clendening, J. W. et. A.l *Proc Natl Acad Sci USA* 2010, 107, 15051-15056], ZOL is expected to directly downregulate farnesylation and that could be one of the mechanisms of action responsible for the antitumor effects, in addition to indirectly downregulating geranylgeranylation via depletion of the intracellular levels of FPP (FIG. 1a).

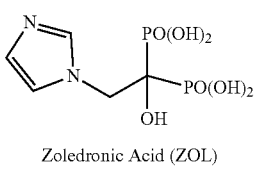

Zoledronic Acid (ZOL)

The geranylgeranylated GTPase proteins (e.g. Rap1A, Rho Ram, Rac and Cdc42) play an indispensable role in signal transduction cascades of cell growth, differentiation, and survival. Inhibition of hGGPPS leads to the pleiotropic biochemical consequences. For example, decrease in Rho kinase responses (as a consequence of statin treatment) has been implicated in increased production of endothelium-derived nitric oxide (NO) (Rikitake and Liao *Circ Res* 2005, 97, 1232-1235). Endothelial dysfunction is characterized as the decreased synthesis, release, and/or activity of endothelial-derived NO and is believed to be a strong predictor of cardiovascular disease. Therefore, the regulation of NO by Rho may be an important mechanism underlying the cardiovascular protective effect of statins. Geranylgeranylated GTPases are also implicated in oncogenesis (Sorrentino et al. *Nature Cell Biol.* 2014, 16, 357-366). Inhibition of hGGPPS decreases the migration/metastasis of highly invasive breast cancer cells (Dudakovic et al. *Invest New Drugs* 2011, 29, 912-920), induces autophagy in prostate cancer (Wasko et al. *J Pharamacol Exp Ther* 2011, 337, 540-546) and plays a role in the survival of glioma cells (Yu et al. *BMC Cancer* 2014, 14:248; doi: 10.1186/1471-2407-14-248).

Only a handful of exploratory compounds that are reasonably potent inhibitors of hGGPPS have been reported in the literature. However, based on the reported biological activity and the chemical structures of these compounds, none are expected to exhibit the required biopharmaceutical properties for a clinically useful therapeutic agent. Bisphosphonates with long side chains, such as analog A, have been shown to inhibit hGGPPS [(a) Zhang, Y. et al. *J. Am. Chem. Soc.* 2009, 131, 5153-5162. (b) Zhang, Y. et al. *Angew. Chem. Int. Ed.* 2010, 49, 1136-1138]. Substituted biphenyl bisphosphonates such as compound B, have also been described as selective hGGPPS inhibitors, however this compound is not very potent (Guo, R. T. et al. *Proc Natl Acad Sci USA* 2007, 104, 10022-10027). Structural mimics of isoprenoids, such as the branched bisphosphonate digeranyl analog C and the triazole FPP mimic D are amongst the most potent hGGPPS inhibitors reported to date [(a) Shull, L. W. et al. *Bioorg Med Chem* 2006, 14, 4130-4136. (b) Barney, R. J. et al. *Bioorg Med Chem* 2010, 18, 7212-7220. (c) Wills, V. S. et al. *ACS Med. Chem. Lett.* 2015, 6, 1195-1198]. However, compounds characterized by long hydrocarbon chains (such as compound A, C and D), in addition to multiple non-aromatic double bonds (such as compounds C and D) are highly susceptible to cytochrome P 450 metabolic oxidation (i.e. low metabolic stability) and may also suffer from poor chemical stability.

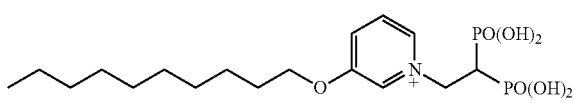

A

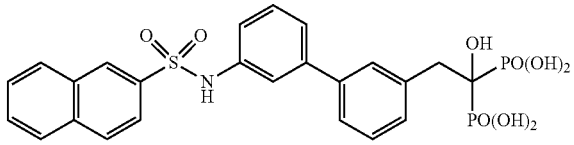

B

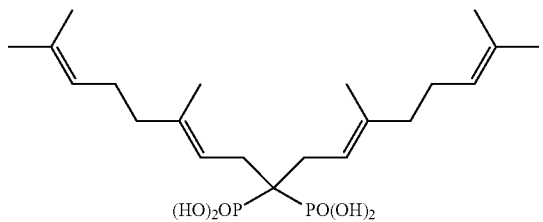

C

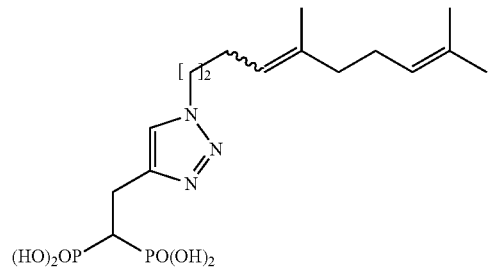

(mixture of E/Z)

D

PCT patent application publication no. WO 2016/081281 discloses lipophilic bisphosphonate compounds that are reported to inhibit FPPS and/or GGPPS. US patent application US2015/0322099A1 and PCT application WO 2014/008407 disclose GGPPS selective inhibitors consisting of bisphosphonate compounds with one aromatic chain and one aliphatic isoprenoid chain attached via an ether linkage. PCT patent application publication no. WO 2014/176546 teaches that GGPPS inhibitors may be useful for treating fibrosis, such as pulmonary fibrosis.

The design and synthesis of novel C-6-substituted thieno-pyrimidine-based bisphosphonates (ThP-BPs) inhibitors of hFPPS was recently reported. [(a) Leung, C. Y. et al. *J. Med. Chem.* 2013, 56, 7939-7950. (b) De Schutter, J. W. et al. *J. Med. Chem* 2014, 57, 5764-5776.]

SUMMARY

A novel class of bicyclic heterocyclic compounds of Formula I have been prepared and found to be useful for inhibiting the biosynthesis of GGPP and geranylgeranylation of GTPases, for example via their activity as potent inhibitors of hGGPPS, which are also moderately selective against hFPPS.

Potent inhibitors of hGGPPS induce a pronounced effect in blocking cancer cell proliferation, particularly by blocking the proliferation of multiple myeloma (MM), chromic myelogenous leukemia cells and other types of cancer cell lines and leading to their apoptosis. These inhibitors perform far better than potent inhibitors of hFPPS, including the commercial drug zoledronic acid (ZOL), and C-6 substituted thienopyrimidine-based bisphosphonates. The latter are potent inhibitors of hFPPS, but not hGGPPS, with very similar physicochemical properties to the hGGPPS inhibitors disclosed herein.

Inhibitors of hGGPPS may also have a more pronounced effect in downregulating the levels of phosphorylate tau protein (P-Tau) in human neurons than hFPPS inhibitors. Therefore, inhibitors of hGGPPS may also be valuable therapeutic agents for arresting the initiation or progression of P-Tau-dependent formation of neurofibrillary tangles, which can cause neurodegeneration and are one of the currently known hallmarks of Alzheimer's disease.

Accordingly, one aspect of the present application includes a compound of Formula I, or a pharmaceutically acceptable salt, solvate and/or prodrug thereof:

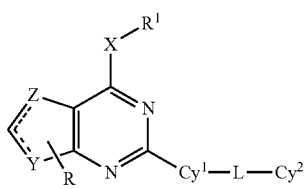

(I)

wherein:
R is selected from H, $C_{1-2}$alkyl and $C_{1-2}$fluoroalkyl;
$R^1$ is a pyrophosphate bioisostere;
X is selected from O, $CH_2$, NH and $N(C_{1-4}$alkyl);
Z and Y are independently selected from S, O, $NR^3$ and $CR^3R^{3'}$;
$Cy^1$ is selected from $C_{6-10}$aryl, $C_{5-10}$heteroaryl, $C_{3-10}$cycloalkyl and $C_{3-10}$heterocycloalkyl each of which are unsubstituted or substituted with one or two substituents independently selected from halo, cyano, hydroxyl, $NH_2$, $NHC_{1-6}$alkyl, $NHC_{3-4}$cycloalkyl, $N(C_{1-6}$alkyl)($C_{1-6}$alkyl), $C_{1-6}$fluoroalkyl, $C_{1-6}$alkyl, $C_{3-6}$cycloalkyl, $C_{1-6}$fluoroalkoxy, $C_{1-6}$alkoxy and $C_{3-6}$cycloalkoxy;
$Cy^2$ is selected from $C_{3-10}$cycloalkyl, $C_{3-10}$heterocycloalkyl, $C_{6-10}$aryl and $C_{5-10}$heteroaryl, each of which is unsubstituted or substituted with one to three substituents independently selected from halo, cyano, hydroxyl, $NH_2$, $NHC_{1-6}$alkyl, $N(C_{1-6}$alkyl)($C_{1-6}$alkyl), $NHC_{3-6}$cycloalkyl, $C_{1-6}$fluoroalkyl, $C_{1-6}$alkyl, $C_{3-6}$cycloalkyl, $C_{1-6}$fluoroalkoxy, $C_{3-6}$cycloalkoxy, phenyl, $C_{3-6}$heterocycloalkyl, $C_{5-6}$heteroaryl and $C_{1-6}$alkoxy;
L is selected from a direct bond, C(O), O, AC(O)$(CR^4R^{4'})_m(A')_p$, $ASO_2(CR^4R^{4'})_m(A')_p$, $C(O)A(CR^4R^{4'})_m(A')_p$ and $SO_2A(CR^4R^{4'})_m(A')_p$;
$R^3$ and $R^{3'}$ are independently selected from H, $C_{3-6}$cycloalkyl and $C_{1-4}$alkyl, or when the atom to which $R^3$ is attached is sp$_2$ hybridized, $R^3$ is not present;
$R^4$ and $R^{4'}$ are independently selected from H, halo, $C_{1-4}$fluoroalkyl, $C_{1-4}$alkyl, $C_{3-6}$cycloalkyl, $C_{1-4}$fluoroalkoxy, $C_{3-6}$cycloalkoxy and $C_{1-4}$alkoxy;
m is selected from 0, 1 and 2;
p is selected from 0 and 1;
A is selected from NH and $N(C_{1-4}$ alkyl);
A' is selected from O, NH and $N(C_{1-4}$ alkyl) when m is 1 or 2 and A' is selected from NH and $N(C_{1-4}$ alkyl) when m is 0; and
---- represents a single or double bond, provided that two double bonds are not adjacent to each other.

The present application also includes a compound of Formula I, or a pharmaceutically acceptable salt, solvate and/or prodrug thereof:

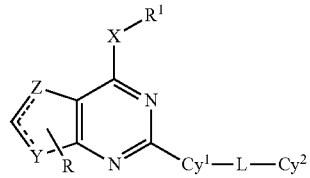

(I)

wherein:
R is selected from H, $C_{1-2}$alkyl and $C_{1-2}$fluoroalkyl;
$R^1$ is a pyrophosphate bioisostere;
X is selected from O, $CH_2$, NH and $N(C_{1-4}$alkyl);
Z and Y are independently selected from S, O, $NR^3$ and $CR^3R^{3'}$;
$Cy^1$ is selected from $C_{6-10}$aryl, $C_{5-10}$heteroaryl, $C_{3-10}$cycloalkyl and $C_{3-10}$heterocycloalkyl, each of which are unsubstituted or substituted with one or two substituents independently selected from halo, cyano, hydroxyl, $NH_2$, $NHC_{1-6}$alkyl, $N(C_{1-6}$alkyl)($C_{1-6}$alkyl), $C_{1-6}$fluoroalkyl, $C_{1-6}$alkyl, $C_{1-6}$fluoroalkoxy and $C_{1-6}$alkoxy;
$Cy^2$ is selected from $C_{3-10}$cycloalkyl, $C_{3-10}$heterocycloalkyl, $C_{6-10}$aryl and $C_{5-10}$heteroaryl, each of which is unsubstituted or substituted with one to three substituents independently selected from halo, cyano, hydroxyl, $NH_2$, $NHC_4$alkyl, $N(C_{1-6}$alkyl)($C_{1-6}$alkyl), $C_{1-6}$fluoroalkyl, $C_{1-6}$alkyl, $C_{1-6}$fluoroalkoxy and $C_{1-6}$alkoxy;
L is selected from a direct bond, C(O), O, AC(O)$(CR^4R^{4'})_m(A')_p$, $ASO_2(CR^4R^{4'})_m(A')_p$, $C(O)A(CR^4R^{4'})_m(A')_p$ and $SO_2A(CR^4R^{4'})_m(A')_p$;
$R^3$ and $R^{3'}$ are independently selected from H and $C_{1-4}$alkyl, or when the atom to which $R^3$ is attached is sp$_2$ hybridized, $R^3$ is not present;
$R^4$ and $R^{4'}$ are independently selected from H, halo, $C_{1-4}$fluoroalkyl, $C_{1-4}$alkyl, $C_{1-4}$fluoroalkoxy and $C_{1-4}$alkoxy;
m is selected from 0, 1 and 2;
p is selected from 0 and 1;
A is selected from NH and $N(C_{1-4}$ alkyl);
A' is selected from O, NH and $N(C_{1-4}$ alkyl) when m is 1 or 2 and A' is selected from NH and $N(C_{1-4}$ alkyl) when m is 0; and
---- represents a single or double bond, provided that two double bonds are not adjacent to each other.

The present application also includes a composition comprising one or more compounds of the application and a carrier. In an embodiment, the composition is a pharmaceutical composition comprising one or more compounds of the application and a pharmaceutically acceptable carrier.

The compounds of the application inhibit hGGPPS function. Therefore, the compounds of the application are useful for treating diseases, disorders or conditions mediated by hGGPPS. Accordingly, the present application also includes a method of treating a disease, disorder or condition mediated by or through hGGPPS comprising administering a therapeutically effective amount of one or more compounds of the application to a subject in need thereof.

In a further embodiment, the compounds of the application are used as medicaments. Accordingly, the application also includes a compound of the application for use as a medicament.

The present application also includes a method of treating a disease, disorder or condition that is mediated by hGGPPS or is treatable by inhibiting geranylgeranylation comprising administering a therapeutically effective amount of one or more compounds of the application to a subject in need thereof. The present application also includes a use of one or more compounds of the application for treatment of a disease, disorder or condition mediated by hGGPPS or treatable by inhibiting geranylgeranylation as well as a use of one or more compounds of the application for the preparation of a medicament for treatment of a disease, disorder or condition mediated by hGGPPS or treatable by inhibiting geranylgeranylation. The application further includes one or more compounds of the application for use in treating a disease, disorder or condition mediated by hGGPPS or treatable by inhibiting geranylgeranylation.

The present application also provides evidence that inhibitors of hGGPPS exhibit much stronger antimyeloma effects than inhibitors of hFPPS with equivalent potency and very similar structural and physicochemical properties. The mRNA levels of hFPPS and hGGPPS were analyzed in various MM cell lines reported in the Cancer Cell Line Encyclopedia [refer to: (a) The Cancer Cell Line Encyclopedia and Genomics of Drug Sensitivity in Cancer Investigators. Pharmacogenomic agreement between two cancer cell line data sets *Nature* 2015, 528, 84-87; (b) Barretina, J. et al. The Cancer Cell Line Encyclopedia enables predictive modelling of anticancer drug sensitivity. *Nature* 2012, 483, 603-607]. Interestingly, it was found that the mRNA levels of hFPPS were consistently significantly higher than those of hGGPPS in all MM human cells (FIG. 2*a*). Additionally, the mRNA levels of hFPPS and hGGPPS were analyzed in primary MM cells taken from bone marrow specimens of MM patient participating in a large clinical trial (data from CD138-selected MM cells from 724 patient bone marrow specimens obtained at diagnosis; CoMMpass IA10 Clinical trial data). It was confirmed that mRNA expression of hFPPS is also significantly higher than of hGGPPS in tumors from these patients. (FIG. 2*b*). Collectively, these findings in MM cells and myeloma patients suggest a much higher (%) target engagement of the human GGPPS in vivo and consequently, a more effective inhibition of GGPP-dependent activation of GTPases in vivo upon treatment with an hGGPPS inhibitor than with an equipotent and physicochemically equivalent inhibitor of hFPPS.

The present application also provides evidence that the compounds disclosed herein, which are inhibitors of hGGPPS, also block cancer cell proliferation of many types of cancers (FIG. 3*c*), including cancer cell lines that are resistant to current chemotherapeutic drugs, for example, doxorubicin, such as the multidrug resistant ovarian cancer cells (ADR-RES; FIG. 3*b*). However, the compounds disclosed herein, which are inhibitors of hGGPPS, are significantly less toxic to normal human bronchial cells (NHBE) than the broad-spectrum antitumor agent doxorubicin (FIG. 3*a*).

The present application also provides evidence that the compounds disclosed herein, which are inhibitors of hGGPPS, also block geranylgeranylation of Rap 1A in MM cancer cells (FIG. 8*a*), as well as the peripheral blood of Vk*MYC transgenic mice (FIG. 8*b*), without causing overt toxicity. These mice are an ideal MM disease model, shown to clinically recapitulate the human MM disease.

The present application also provides evidence that the compounds disclosed herein, which are inhibitors of hGGPPS, are metabolically highly stable in male CD-1 mouse liver microsomes (MLM), Sprague-Dawley rat liver microsomes (RLM) and human liver microsomes (HLM).

In an embodiment, the disease, disorder or condition mediated by hGGPPS or treatable by inhibiting geranylgeranylation is a neoplastic disorder. In an embodiment, the treatment is in an amount effective to ameliorate at least one symptom of the neoplastic disorder, for example, reduced cell proliferation or reduced tumor mass, volume or distribution in a subject in need of such treatment.

Bisphosphonate inhibitors of hGGPPS are also known to block activity of geranylgeranylated proteins, such as cdc42, Rac, and Rho in osteoclasts, which is directly related to the antiresorptive effects in bone. Therefore, the compounds disclosed herein, which are bisphosphonate inhibitors of hGGPPS that bind with equivalent affinity to bone as zoledronic acid and riserdonic acid, as determined using the $^1$H NMR-based method published by Novartis (see (a) Jahnke, W. et al. *ChemMedChem* 2010, 5, 770-776 and (b) *Angew. Chem. Int. Ed.* 2015, 54, 14575-14579) may be used for the treatment of bone disorders such as osteoporosis and cancer-related lytic bone disease. Therefore, in an embodiment, the disease, disorder or condition mediated by hGGPPS, or treatable by inhibiting geranylgeranylation, is a bone disorder, such as osteoporosis and cancer-related lytic bone disease.

In an embodiment, the disease, disorder or condition mediated by hGGPPS, or treatable by inhibiting geranylgeranylation, is cancer.

In an embodiment, the disease, disorder or condition mediated by hGGPPS, or treatable by inhibiting geranylgeranylation, is a disease, disorder or condition associated with an uncontrolled and/or abnormal cellular activity affected directly or indirectly by an inhibition of hGGPPS. In another embodiment, the uncontrolled and/or abnormal cellular activity that is affected directly or indirectly by inhibition of hGGPPS is proliferative activity in a cell.

The application also includes a method of inhibiting proliferative activity in a cell, comprising administering or delivering an effective amount of one or more compounds of the application to the cell.

In an embodiment, the disease, disorder or condition mediated by hGGPPS, or treatable by inhibiting geranylgeranylation, are taupathies, leading to neurodegeneration. Taupathies have been strongly implicated with the onset and progression of Alzheimer's Disease. Therefore, in an embodiment, the disease, disorder or condition mediated by hGGPPS, or treatable by inhibiting geranylgeranylation, is Alzheimer's Disease.

In a further embodiment the disease, disorder or condition mediated by hGGPPS, or treatable by inhibiting geranylgeranylation, is cancer and the one or more compounds of the application are administered in combination with one or more additional cancer treatments. In another embodiment, the additional cancer treatment is selected from radiotherapy, chemotherapy, targeted therapies, such as antibody therapies, and small molecule therapies, such as tyrosine-kinase inhibitors, immunotherapy, hormonal therapy and anti-angiogenic therapies.

In other embodiments, the present compounds are useful medically across the broad range of medical conditions that are connected with the numerous pathways regulated in full or in part by the prenylation of proteins including, cancer, inflammation and cardiovascular diseases.

In other embodiments, the present compound may be most useful for the treatment of cancer, and in particular in treating both the primary malignancy of multiple myeloma, as well as its characteristic lytic bone disease.

The application additionally provides a process for the preparation of compounds of the application. General and specific processes are discussed in more detail below and set forth in the Examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The application will be described in greater detail with reference to the drawing in which:

FIG. 7 contains inhibitory activity ($IC_{50}$ values) of prior art compound 6-I (an inhibitor of hFPPS; of WO2014/078957) compared to the exemplary hGGPPS inhibitor compound I-5 of the present application, as well as their physicochemical properties including their Clog P values and C-18 reverse phase HPLC retention times; the latter properties are reflective of the physicochemical similarities between the two compounds I-5 and 6-I FIG. 8 contains the Wester blot data indication a dose dependent inhibition of Rap 1A prenylation upon treatment with inhibitor compound I-37, more specifically, (a) shows the intracellular levels of unprenylated Rap1A in multiple myeloma cells RPMI-8226 treated with inhibitor compound I-37 over a 48 hour period and (b) the intracellular levels of unprenylated Rap 1A in the peripheral blood of Vk*MYC transgenic mice, with advanced MM disease symptoms after treatment with inhibitor compound I-37 at 1 mg/Kg and 5 mg/Kg dose with 17 doses over a period or 16 days (with a drug holiday during the weekends within that period).

DETAILED DESCRIPTION

I. Definitions

Figure 1:
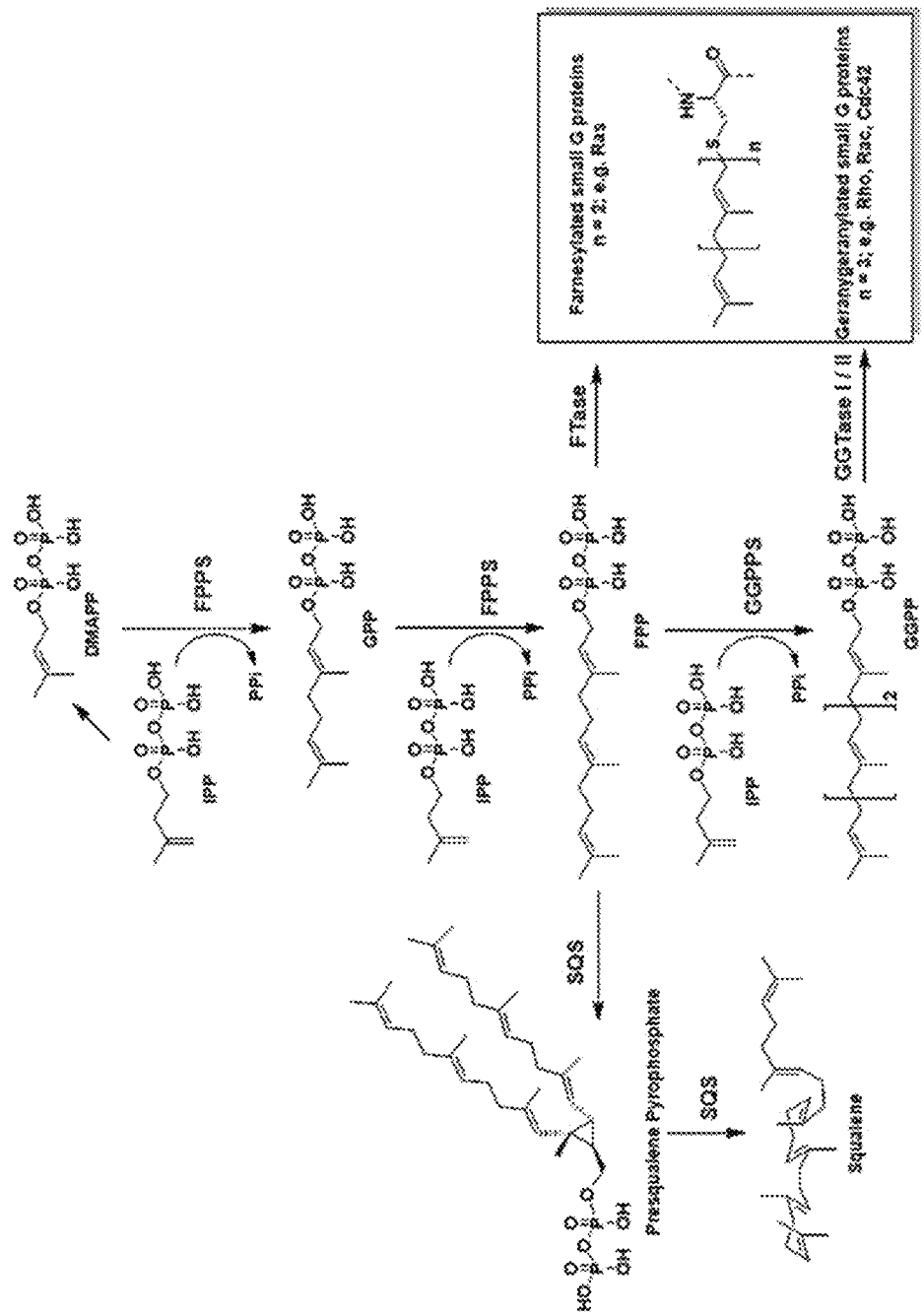
FIG. 1 contains schematics showing (a) the biosynthesis of isoprenoids; the structures of metabolites associated with isoprenois, including FPP and GGPP are indicated, and (b) the mevalonate pathways; current classes of drugs that modulate the function of key enzymes (i.e. the statins and the bisphosphonates) are indicated as well as the enzymes hFPPS and hGGPS.
Figure 1:
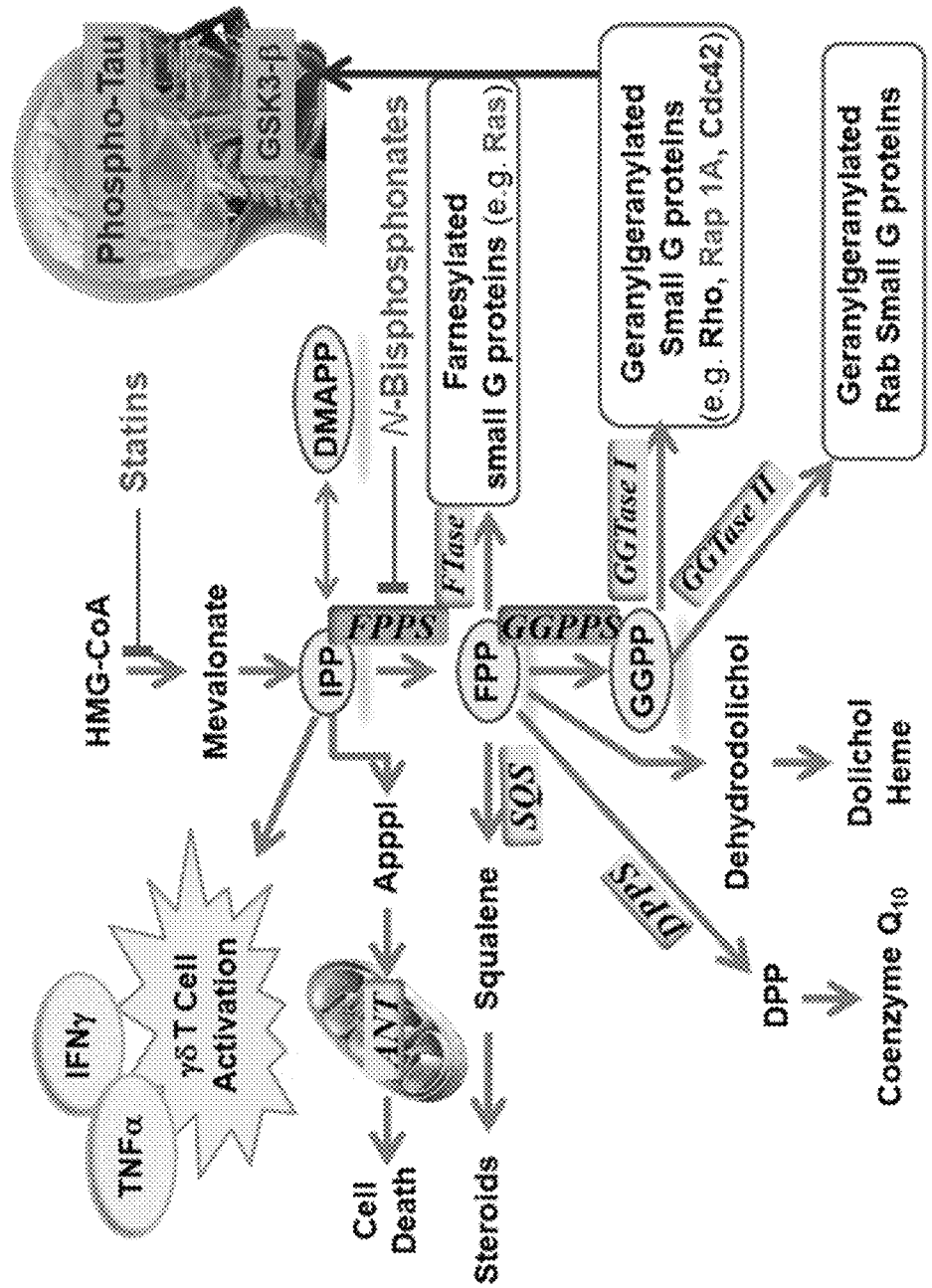
Figure 2A:
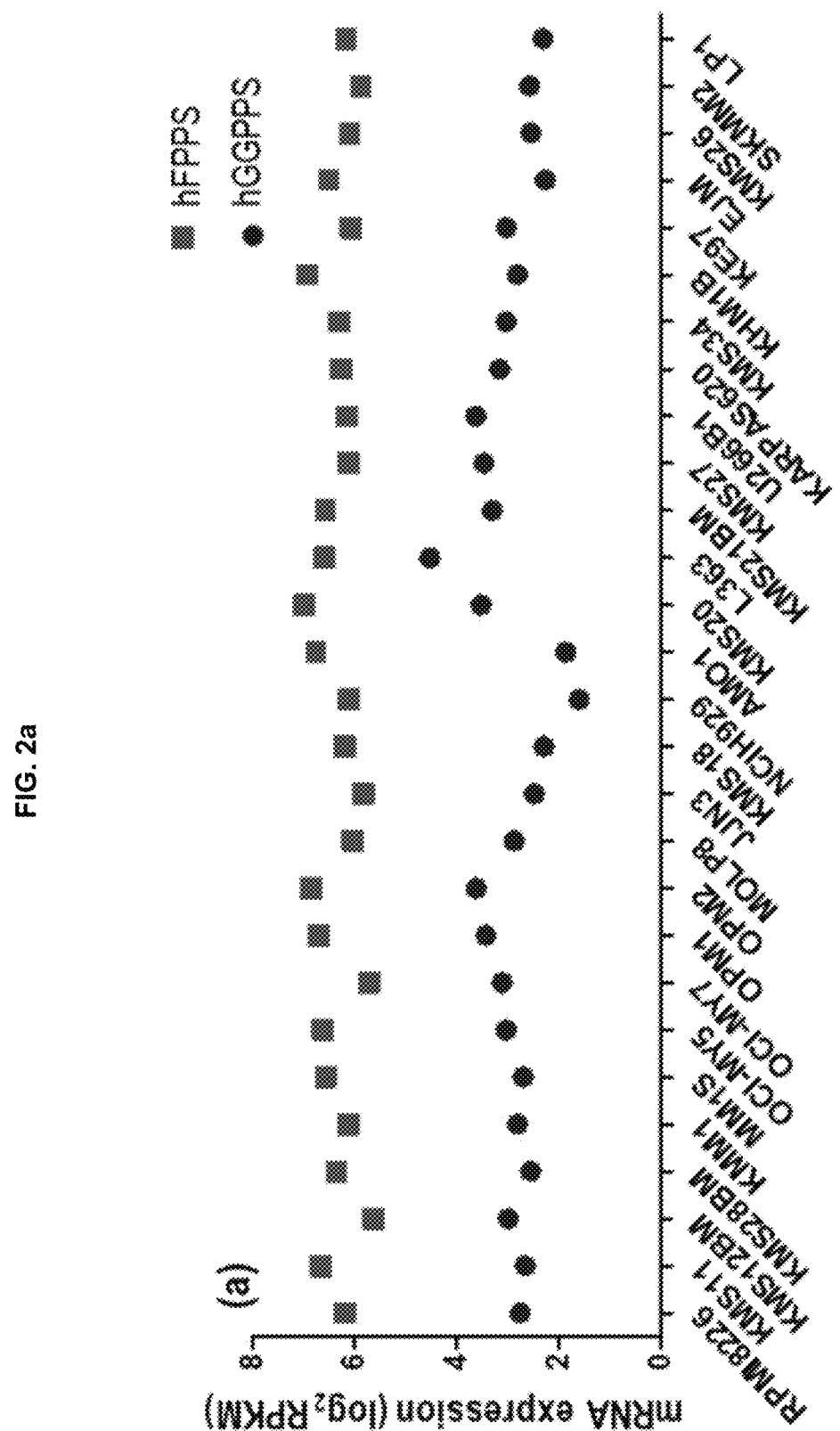
FIG. 2 shows data from (a) the mRNA levels of hFPPS and hGGPPS in various MM cell lines reported in the Cancer Cell Line Encyclopedia and (b) the CoMM IA10 clinical trial, which shows the mRNA expression level of hFPPS is higher than that of hGGPPS in bone marrow samples of multiple myeloma patients.
Figure 2B:
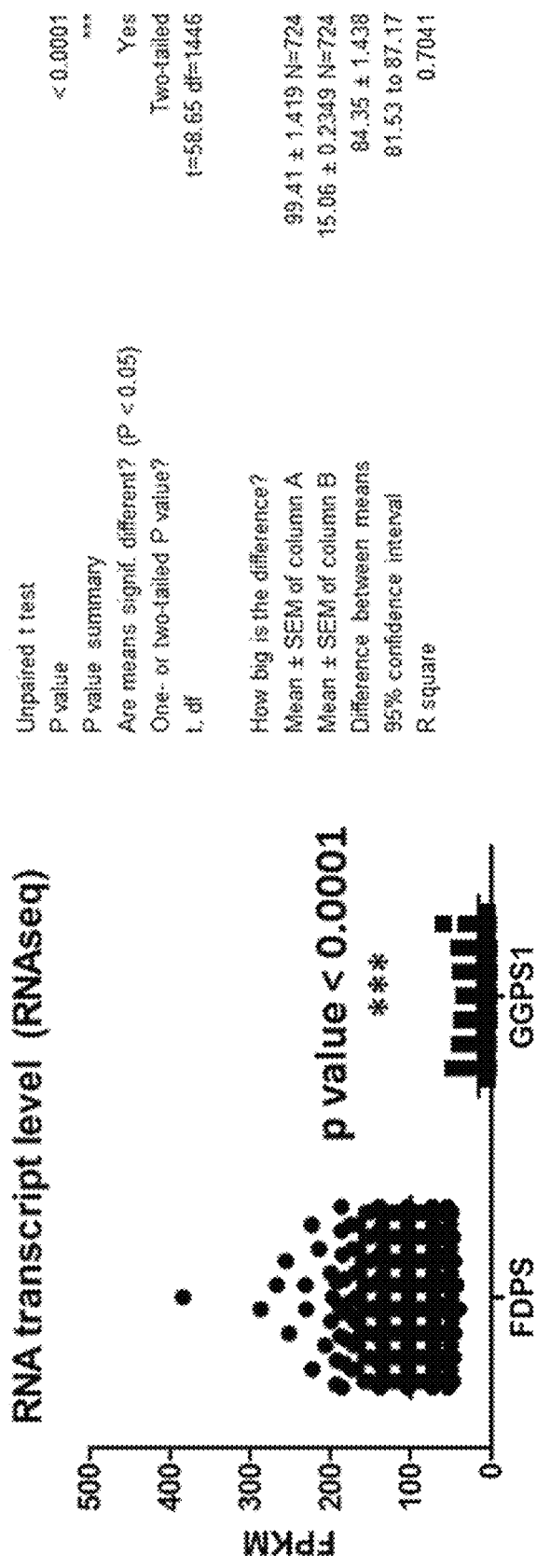

Unless otherwise indicated, the definitions and embodiments described in this and other sections are intended to be applicable to all embodiments and aspects of the application herein described for which they are suitable as would be understood by a person skilled in the art. Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program such as ChemDraw, ACD/ChemSketch, Version 5.09/September 2001, Advanced Chemistry Development, Inc., Toronto, Canada.

The term "compound of the application" or "compound of the present application" and the like as used herein refers to a compound of Formula I or pharmaceutically acceptable salts, solvates and/or radiolabeled versions thereof.

The term "composition of the application" or "composition of the present application" and the like as used herein refers to a composition, such as a pharmaceutical composition, comprising one or more compounds of Formula I, or pharmaceutically acceptable salts, solvates and/or radiolabeled versions thereof.

The term "and/or" as used herein means that the listed items are present, or used, individually or in combination. In effect, this term means that "at least one of" or "one or more" of the listed items is used or present. The term "and/or" with respect to pharmaceutically acceptable salts, solvates and/or radiolabeled versions thereof means that the compounds of the application exist as individual salts, hydrates or radiolabeled versions, as well as a combination of, for example, a salt of a solvate of a compound of the application or a salt of a radiolabeled version of a compound of the application.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present application, the term "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements, or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of" as used herein is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound named or depicted herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomers which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The expression "proceed to a sufficient extent" as used herein with reference to the reactions or process steps disclosed herein means that the reactions or process steps proceed to an extent that conversion of the starting material or substrate to product is sufficient for the given reaction. Conversion may be sufficient when greater than about 5, 10, 15, 20, 25, 30, 35, 40, 45, 50, 55, 60, 65, 70, 75, 80, 85, 90, 95 or 100% of the starting material or substrate is converted to product.

Based on IUPAC rules, numbering of the atoms around the biclyclic heterocyclic core of Formula I will vary depending on the exact structure. For simplicity, references to C-2 and C-4 carbons are assigned based on the pyrimidine ring only as shown below:

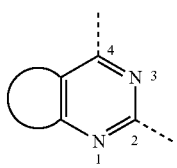

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{0-6}$alkylene means an alkylene group is not present ("$C_0$alkylene") or an alkylene group having 1, 2, 3, 4, 5 or 6 carbon atoms.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "haloalkyl" as used herein refers to an alkyl group wherein one or more, including all of the hydrogen atoms are replaced by a halogen atom. In an embodiment, the halogen is fluorine, in which case the haloalkyl is referred to herein as a "fluoroalkyl" group.

The term "alkoxy" as used herein, whether it is used alone or as part of another group, refers to the group "alkyl-O—" or "—O-alkyl". The term $C_{1-10}$alkoxy means an alkyl group having 1, 2, 3, 4, 5, 6, 7, 8, 9 or 10 carbon atoms bonded to an oxygen atom. Exemplary alkoxy groups include without limitation methoxy, ethoxy, propoxy, isopropoxy, butoxy, t-butoxy and isobutoxy.

The term "cycloalkyl," as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "cycloalkoxy," as used herein, whether it is used alone or as part of another group, refers to the group "cycloalkyl-O—" or "—O-cycloalkyl". The number of carbon atoms that are possible in the referenced cycloalkyl group are indicated by the numerical prefix "$C_{n1-n2}$". For example, the term $C_{3-10}$cycloalkoxy means an cycloalkyl group having 3, 4, 5, 6, 7, 8, 9 or 10 carbon atoms bonded to an oxygen atom.

The term "aryl" as used herein, whether it is used alone or as part of another group, refers to carbocyclic groups containing at least one aromatic ring. Aryl groups contain one or more than one ring. The number of carbon atoms that are possible in the referenced aryl group are indicated by the numerical prefix "$C_{n1-n2}$". For example, the term $C_{6-10}$aryl means an aryl group having 6, 7, 8, 9 or 10 carbon atoms.

The term "heterocycloalkyl" as used herein, whether it is used alone or as part of another group, refers to non-aromatic cyclic groups containing 3 to 10 atoms, and at least one ring in which one or more of the atoms are a heteromoiety selected from O, S, N, NH and N$C_{1-6}$alkyl. Heterocycloalkyl groups are either saturated or unsaturated (i.e. contain one or more double bonds) and contain one or more than one ring. When a heterocycloalkyl group contains more than one ring, the rings may be fused, bridged, spirofused or linked by a bond. When a heterocycloalkyl group contains the prefix $C_{n1-n2}$ this prefix indicates the number of carbon atoms in the corresponding carbocyclic group, in which one or more of the ring atoms is replaced with a heteromoiety as defined above.

The term "heteroaryl" as used herein refers to cyclic groups containing from 5 to 10 atoms, at least one aromatic ring and at least one a heteromoiety selected from O, S, N, NH and $NC_{1-6}$alkyl. Heteroaryl groups contain one or more than one ring. When a heteroaryl group contains more than one ring, the rings may be fused, bridged, spirofused or linked by a bond. When a heteroaryl group contains the prefix $C_{n1-n2}$ this prefix indicates the number of carbon atoms in the corresponding aryl group, in which one or more, suitably 1 to 5, of the ring atoms is replaced with a heteromoiety as defined above.

A 5-membered heteroaryl is a heteroaryl with a ring having five ring atoms, wherein 1, 2 or 3 ring atoms are a heteromoiety selected from O, S, NH and $NC_{1-6}$alkyl.

A 6-membered heteroaryl is a heteroaryl with a ring having six ring atoms wherein 1, 2 or 3 ring atoms are a heteromoiety selected from O, S, N, NH and $NC_{1-6}$alkyl.

A 5-membered heterocycloalkyl is a heterocycloalkyl with a ring having five ring atoms, wherein 1, 2 or 3 ring atoms are a heteromoiety selected from O, S, NH and $NC_{1-6}$alkyl.

A 6-membered heterocycloalkyl is a heterocycloalkyl with a ring having six ring atoms wherein 1, 2 or 3 ring atoms are a heteromoiety selected from O, S, N, NH and $NC_{1-6}$alkyl.

All cyclic groups, including aryl and cyclo a groups, contain one or more than one ring (i.e. are polycyclic). When a cyclic group contains more than one ring, the rings may be fused, bridged or spirofused.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

As a prefix, the term "substituted" as used herein refers to a structure, molecule or group in which one or more available hydrogen atoms are replaced with one or more other chemical groups.

As a suffix, the term "substituted" as used herein in relation to a first structure, molecule or group, followed by one or more variables or names of chemical groups, refers to a second structure, molecule or group that results from replacing one or more available hydrogens of the first structure, molecule or group with the one or more variables or named chemical groups.

The term "available", as in "available hydrogen atoms" or "available atoms" refers to atoms that would be known to a person skilled in the art to be capable of replacement by another atom or substituent.

The term "optionally substituted" refers to groups, structures, or molecules that are either unsubstituted or are substituted with one or more substituents.

The term "$sp_2$ hybridized" as used herein refers to an atom that bonded to one of its neighboring atoms via a double bond.

The term "pyrophosphate bioisostere" as used herein refers to a chemical substituent or group that mimics the pyrophosphate functionality in terms of physical and/or chemical properties and which produces broadly similar biological properties to the pyrophosphate group.

The term "pyrophosphate" also known as "diphosphate" as used herein refers to the chemical group shown below, which is part of the natural substare/metabolite and product of hGGPPS. It will be understood by those skilled in the art that such a moiety can be ionized, depending on the pH of its environment, to the mono, di or tri anion

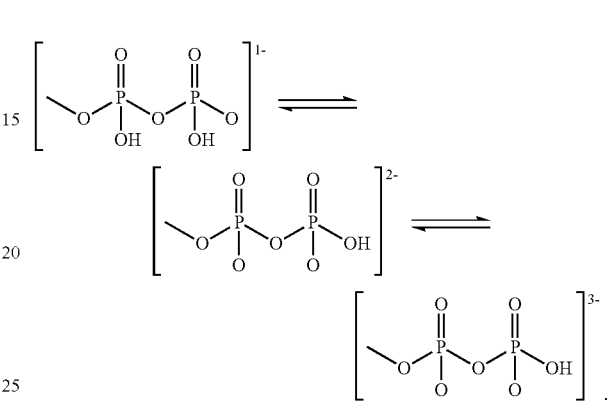

The term "amine" or "amino," as used herein, whether it is used alone or as part of another group, refers to groups of the general formula NRR', wherein R and R' are each independently selected from hydrogen or a an alkyl group, such as $C_{1-6}$alkyl.

The terms "halo" or "halogen" as used herein, whether it is used alone or as part of another group, refers to a halogen atom and includes fluoro, chloro and bromo.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in "*Protective Groups in Organic Synthesis*", T. W. Green, P. G. M. Wuts, Wiley-Interscience, New York, (4th Edition, 2007) and in Kocienski, P. Protecting Groups, 3rd Edition, 2003, Georg Thieme Verlag (The Americas).

The term "cell" as used herein refers to a single cell or a plurality of cells and includes a cell either in a cell culture or in a subject.

The term "subject" as used herein includes all members of the animal kingdom including mammals, and suitably refers to humans.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound. Basic compounds that form acid addition salts include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al. "Pharmaceutical Salts," *J. Pharm. Sci.* 1977, 66, 1-19]. The selection of the appropriate salt may be useful, for example, so that an ester functionality, if any, elsewhere in a compound is not hydrolyzed. The selection criteria for the appropriate salt will be known to one skilled in the art.

The term "solvate" as used herein means a compound, or a salt of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, the compounds of the application are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The "disease, disorder or condition" as used herein refers to a disease, disorder or condition treatable by hGGPPS enzyme inhibition and particularly using a hGGPPS enzyme inhibitor, such as a compound of the application herein described.

The term "mediated by hGGPPS" or "treatable by hGGPPS inhibition," as used herein means that the disease, disorder or condition to be treated is affected by, modulated by and/or has some biological basis, either direct or indirect, that includes hGGPPS activity, in particular, increased hGGPPS activity such as results from hGGPPS gene overexpression or hGGPPS protein over-accumulation or overexpression of proteins that are products of or precursors to hGGPPS-mediated gene expression. In a broader context, "mediated by hGGPPS" can include the large number of diseases that are caused by aberrant prenylation, for example geranylgeranylation, of proteins, as results from aberrant hGGPPS activity. As used herein, hGGPPS refers to the protein identified as the human geranylgeranyl pyrophosphate synthase enzyme (Park, J. et al. *Frontiers in Chemistry* 2014, 2, Article 50; doi:10.3389/fchem.2014.00050).

As used herein, the term "effective amount" or "therapeutically effective amount" means an amount of one or more compounds of the application that is effective, at dosages and for periods of time necessary to achieve the desired result. For example, in the context of treating a disease, disorder or condition mediated by hGGPPS, an effective amount is an amount that, for example, increases hGGPPS inhibition compared to the inhibition without administration of the one or more compounds. In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of one or more compounds or compositions of the application to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

The term "cancer" as used herein refers to cellular-proliferative disease states.

II. Compounds and Compositions of the Application

Compounds of the present application were prepared and were found to inhibit uncontrolled and/or abnormal cellular activities affected directly or indirectly by hGGPPS. In particular, compounds of the present application exhibited activity as hGGPPS inhibitors, and are therefore useful in therapy, for example for the treatment of neoplastic disorders such as cancer.

Compounds of the present application may also exhibit activity in reducing the phosphorylation of tau protein in human neurons, and could potentially be useful in therapy, for example in decelerating the progression or the initiation of phospho-tau-dependent neurofibrillary tangles in the brain, which is strongly associated with Alzheimer's disease and other tauopathies.

Accordingly, one aspect of the present application includes a compound of Formula I, or a pharmaceutically acceptable salt, solvate and/or prodrug thereof:

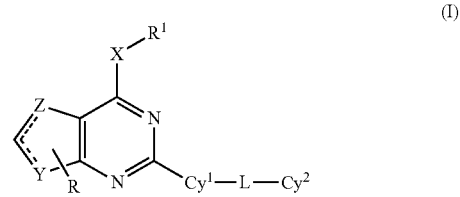

(I)

wherein:
R is selected from H, $CH_2$alkyl and $C_{1-2}$fluoroalkyl;
$R^1$ is a pyrophosphate bioisostere;
X is selected from O, $CH_2$, NH and $N(C_{1-4}alkyl)$;
Z and Y are independently selected from S, O, $NR^3$ and $CR^3R^{3'}$;
$Cy^1$ is selected from $C_{6-10}$aryl, $C_{5-10}$heteroaryl, $C_{3-10}$cycloalkyl and $C_{3-10}$heterocycloalkyl, each of which are unsubstituted or substituted with one or two substituents independently selected from halo, cyano, hydroxyl, $NH_2$, $NHC_{1-6}$alkyl, $NHC_{3-6}$cycloalkyl, $N(C_{1-6}alkyl)(C_{1-6}alkyl)$, $C_{1-6}$fluoroalkyl, $C_{1-6}$alkyl, $C_{3-6}$cycloalkyl, $C_{1-6}$fluoroalkoxy, $C_{3-6}$cycloalkoxy and $C_{1-4}$alkoxy;
$Cy^2$ is selected from $C_{3-10}$cycloalkyl, $C_{3-10}$heterocycloalkyl, $C_{6-10}$aryl and $C_{5-10}$heteroaryl, each of which is unsubstituted or substituted with one to three substituents independently selected from halo, cyano, hydroxyl, $NH_2$, $NHC_{1-6}$alkyl, $NHC_{3-6}$cycloalkyl, $N(C_{1-6}alkyl)(C_{1-6}alkyl)$, $C_{1-6}$fluoroalkyl, $C_{1-6}$alkyl, $C_{3-6}$cycloalkyl, $C_{1-6}$fluoroalkoxy, $C_{3-6}$cycloalkoxy, phenyl, $C_{3-6}$heterocycloalkyl, $C_{5-6}$heteroaryl and $C_{1-6}$alkoxy;
L is selected from a direct bond, C(O), O, $AC(O)(CR^4R^{4'})_m(A')_p$, $ASO_2(CR^4R^{4'})_m(A')_p$, $C(O)A(CR^4R^{4'})_m(A')_p$ and $SO_2A(CR^4R^{4'})_m(A')_p$;
$R^3$ and $R^{3'}$ are independently selected from H, $C_{3-6}$cycloalkyl and $C_{1-4}$alkyl, or when the atom to which $R^3$ is attached is $sp_2$ hybridized, $R^3$ is not present;
$R^4$ and $R^{4'}$ are independently selected from H, halo, $C_{1-4}$fluoroalkyl, $C_{1-4}$alkyl, $C_{3-6}$cycloalkyl, $C_{1-4}$fluoroalkoxy, $C_{3-6}$cycloalkoxy and $C_{1-4}$alkoxy;
m is selected from 0, 1 and 2;
p is selected from 0 and 1;
A is selected from NH and $N(C_{1-4}$ alkyl);
A' is selected from O, NH and $N(C_{1-4}$ alkyl) when m is 1 or 2 and A' is selected from NH and $N(C_{1-4}alkyl)$ when m is 0; and
---- represents a single or double bond, provided that two double bonds are not adjacent to each other.

In some embodiments, R is H, $CH_3$ or $CF_3$. In some embodiments R is H.

The group $R^1$ is any known pyrophosphate bioisostere. In some embodiments, the pyrophosphate bioisostere is selected from one of the following groups:
(a) a bisphosphonate, bisphosphonate ester, or analog or bioisostere of a bisphosphonate or bisphosphonate ester of the formula $(CR^5R^{5'})PO(OR^6)_2$, wherein $R^5$ is a selected from $PO(OR^6)_2$ and phosphate and phosphate ester bioisosteres selected from $CO_2R^{6'}$, $C(O)NHR^7$, $SO_3R^7$, $SO_2NHR^7$ and other such bioisosteres known in the art, for example as described in a review by Elliott, T. S. et al. The use of phosphate bioisosteres in medicinal chemistry and chemical biology. *Chem. Med. Comm.* 2012, 3, 735-751; $R^{5'}$ is selected from H, OH and halo; $R^6$ and $R^{6'}$ are independently selected from H and $C_{1-6}$alkyl and $R^7$ is selected from H, OH and $C_{1-6}$alkyl; and (b) an α,γ-diketo acid (shown below) or a heterocyclic moiety that can serve as a bioisostere of a diketo acid, such as those employed in the design of HIV integrase active site inhibitors. Examples include (but are not limited) to compounds described in the EP 1422218, WO2002/30426, WO2002/30930, WO2002/30931 and WO2002/36734.

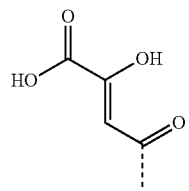

In some embodiments, $R^1$ is $(CR^5R^{5'})PO(OR^6)_2$, wherein $R^5$ is selected from $PO(OR^{6'})_2$. $CO_2R^{6'}$, $C(O)NHR^7$, $SO_3R^7$, $SO_2NHR^7$; $R^{5'}$ is selected from H, OH and halo; $R^6$ and $R^{6'}$ are independently selected from H and $C_{1-6}$alkyl; and $R^7$ is selected from H, OH and $C_{1-6}$alkyl. In some embodiments, $R^1$ is $(CR^5R^{5'})PO(OR^6)_2$, wherein $R^5$ is selected from $PO(OR^{6'})_2$, $CO_2R^{6'}$, $C(O)NHR^7$, $SO_3R^7$, $SO_2NHR^7$; $R^{5'}$ is H; $R^6$ and $R^{6'}$ are independently selected from H and $CH_3$; and $R^7$ is selected from H, OH and $CH_3$. In some embodiments, $R^1$ is $(CR^5R^{5'})PO(OR^6)_2$, wherein $R^5$ is $PO(OR^{6'})_2$, $R^{5'}$ is H; and $R^6$ and $R^{6'}$ are both H.

In some embodiments, X is selected from O, $CH_2$, NH and $NCH_3$. In some embodiments X is NH.

In some embodiments, the compounds of Formula I have the following structure:

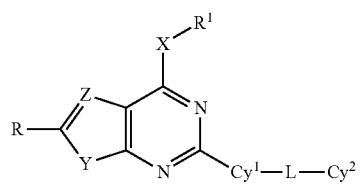

(I)

wherein Z is selected from S, O, N and CH; Y is selected from S, O, NH and $CH_2$; and X, $R^1$, $Cy^1$, L and $Cy^2$ are as defined above.

In some embodiments, the bicyclic core structure in the compounds of Formula I is selected from any one of the structural isomers shown below:

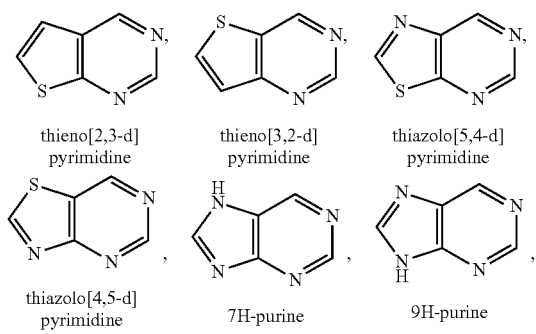

thieno[2,3-d]pyrimidine, thieno[3,2-d]pyrimidine, thiazolo[5,4-d]pyrimidine, thiazolo[4,5-d]pyrimidine, 7H-purine, 9H-purine

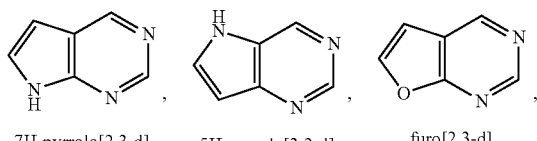

7H-pyrrolo[2,3-d]pyrimidine, 5H-pyrrolo[3,2-d]pyrimidine, furo[2,3-d]pyrimidine

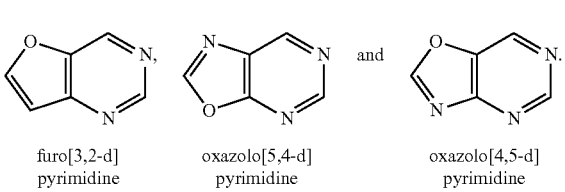

furo[3,2-d]pyrimidine, oxazolo[5,4-d]pyrimidine, and oxazolo[4,5-d]pyrimidine

In some embodiments, the compounds of Formula I have the following structure:

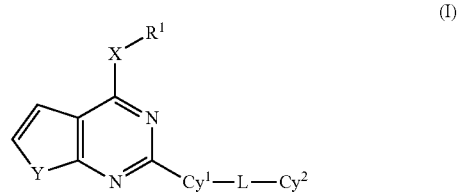

(I)

wherein Y is selected from S, O, NH and $CH_2$; and X, $R^1$, $Cy^1$, L and $Cy^2$ are as defined above.

In some embodiments, the compounds of the application are thieno[2,3-d]pyrimidines, i.e. Z is CH and Y is S and the compounds of Formula I have the following structure:

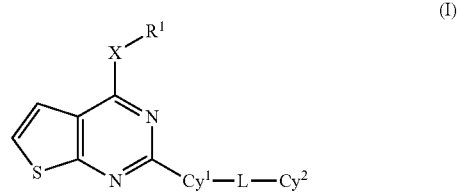

(I)

wherein X, $R^1$, $Cy^1$, L and $Cy^2$ are as defined above.

In some embodiments, the compounds of the application are thieno[3,2-d]pyrimidin-4-amine, i.e. Z is S and Y is CH and the compounds of Formula I have the following structure:

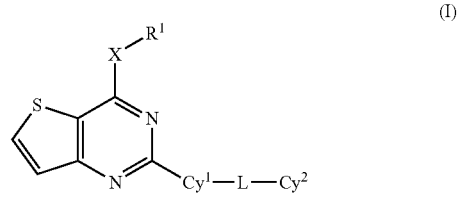

(I)

wherein X, $R^1$, $Cy^1$, L and $Cy^2$ are as defined above.

In some embodiments, the compounds of the application are thiazolo[5,4-d]pyrimidin-7-amine, i.e. Z is N and Y is S and the compounds of Formula I have the following structure:

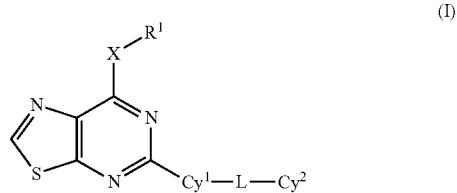
(I)

wherein X, $R^1$, $Cy^1$, L and $Cy^2$ are as defined above.

In some embodiments, the compounds of the application are 9H-purin-6-amine, i.e. Z is N and Y is $NR^3$ and the compounds of Formula I have the following structure:

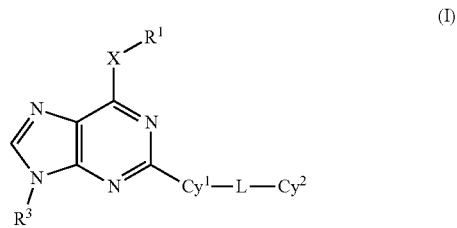
(I)

wherein X, $R^1$, $R^3$, $Cy^1$, L and $Cy^2$ are as defined above.

In some embodiments, the compounds of the application are 7H-pyrrolo[2,3-d]pyrimidin-4-amine, i.e. Z is CH and Y is $NR^3$ and the compounds of Formula I have the following structure:

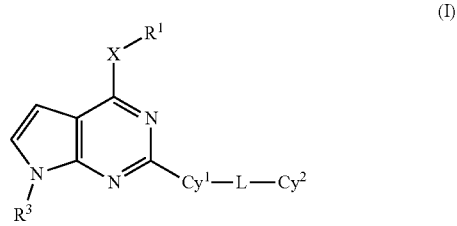
(I)

wherein X, $R^1$, $R^3$, $Cy^1$, L and $Cy^2$ are as defined above.

In some embodiments, $Cy^1$ is selected from phenyl, $C_{3-6}$cycloalkyl, $C_{5-10}$heteroaryl and $C_{5-10}$heterocycloalkyl. In some embodiments, $Cy^1$ is selected from phenyl, naphthyl, cyclopropyl, cyclobutyl, cyclopentyl, cyclohexyl, 5-membered heteroaryl, 6-membered heteroaryl, 10-membered heteroaryl, 5-membered heterocycloalkyl and 6-membered heterocycloalkyl. In some embodiments, $Cy^1$ is selected from $C_{6-10}$aryl and $C_{5-10}$heteroaryl. In some embodiments, $Cy^1$ is selected from phenyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridinyl, pyrazinyl, pyrimidinyl, triazinyl, pyrrolidinyl, piperazinyl, piperidinyl, morpholinyl and pyridazinyl, each of which is unsubstituted or substituted with one or two substituents. In some embodiments, $Cy^1$ is selected from phenyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridinyl, pyrazinyl, pyrimidinyl, triazinyl and pyridazinyl, each of which is unsubstituted or substituted with one or two substituents. In some embodiments, $Cy^1$ is selected from phenyl, thienyl, furyl, pyrrolyl, pyridinyl, pyrazinyl, pyrrolidinyl, piperazinyl, piperidinyl and pyrimidinyl, each of which is unsubstituted or substituted with one substituent. In some embodiments, $Cy^1$ is selected from phenyl, thienyl, furyl, pyrrolyl, pyridinyl, pyrazinyl and pyrimidinyl, each of which is unsubstituted or substituted with one substituent. In some embodiment $Cy^1$ is unsubstituted phenyl.

In some embodiments, L is selected from a direct bond, C(O), O, AC(O)$(CR^4R^{4'})_m(A')_p$, $ASO_2(CR^4R^{4'})_m(A')_p$, C(O)A$(CR^4R^{4'})_m(A')_p$ and $SO_2A(CR^4R^{4'})_m(A')_p$. In some embodiments, L is selected from a direct bond, NHC(O)$(CR^4R^{4'})_m(A')_p$, $NHSO_2(CR^4R^{4'})_m(A')_p$, C(O)NH$(CR^4R^{4'})_m(A')_p$ and $SO_2NH(CR^4R^{4'})_m(A')_p$. In some embodiments, L is selected from a direct bond, $NHSO_2$, $SO_2NH$, NHC(O), NHC(O)$CH_2O$, NHC(O)CH(O$CH_3$), NHC(O)CH($CH_3$), NHC(O)$CH_2$, NHC(O)$CH_2CH_2$, NHC(O)C($CF_3$)(O$CH_3$)$CH_2$, C(O)NH, C(O) and NHC(O)NH.

In some embodiments, $R^3$ and $R^{3'}$ are independently selected from H and $C_{1-4}$alkyl, or when the atom to which $R^3$ is attached is $sp_2$ hybridized, $R^3$ is not present. In some embodiments, $R^3$ and $R^{3'}$ are independently selected from H and $CH_3$, or when the atom to which $R^3$ is attached is $sp_2$ hybridized, $R^3$ is not present.

In some embodiments, $R^4$ and $R^{4'}$ are independently selected from H, F, Cl, $CF_3$, $CH_3$, $CF_3O$ and $CH_3O$. In some embodiments, $R^4$ and $R^{4'}$ are independently selected from H, F, $CF_3$, $CH_3$, $CF_3O$ and $CH_3O$. In some embodiments at least one of $R^4$ and $R^{4'}$ is H. In some embodiments both of $R^4$ and $R^{4'}$ are H. In some embodiments neither of $R^4$ and $R^{4'}$ are H.

In some embodiments, A is selected from NH and $NCH_3$. In some embodiments, A is NH.

In some embodiments, A' is selected from O, NH and $NCH_3$ when m is 1 or 2. In some embodiments, A' is O or NH when m is 1 or 2. In some embodiments, A' is selected from NH and $NCH_3$ when m is 0. In some embodiments, A' is NH when m is 0.

In some embodiments, m is selected from 0 and 1. In some embodiments m is 0.

In some embodiments, m and p are both 0. In some embodiments, m and p are both 1. In some embodiments, m is 0 and p is 1.

In some embodiments, $Cy^2$ is selected from phenyl, $C_{3-6}$cycloalkyl, $C_{5-10}$heteroaryl and $C_{5-10}$heterocycloalkyl. In some embodiments, $Cy^2$ is selected from phenyl, naphthyl, cyclopropyl, cyclobutyl, cyclopentyl, cyclohexyl, 5-membered heteroaryl, 6-membered heteroaryl, 10-membered heteroaryl, 5-membered heterocycloalkyl and 6-membered heterocycloalkyl. In some embodiments, $Cy^2$ is selected from phenyl, naphthyl, cyclopropyl, cyclopentyl, cyclohexyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridinyl, pyrazinyl, pyrimidinyl, triazinyl, pyridazinyl, piperazinyl, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, hexamethylene oxide, naphthyl and quinolinyl. In some embodiments, $Cy^2$ is selected from phenyl, naphthyl, cyclohexyl, cyclopropyl, thienyl, piperidinyl, furyl, pyrrolyl, pyridinyl, pyrazinyl, pyrimidinyl, morpholinyl and quinolinyl. In some embodiments, $Cy^2$ is selected from phenyl, naphthyl, cyclohexyl, cyclopropyl, thienyl, piperidinyl, furyl, pyrrolyl, pyridinyl, pyrazinyl, pyrimidinyl and quinolinyl. In some embodiments, $Cy^2$ is selected from phenyl, thienyl, pyridinyl, piperidinyl, cyclopropyl, quinolinyl, morpholinyl and cyclohexyl. In some embodiments, $Cy^2$ is selected from phenyl, thienyl, pyridinyl, piperidinyl, cyclopropyl, quinolinyl and cyclohexyl.

In some embodiments, $Cy^1$ is unsubstituted or substituted one substituent selected from Cl, F, $NHCH_3$, $N(CH_3)_2$, $CF_3$, $CH_3$, $CH_3CH_2$, $(CH_3)_2CH_2$, $CH_3O$, $CH_3CH_2O$, $(CH_3)_2CH_2O$, $CF_3O$ and $CF_3O$. In some embodiments $Cy^1$ is unsubstituted.

In some embodiments, $Cy^2$ is unsubstituted or substituted with 1-3 substituents independently selected from Cl, F, phenyl, cyano, hydroxyl, $NH_2$, $NHCH_3$, $N(CH_3)_2$, $C_{1-4}$fluoroalkyl, $C_{1-4}$alkyl, $C_{1-4}$fluoroalkoxy and $C_{1-4}$alkoxy. In some embodiments, $Cy^2$ is unsubstituted or substituted with 1-2 substituents independently selected from phenyl, Cl, F, $NHCH_3$, $N(CH_3)_2$, $C_{1-3}$fluoroalkyl, $C_{1-3}$alkyl, $C_{1-3}$fluoroalkoxy and $C_{1-3}$alkoxy. In some embodiments, $Cy^2$ is unsubstituted or substituted with 1-2 substituents independently selected from Cl, F, $NHCH_3$, $N(CH_3)_2$, $C_{1-3}$fluoroalkyl, $C_{1-3}$alkyl, $C_{1-2}$fluoroalkoxy and $C_{1-3}$alkoxy. In some embodiments, $Cy^2$ is unsubstituted or substituted with 1-2 substituents independently selected from Cl, F, $NHCH_3$, $N(CH_3)_2$, $CF_3$, $CH_3$, $CH_3CH_2$, $(CH_3)_2CH_2$, $CH_3O$, $CH_3CH_2O$, $(CH_3)_2CH_2O$, $CF_3O$ and $CF_3O$.

In some embodiments, the compound of Formula I is selected from compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46 and I-47 as shown in Table 2, or a pharmaceutically acceptable salt, solvate and/or prodrug thereof.

In an embodiment, the compounds of the application are in the form of a pharmaceutically acceptable salt.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of nay of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels or powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide and other suitable gases. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application, including pharmaceutically acceptable salts, solvates and/or prodrugs thereof, is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

III. Methods and Uses of the Application

The compounds of the application have been shown to be selective inhibitors of hGGPPS activity. In some embodiments, compounds of the application are more selective in inhibiting hGGPPS activity that hFPPS activity. In some embodiments, additional (albeit weaker) activity in inhibiting hFPPS is not detrimental to the proposed therapeutic value of these compounds, but may be of an additional benefit.

The present application includes a method for inhibiting hGGPPS activity in a cell, either in a biological sample or in a patient, comprising administering an effective amount of one or more compounds of the application to the cell. The application also includes a use of one or more compounds of the application for inhibition of hGGPPS activity in a cell as well as a use of one or more compounds of the application for the preparation of a medicament for inhibition of hGGPPS activity in a cell. The application further includes one or more compounds of the application for use in inhibiting hGGPPS activity in a cell.

The present application includes a method for inhibiting geranylgeranylation of proteins in a cell, either in a biological sample or in a patient, comprising administering an effective amount of one or more compounds of the application to the cell. The application also includes a use of one or more compounds of the application for inhibition of geranylgeranylation in a cell as well as a use of one or more compounds of the application for the preparation of a medicament for inhibition of geranylgeranylation of proteins in a cell. The application further includes one or more compounds of the application for use in inhibiting geranylgeranylation of proteins in a cell.

As the compounds of the application have been shown to be capable of inhibiting hGGPPS activity, the compounds of the application are useful for treating diseases, disorders or conditions mediated by hGGPPS. Therefore the compounds of the present application are useful as medicaments. Accordingly, the present application includes a compound of the application for use as a medicament.

As the compounds of the application have been shown to also be capable of inhibiting hFPPS activity, in some embodiments, the compounds of the application are useful for treating diseases, disorders or conditions mediated by hFPPS. Therefore the compounds of the present application can block both farnesylation and geranylgeranylation of proteins and consequently, are useful as medicaments as such.

The present application also includes a method of treating a disease, disorder or condition mediated by hGGPPS comprising administering a therapeutically effective amount of one or more compounds of the application to a subject in need thereof.

The present application also includes a use of one or more compounds of the application for treatment of a disease, disorder or condition mediated by hGGPPS, or treatable by inhibition of geranylgeranylation of proteins, as well as a use of one or more compounds of the application for the preparation of a medicament for treatment of a disease, disorder or condition mediated by hGGPPS, or treatable by inhibition of geranylgeranylation of proteins. The application further includes one or more compounds of the application for use in treating a disease, disorder or condition mediated by hGGPPS, or treatable by inhibition of geranylgeranylation of proteins.

In an embodiment, the disease, disorder or condition mediated by hGGPPS, or treatable by inhibition of geranylgeranylation of proteins, is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation, reduced tumor mass, or reduce lytic bone disease, among others, in a subject in need of such treatment.

In another embodiment of the present application, the disease, disorder or condition mediated by hGGPPS, or treatable by inhibition of geranylgeranylation of proteins, is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In view of the inhibition of hFPPS activity by the compounds of the application, in another embodiment, the disease, disorder or condition is also one that is mediated by hFPPS, or treatable by inhibition of farnesylation. In an embodiment, this disease is cancer.

In some embodiments, the cancer is selected from hematological cancers such as multiple myeloma, chronic myelogenous leukemia and acute monocytic leukemia. Metastases of the aforementioned cancers can also be treated in accordance with the methods described herein.

In some embodiments, the cancer is selected from solid tumor cancers such as ovarian cancer, including those expressing multidrug resistance, pancreatic, fibrosarcoma, colorectal, brain and non-small cell lung cancers. Metastases of the aforementioned cancers can also be treated in accordance with the methods described herein.

In some embodiments, the disease, disorder or condition mediated by hGGPPS, or treatable by inhibition of geranylgeranylation of proteins, is osteoporosis or cancer-related lytic bone disease.

In an embodiment, the hGGPPS-mediated disease, disorder or condition is a disease, disorder or condition associated with an uncontrolled and/or abnormal cellular activity affected directly or indirectly by hGGPPS. In another embodiment, the uncontrolled and/or abnormal cellular activity that is affected directly or indirectly by hGGPPS is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

In an embodiment, the hFPPS-mediated disease, disorder or condition is a disease, disorder or condition associated with an uncontrolled and/or abnormal cellular activity affected directly or indirectly by hFPPS. In another embodiment, the uncontrolled and/or abnormal cellular activity that is affected directly or indirectly by hFPPS is proliferative activity in a cell.

The present application also includes a method of inhibiting uncontrolled and/or abnormal cellular activities mediated directly or indirectly by hGGPPS in a cell, either in a biological sample or in a subject, comprising administering an effective amount of one or more compounds of the application to the cell. The application also includes a use of one or more compounds of the application for inhibition of uncontrolled and/or abnormal cellular activities mediated directly or indirectly by hGGPPS in a cell as well as a use of one or more compounds of the application for the preparation of a medicament for inhibition of uncontrolled and/or abnormal cellular activities mediated directly or indirectly by hGGPPS in a cell. The application further includes one or more compounds of the application for use in inhibiting uncontrolled and/or abnormal cellular activities mediated directly or indirectly by hGGPPS in a cell.

The present application also includes a method of inhibiting uncontrolled and/or abnormal cellular activities mediated directly or indirectly by hFPPS in a cell, either in a biological sample or in a subject, comprising administering an effective amount of one or more compounds of the application to the cell. The application also includes a use of one or more compounds of the application for inhibition of uncontrolled and/or abnormal cellular activities mediated directly or indirectly by hFPPS in a cell as well as a use of one or more compounds of the application for the preparation of a medicament for inhibition of uncontrolled and/or abnormal cellular activities mediated directly or indirectly by hFPPS in a cell. The application further includes one or more compounds of the application for use in inhibiting uncontrolled and/or abnormal cellular activities mediated directly or indirectly by hFPPS in a cell.

The present application also includes a method of treating a disease, disorder or condition that is mediated by hGGPPS, or treatable by inhibition of geranylgeranylation of proteins, comprising administering a therapeutically effective amount of one or more compounds of the application in combination with another known agent useful for treatment of a disease, disorder or condition mediated by hGGPPS, or treatable by inhibition of geranylgeranylation, to a subject in need thereof. The present application also includes a use of one or more compounds of the application in combination with a known agent useful for treatment of a disease, disorder or condition mediated by hGGPPS, or treatable by inhibition of geranylgeranylation, for treatment of a disease, disorder or condition mediated by hGGPPS.

The present application also includes a method of treating a disease, disorder or condition that is mediated by hFPPS, or treatable by inhibition of farnesylation of proteins, comprising administering a therapeutically effective amount of one or more compounds of the application in combination with another known agent useful for treatment of a disease, disorder or condition mediated by hFPPS, or treatable by inhibition of farnesylation, to a subject in need thereof. The present application also includes a use of one or more compounds of the application in combination with a known agent useful for treatment of a disease, disorder or condition mediated by hFPPS, or treatable by inhibition of farnesylation, for treatment of a disease, disorder or condition mediated by hFPPS.

In a further embodiment, the disease, disorder or condition mediated hGGPPS, or treatable by inhibition of geranylgeranylation of proteins, and/or that is mediated by hFPPS, or treatable by inhibition of farnesylation of proteins, is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

In another embodiment of the present application, the disease, disorder or condition that has been implicated with upregulation of hGGPPS activity, and consequently, may be treatable by inhibition of geranylgeranylation, is Alzheimer's Disease. Accordingly, the present application also includes a method of treating taupathies that are associated with neurodegeneration, such as Alzheimer's Disease, comprising administering a therapeutically effective amount of one or more compounds of the application to a subject in need thereof. The present application also includes a use of one or more compounds of the application for the treatment of taupathies that are associated with neurodegeneration, such as Alzheimer's Disease, as well as a use of one or more compounds of the application for the preparation of a medicament for the treatment of taupathies that are associated with neurodegeneration, such as Alzheimer's Disease. The application further includes one or more compounds of the application for use in the treatment of taupathies that are associated with neurodegeneration, such as Alzheimer's Disease. In an embodiment, the compound is administered or used for the prevention of neurofibrillary tangles induced by high levels of phosphorylated tau protein in the brain which is strongly associated with Alzheimer's Disease in a subject such as a mammal having a predisposition for Alzheimer's Disease.

A compound of the application is either used alone or in combination with other known agents useful for treating diseases, disorders or conditions that are mediated by hGGPPS, and those that are treatable with an hGGPPS inhibitor and/or with other known agents useful for treating diseases, disorders or conditions that are mediated by hFPPS, and those that are treatable with an hFPPS inhibitor. When used in combination with other agents useful in treating diseases, disorders or conditions mediated by hGGPPS inhibition and/or hFPPS inhibition, it is an embodiment that a compound of the application is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent, and a pharmaceutically acceptable carrier.

Thus the methods of the present application are applicable to both human therapy and veterinary applications. In an embodiment, the subject is a mammal. In another embodiment, the subject is human.

The dosage of a compound of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound of the application is administered initially in a suitable dosage that is adjusted as required, depending on the clinical response. Dosages will generally be selected to maintain a serum level of the compound of the application from about 0.01 μg/cc to about 1000 μg/cc, or about 0.1 μg/cc to about 100 μg/cc. As a representative example, oral dosages of one or more compounds of the application will range between about 1 mg per day to about 2000 mg per day for an adult, about 1 mg per day to about 1000 mg per day, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. In an embodiment of the application, compositions are formulated for oral administration and the one or more compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In embodiments of the application the one or more compounds of the application are administered in a single daily, weekly or monthly dose or the total daily dose is divided into two, three or four daily doses.

In the above, the term "a compound" also includes embodiments wherein one or more compounds are referenced.

IV. Methods of Preparing Compounds of the Application

Compounds of the present application are prepared by various synthetic processes. The choice of particular structural features and/or substituents may influence the selection of one process over another. The selection of a particular process to prepare a given compound of the application is within the purview of the person of skill in the art. Some starting materials for preparing compounds of the present application are available from commercial chemical sources. Other starting materials, for example as described below, are readily prepared from available precursors using straightforward transformations that are well known in the art.

In some embodiments of the application, compounds of Formula I that are based on a thieno[2,3-d]pyrimidin-4-amine scaffold, wherein X is NH and $R^1$ is a bisphosphonate or bisphosphonate ester, are prepared as shown in Schemes 1, 6 and 7. In some embodiments, the thiophene intermediate 1 is prepared from the commercially available dimer of mercaptoacetaldehyde, 1,4-dithiane-2,5-diol or from an aldehyde as previously reported [see for example: (a) Leung, et al. J. Med. Chem. 2013, 56, 7939-7950. (b) Leung, et al Bioorg. Med. Chem. 2013, 21, 2229-2240. (c) Gao, et al. Bioorg. Med. Chem. Lett. 2013, 23, 1953-1956]. In some embodiments, as shown in Scheme 1, the 2-amino-3-cyanothiophene core 1 is elaborated to substituted 4a,7a-dihydrothieno[2,3-d]pyrimidin-4-amine core of general structure 3 via direct cyclization with various aryl and or heteroaryl nitriles in the presence of a base (Chen, et. al. Synthesis 2010, 14, 2413-2418). In some embodiments, as shown in Scheme 1, intermediate 1 is cyclized to the thioether intermediate 2 having a methyl thioether moiety at the C-2 of the pyrimidine ring, by condensing 1 with methyl thiocyanate under acidic conditions (Barbay, et. al. WO 2010/045006 A1). In further embodiments, upon introduction of the bisphosphonate tetraesters (i.e. conversion of 2 to 4; $R^a$=SMe), the thioether intermediate 4 is suitable for the Liebeskind-Srogl cross-coupling reaction (Liebeskind and Srogl Org. Lett., 2002, 4, 979-981; Barbay, et. al. WO 2010/045006 A1) with various boronic acids to give compounds 5 with significant structural diversity at $R^a$, including various aryl and heteroaryl groups. In some embodiments, intermediates 5 include analogs where $R^a$ is an aromatic or heteroaromatic group with a niro substituent, for example a nitrophenyl (e.g. 5a in Scheme 6) or an aryl, heteroaryl or other heterocycle with a carboxylic acid substituent (e.g. 5b in Scheme 6). In some embodiments, the latter compounds are further elaborated to analogs such as compounds having an amide, sulfonamide or urea linker L between the two groups $Cy^1$ and $Cy^2$ as shown in Schemes 6 and 7. In some embodiments, the thioether moiety of intermediates 2 can be oxidized to the corresponding methylsulfonyl intermediates with m-CPBA, followed by nucleophic displacement of the methylsulfonyl moiety by $S_NAr$ to give compounds with general formula 7, which can be further elaborated to hGGPPS inhibitors with general structure 8, as shown in Scheme 1. It would be known to those skilled in the art of organic synthesis that the $R^e$ moiety of inhibitors 8 could also be prepared in several steps, starting from an intermediate of 7 having $R^e$ as an appropriate functional group, including, but not limited to an amine, a carboxylic acid, an acid chloride, a halogen or an alcohol, which can be further elaborated using similar synthetic methodologies for example to those shown in Schemes 6 and 7 for the conversion of intermediates 5a, 5b and 5c of Scheme 6 to the final inhibitors, for example, analogs Ia, Ib, Ic and Id. In Schemes 1, 5 and 6, the variables Q and W represent substituted or unsubstituted carbon or nitrogen, or a heteroatom selected from O and S, q is 0, 1, 2, 3 or 4 and $R^a$-$R^e$ represent various functional groups that are found in Formula I or can be converted using known methods, to functional groups found in Formula I.

Scheme 1: Exemplary reaction conditions for the synthesis of compounds with the 4a,7a-dihydrothieno[2,3-d]pyrimidin-4-amine core.

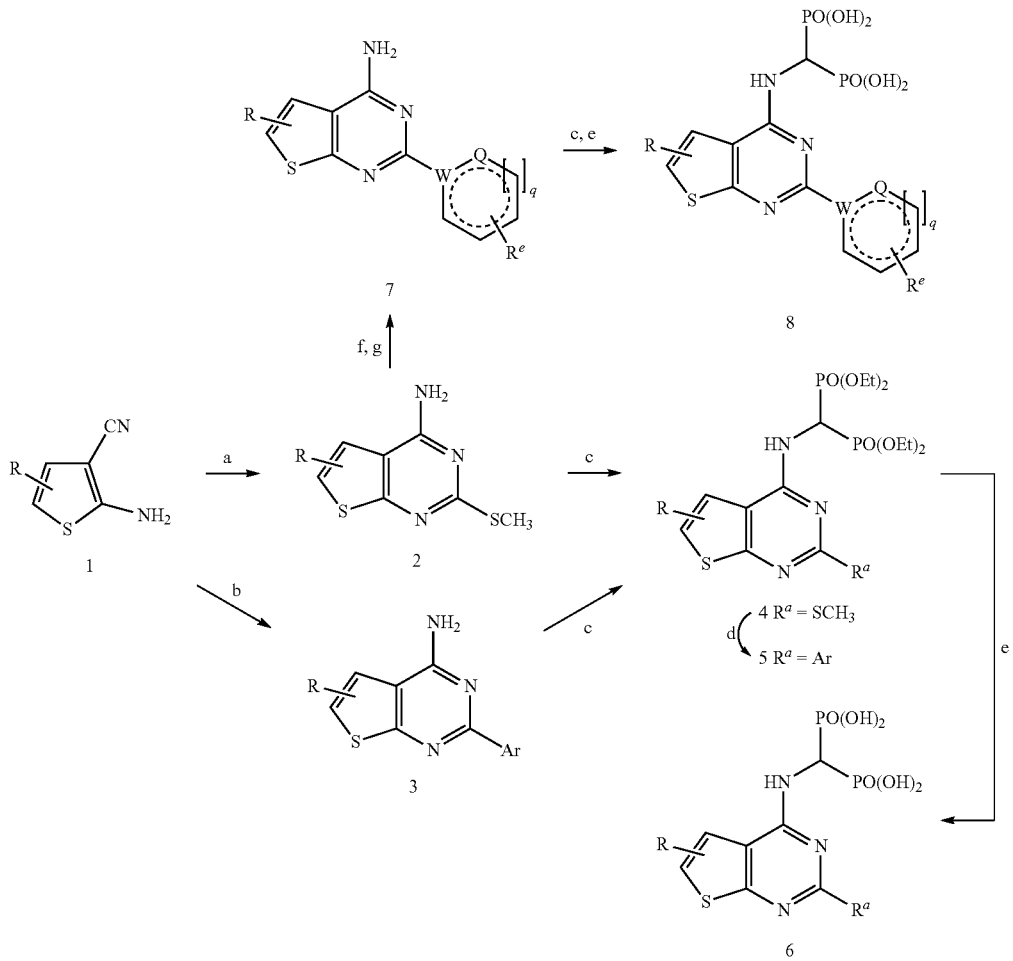

Reaction conditions: (a) methyl thiocyanate, HCl, 70° C., 60%-80%; (b) aromatic nitrile, t-BuOK, iPrOH, μW, 70-80° C., ~27%-64%; (c) diethyl phosphite, triethyl orthoformate, dry toluene, 115°-130° C., 40%-80%; (d) aryl boronic acid, CuTC, Pd(dppf)Cl$_2$•CH$_2$Cl$_2$, dry dioxane, 50° C., ~80%; (e) TMSBr/MeOH, rt, ~60% to quantitative; (f) m-CPBA, DCM, 80-90%; S$_N$Ar reaction with a nucleophile (e.g. an amine), DMSO, 100-120° C., ~75%

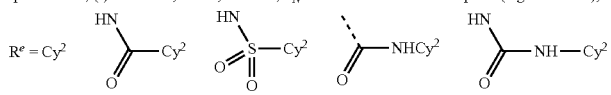

It would be known to those skilled in the art of organic synthesis that similar synthetic methodologies to those described in Schemes 1, 6 and 7 for the preparation of thieno[2,3-d]pyrimidine-based compounds Formula I can also be used to prepare analogs with a thieno[3,2-d]pyrimidine-based core. Examples of the synthesis of the building blocks for the preparation of these compounds are shown in Scheme 2. In Scheme 2, the variables Q and W represent substituted or unsubstituted carbon or nitrogen, or a heteroatom selected from O and S, q is 0, 1, 2, 3 or 4 and R$^e$ represents various functional groups that are found in Formula I or can be converted using known methods, to functional groups found in Formula I.

Scheme 2: Exemplary reaction conditions for the synthesis of compounds with the 4a,7a-dihydrothieno[3,2-d]pyrimidin-4-amine-core.

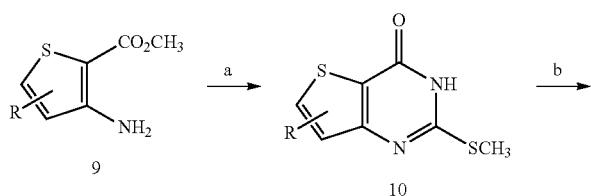

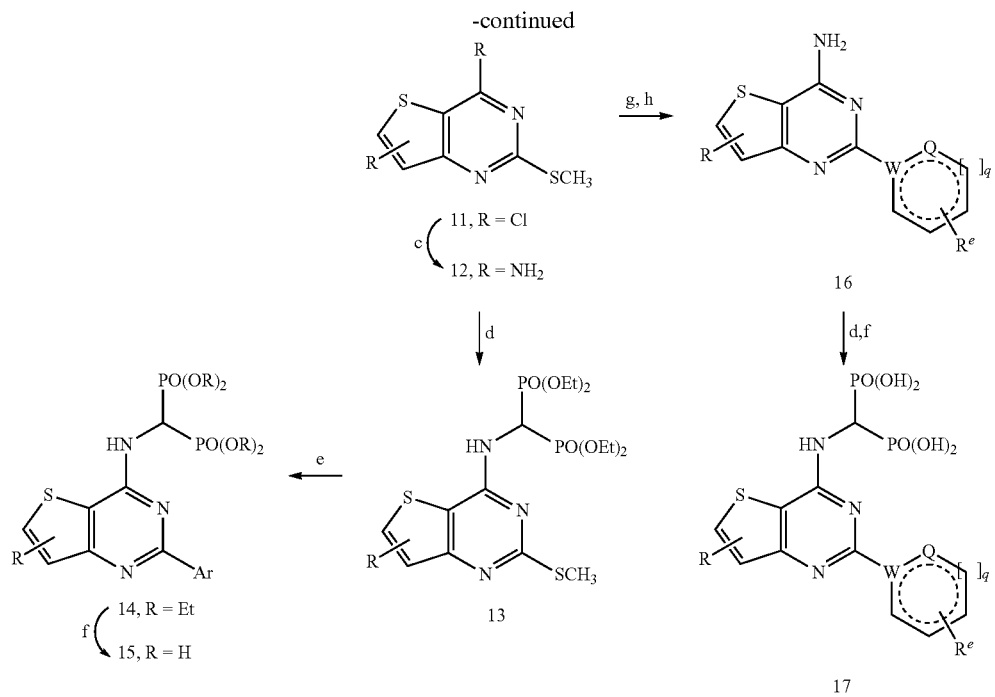

Reaction conditions: (a) methyl thiocyanate, 4M HCl, 90° C., ~90%; (b) phosphorus oxychloride, 106° C., ~70%; (c) NH₄OH, 90° C., ~90%; (d) diethyl phosphite, triethyl orthoformate, dry toluene, 130° C., ~55%: (e) aryl boronic acid, CuTC, Pd(dba)₃, ZnOAc₂, dry dioxane, 80° C., ~55%; (f) TMSBr/MeOH, rt, ~60%. (g) m-CPBA, DCM, ~85%; (h) S$_N$Ar reaction with a nucleophile (e.g. an amine), DMSO, 100-120° C., ~75%

It would be known to those skilled in the art of organic synthesis that similar synthetic methodologies to those described in Schemes 1, 2, 6 and 7 for the preparation of thienopyrimidine-based compounds of Formula I can also be used to prepare analogs that arm thiazolopyrimidine-based compounds of Formula I. Examples of the synthesis of building blocks for the preparation of thiazolo[5,4-d]pyrimidine-based compounds are shown in Scheme 3.

Scheme 3: Exemplary reaction conditions for the synthesis of compounds with the thiazolo[5,4-d]pyrimidin-7-amine core.

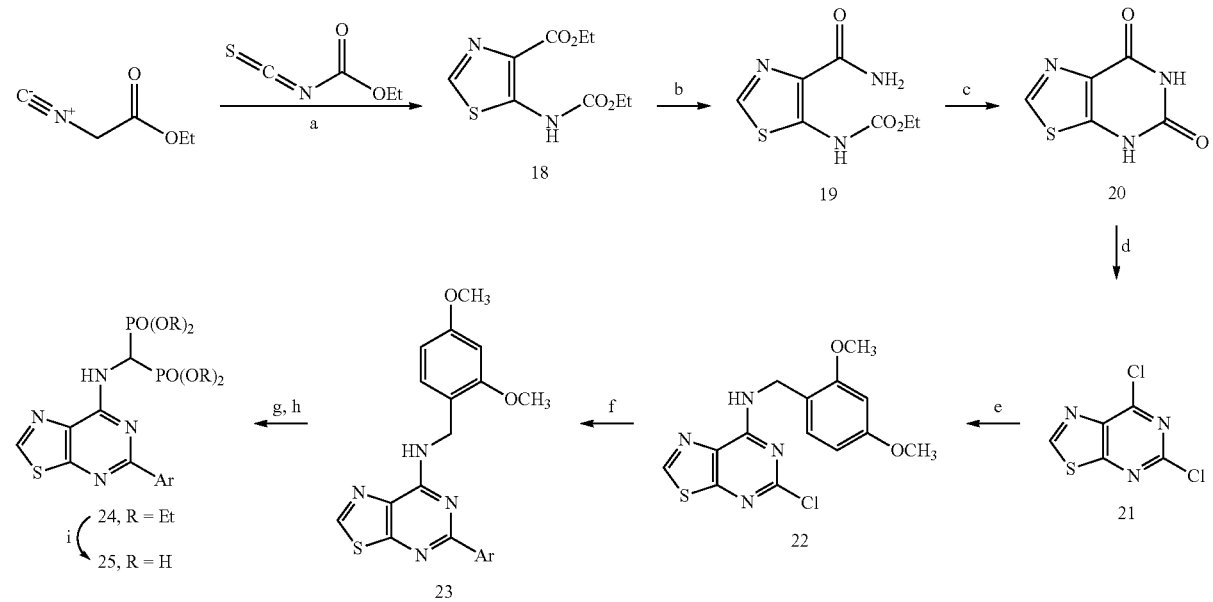

Reaction conditions: (a) t-BuOK, anhydrous THF, -35° C. to 0° C., ~75%; (b) NH₄OH, 40° C. to 80° C., ~70%; (c) t-BuOK, N,N-dimethylacetamide, 100° C., ~85%; (d) POCl₃, DIPEA, reflux, 60%; (e) dimethoxybenzylamine, DIPEA, DMSO, 22° C., ~70%; (f) aryl boronic acid, Pd(PPh₃)₄, KF, CH₃OH/dioxane (2:1), 90° C., ~90%; (g) TFA in CH₂Cl₂, 22° C., ~75%; (h) diethyl phosphite, triethyl orthoformate, dry toluene, 130° C., ~30-50%; (i) TMSBr/MeOH, rt, 50-80%.

It would be known to those skilled in the art of organic synthesis that similar synthetic methodologies to those described in Schemes 1, 2, 3, 6 and 7 for the preparation of thienopyrimidine-based and thiazolopyrimidine-based compounds of Formula I can also be used to prepare purine-based compounds of Formula I. Examples of the synthesis of building blocks for the preparation of these compounds are shown in Scheme 4.

Scheme 4: Exemplary reaction conditions for the synthesis of compounds with the 9H-purin-6-amine core.

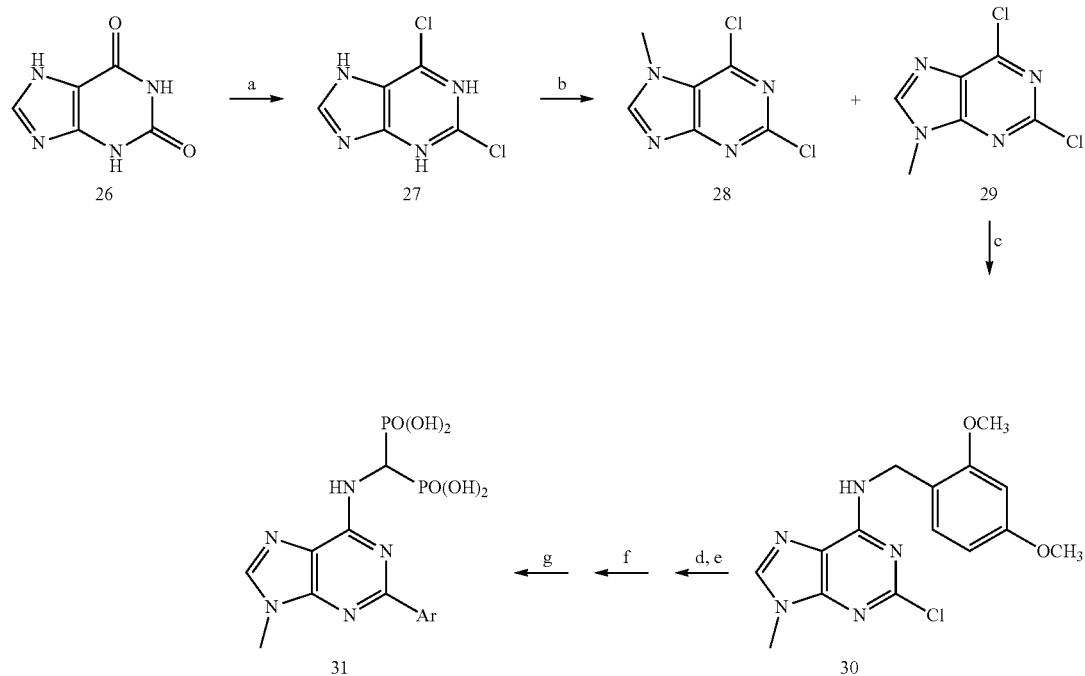

Reaction conditions: (a) POCl₃, DBU, reflux, ~35%; (b) CH₃I, K₂CO₃, acetone, 22° C., 27% of 28, 65% of 29; (c) dimethoxybenzylamine, DIPEA, DMF, 22° C., 90%; (d) aryl or heteroaryl boronic acid, Pd(PPh₃)₄, KF, CH₃OH/dioxane (2:1), 90° C., 50-90%; (e) TFA in CH₂Cl₂, 22° C., ~75%; (f) diethyl phosphite, triethyl orthoformate, dry toluene, 130° C., ~30-50%; (g) TMSBr/MeOH, rt, 50-80%.

Similar synthetic methodologies to those described in the Schemes 1, 2, 3, 4, 6 and 7 for the preparation of thienopyrimidine-based, thiazolopyrimidine-based and purine-based compounds of Formula I can also be used to prepare pyrrolopyrimidine-based compounds of Formula I. As an example, the synthesis of building blocks for the preparation of 7H-pyrrolo[2,3-d]pyrimidine-based inhibitors is shown in Scheme 5.

Scheme 5: Exemplary reaction conditions for the synthesis of compounds with the 7H-pyrrolo[2,3-d]pyrimidin-4-amine core.

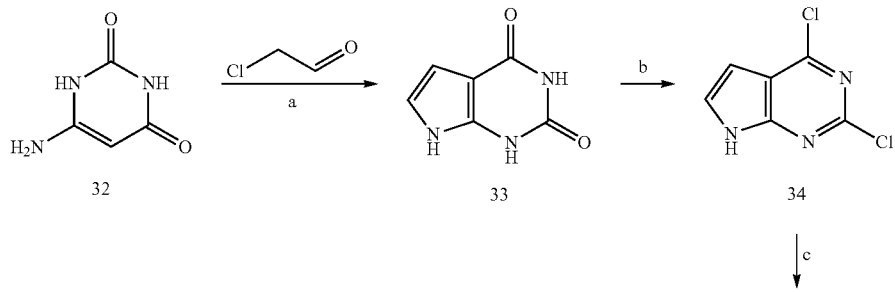

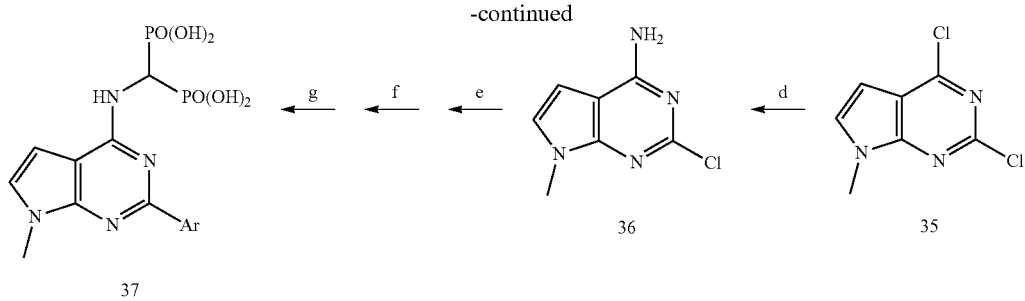

Reaction conditions: (a) NaOAc, H₂O, 70° C., 80-90%; (b) POCl₃, DIPEA, toluene, 70-106° C., ~50% (used crude in the subsequent step); (c) NaH, CH₃I, CH₃CN, 22° C., ~60%; (d) 30% NH₄OHaq., dioxane, 90° C., ~90%; (e) aryl boronic acid, Pd(PPh₃)₄, KF, CH₃OH/dioxane (2:1), 90° C., ~90%; (f) diethyl phosphite, triethyl orthoformate, dry toluene, 130° C., ~30-50%; (g) TMSBr/MeOH, rt, 50-80%.

Synthetic methodologies for the preparation of furopyrimidine-based compounds of Formula I starting from the dichloro intermediates that are structurally equivalent to compound 34 (in Scheme 5), but where the nitrogen of the 5-membered pyrrole ring is replaced by an oxygen atom, are known (see for example WO 2008/073785 and Roecker et al. *Biorg. Med. Chem. Lett.* 2014, 24, 2079-2085). These intermediates can be further elaborated to final compounds of Formula I using the synthetic methodologies described in the Schemes 4, 5, 6 and 7. Similarly, the synthesis of oxazolopyrimidiners can be achieved using previously reported synthetic intermediates. For example an intermediate such as the 5,7-dichlorooxazolo[5,4-d]pyrimidine 37 shown in Scheme 7 (for an example of the synthesis, see WO 2009/013545) can be further elaborated to final compound of Formula I using the synthetic methodologies described in Schemes 4, 5, 6 and 7. In some embodiments, compounds of Formula I are synthesized, for example through direct connection of two groups $Cy^1$ and $Cy^2$ or the incorporation of a linker between group $Cy^1$ and $Cy^2$, which in some embodiments is a direct bond, methylene, an amide, a reversed amide, a sulfonamide, or a urea (Scheme 7). For example, in some embodiments, the nitro group of 5a in Scheme 6 is first reduced to the amine using tin (II) chloride and the aniline product 5d is then coupled with an acyl chloride or a carboxylic acid using standard peptide chemistry to give analogs with general structure Ic, or with a sulfonyl chloride to give analogs Id, or with an isocyanate to give analogs with a urea linker L. Similarly, in some embodiments compounds of Formula I are prepared from the carbocylic acid 5b (Scheme 6) or via Liebeskind-Srogl cross-coupling reaction between 4 (Scheme 1) and appropriate boronic acid to give eventually the reversed amide derivatives Ib. In some embodiments, compounds of Formula I are prepared via Pd-catalyzed cross-coupling reactions with the aryl halides (5c, Scheme 6) to give biaryl derivatives Ia.

Scheme 6:

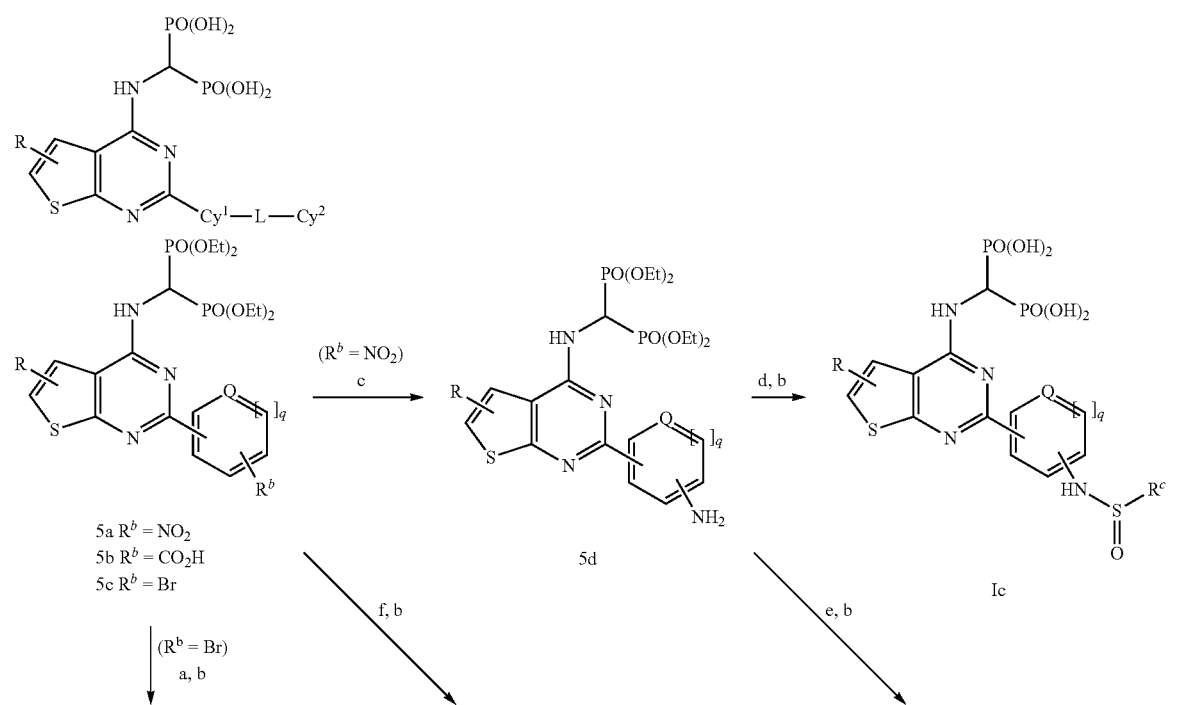

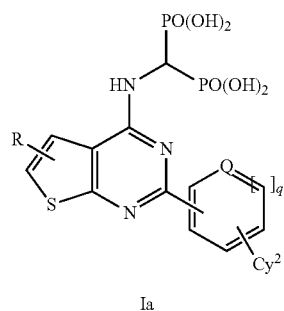

Ia

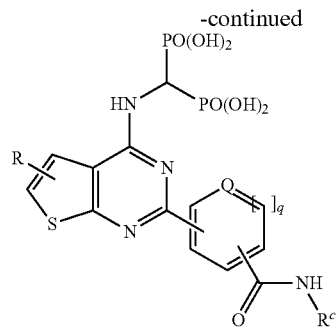

Ib

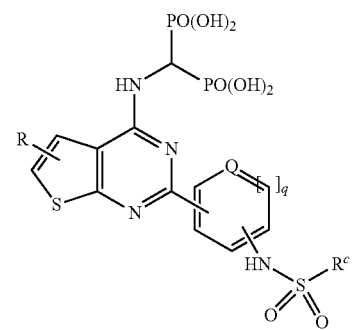

Id

Exemplary reaction conditions: (a) aryl boronic acid, KF, Pd(PPh₃)₄, MeOH, μW, 120° C., 82%; (b) TMSBr then MeOH, rt, ~60% to quantitative; (c) SnCl₂•2H₂O, EtOH, 80° C., >80%; (d) acyl chloride, Et₃N; dry DCM, 0° C. to rt or a carboxylic acid, DIPEA, HBTU, dry DMF, rt, 60% to quant., or an isocyanate, Et₃N, dry DCM, 0° C. to rt, 71%; (e) sulfonyl chloride, pyridine, dry DCM, 0° C. to rt, 70% to quant.; (f) amine, DIPEA, HBTU, dry DMF, rt, 60-85%.

In some embodiments, compounds of Formula I are thiazolo[5,4-d]pyrimidine-based, 9H-purine-based and 7H-pyrrolo[2,3-d]pyrimidine-based bisphosphonates prepared using protocols similar to those described above from the respective dichloro intermediates 21 (Scheme 3), 27 (Scheme 4) and 34 (Scheme 5) and briefly summarized in Scheme 7.

Scheme 7:

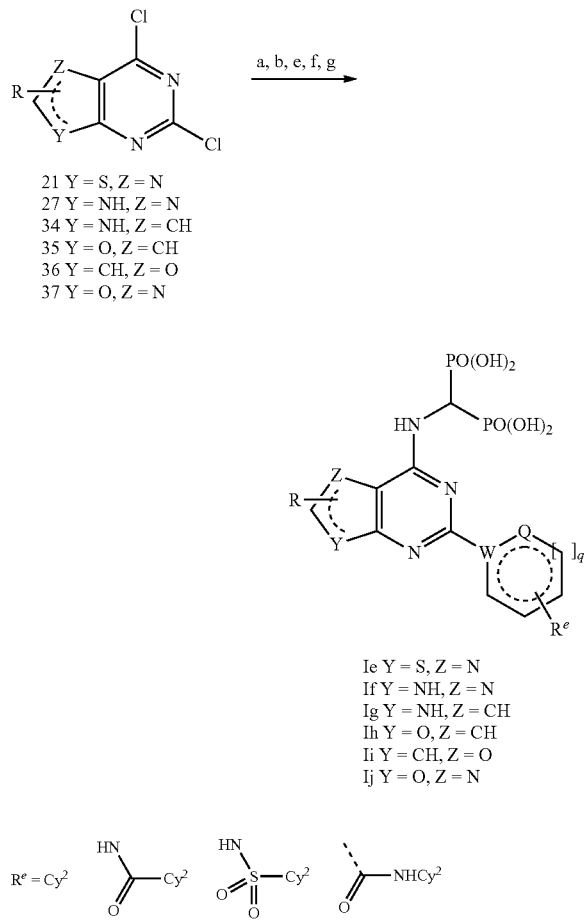

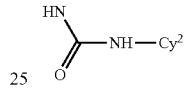

Exemplary reaction conditions are: (a) dimethoxybenzylamine; (b) Metal-mediated cross coupling, such as Suzuki, Buckwald-Hartwig or Sonogashira cross-coupling, S$_N$Ar is also possible with a strong nucleophile; (c) TFA; (d) diethyl phosphite, triethyl orthoformate) TMSBr/MeOH In Schemes 6 and 7, the variables Q and W represent substituted or unsubstituted carbon or nitrogen, or a heteroatom selected from O and S, q is 0, 1, 2, 3 or 4 and $R^e$ represents various functional groups that are found in Formula I or can be converted using known methods, to functional groups found in Formula I.

A person skilled in the art of organic synthesis would understand that the procedures summarized in Schemes 1-7, for the preparation of Formula I compounds that are thienopyrimidine-, thiazolopyrimidine-, purine-, pyrrolopyrimidine-, furopyrimidine- or oxazolopyrimidine-based compounds with general formulas Ia, Ib, Ic, Id, Ie, If, Ig, Ih, Ii and Ij can be prepared from other key intermediates that can be accessed from published procedures. In some embodiments the main starting materials are obtained from a commercial source or are prepared using the literature protocols provided in the synthesis of specific Examples below. In some embodiments, compounds of formula 21, 27, 34, 35 and 37 can be further elaborated to Examples Ie to Ij via first nucleophilic aromatic substitution ($S_N$Ar) reactions of the chloride at the C-4 carbon of the pyrimidine ring with ammonia or a suitable protected amine to give intermediates such as 22 (in Scheme 3), 30 (in Scheme 4), 36 (in Scheme 5), followed by metal-catalyzed cross-coupling reactions or $S_N$Ar displacement of the C-2 chloro moiety. For instance, a variety of aryl- or heteroaryl-boronic acids are reacted with intermediates 22, 30 or 36 via Suzuki cross-coupling reaction. Additionally, in some embodiments, Buchwald-Hartwig amination is done to prepare a diverse library of compounds varied at the position indicated. Other metal-mediated cross coupling reactions that would be known to those skilled in organic synthesis can also be used to increase the structural diversity of compounds with general structure of Formula I.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (4$^{th}$ Edition, 2007). It is also to be understood that a transformation of a group or substituent into another group or substituent by chemical manipulation is conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

All process/method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The following non-limiting examples are illustrative of the present application:

EXAMPLES

Chemicals and solvents were purchased from commercial suppliers and used without further purification. Normal phase column chromatography on silica gel was performed using a CombiFlash instrument using the solvent gradient, as indicated. Reverse phase preparative HPLC was carried out using a Waters Atlantis Prep T3 OBD C18 5 μm 19×50 mm column; Solvent A: $H_2O$, 0.1% formic acid; Solvent B: $CH_3CN$, 0.1% formic acid; Mobile phase: gradient from 95% A and 5% B to 5% A and 95% B in 17 min acquisition time; flow rate: 1 mL/min. The homogeneity of final compounds was confirmed to be ≥95% by reversed-phase HPLC using a Waters ALLIANCE® instrument (e2695 with 2489 UV detector, 3100 mass spectrometer, C18 5 μm column): Solvent A: $H_2O$, 0.1% formic acid; Solvent B: $CH_3CN$, 0.1% formic acid; Mobile phase: linear gradient from 95% A and 5% B to 0% A and 100% B in 13 mins. Key compounds were fully characterized by $^1H$, $^{13}C$, $^{31}P$ NMR and MS and HRMS. Chemical shifts (δ) are reported in ppm relative to the internal deuterated solvent. The NMR spectra of all final bisphosphonate compounds were acquired in $D_2O$ (either after conversion to their corresponding trisodium salt or by addition of ~2% $ND_4OD$). In some cases, the Cα to the bisphosphonate was broad and overlapped with the solvent peak, as confirmed by HSQC. The high resolution MS spectra of final products were recorded using electrospray ionization (ESI$^{+/-}$) and Fourier transform ion cyclotron resonance mass analyzer (FTMS).

Example 1: Preparation of Compounds

Synthesis of 2-(methylthio)thieno[2,3-d]pyrimidin-4-amine (2, R=H) (Scheme 1)

2-aminothiophene-3-carbonitrile (1, R=H; 1.0 eq) was added to HCl in dioxane (4M; 6.0 eq), followed by methyl thiocyanate (1.0 eq). The resulting suspension was heated to 70° C. in a sealed pressure tube for 24 h. The mixture was allowed to cool to rt and the resulting green precipitate was collected by vacuum filtration. The solid was dissolved in EtOAc and washed with saturated aqueous $NaHCO_3$. The layers were separated and the aqueous phase was extracted further with EtOAc. The organic extracts were combined, washed with brine, dried over $Na_2SO_4$, and concentrated in vacuo. Product was obtained as a light brown solid (typical isolated yield was between 60%-80%) and used in the next step without further purification. $^1H$ NMR (500 MHz, DMSO-d$_6$) δ 7.55 (br_s, 2H), 7.47 (d, J=5.9 Hz, 1H), 7.36 (d, J=5.9 Hz, 1H), 2.46 (s, 3H). $^{13}C$ NMR (126 MHz, DMSO-d$_6$) δ 167.5, 166.5, 158.3, 120.7, 120.2, 113.4, 13.8. MS [ESI$^+$] m/z: 198.0 [M+H]$^+$.

Tetraethyl (((2-(methylthio)thieno[2,3-d]pyrimidin-4-yl)amino)methylene)bis(phosphonate) (4, R=H) (Scheme 1)

A pressure vessel charged with 2-(methylthio)thieno[2,3-d]pyrimidin-4-amine (2, R=H; 1.0 eq) in dry toluene (1.0 M) was added with diethyl phosphite (7.0 eq) and triethyl orthoformate (1.7 eq). The mixture was heated at 130° C. for 40 h (monitored by TLC and LC-MS). It was then cooled down to rt and concentrated in vacuo. Crude product was purified by silica gel column chromatography using a CombiFlash instrument (product eluted at 20% MeOH in EtOAc). Product was isolated as a brown solid (40% yield). $^1H$ NMR (500 MHz, DMSO-d$_6$) δ 8.70 (d, J=9.7 Hz, —NH), 7.97 (d, J=6.0 Hz, 1H), 7.45 (d, J=6.0 Hz, 1H), 5.70 (td, J=23.6, 9.7 Hz, 1H), 4.14-4.02 (m, 8H), 2.50 (s, 3H), 1.22-1.12 (m, 12H). $^{31}P$ NMR (203 MHz, DMSO-d$_6$) δ 16.77 (s). $^{13}C$ NMR (126 MHz, DMSO-d6) δ 167.3, 165.4, 155.12 (t, J=4.1 Hz), 121.1, 120.1, 113.6, 62.9-62.7 (m), 44.4 (t, J=147.3 Hz), 16.2-16.1 (m), 13.5. MS [ESI$^+$] m/z: 484.1 [M+H]$^+$.

General Protocol for the Liebeskind-Srogl Cross-Coupling Reaction Shown in Schemes 1 and 2:

The procedure was based on literature with slight modifications (Barbay, J. K. et al. WO 2010/045006; Liebeskind, L. S.; Srogl, J. *Org. Lett.* 2002, 4, 979-981). Therefore tetraethyl (((2-(methylthio)thieno[2,3-d]pyrimidin-4-yl) amino)methylene)bis(phosphonate) (intermediate 4, 882 mg, 1.8 mmol), aryl boronic acid (4.6 mmol; Note: boronic acids were obtained commercially or prepared using established methods), CuTC (1.04 g, 5.5 mmol) and Pd(dppf) $Cl_2CH_2Cl_2$ (149 mg, 0.18 mmol) were charged into an oven-dried round bottom flask. The flask was evacuated and purged with Ar, followed by addition of dry dioxane (10.0 mL). The flask was sealed and heated at 50° C. for 4-16 h (under Ar balloon; monitored by TLC and LC-MS). The reaction mixture was cooled to RT, diluted with EtOAc, and filtered through celite. The filtrate was collected and washed with 10% aqueous $NH_4OH$ (thrice), followed by brine. The combined organic extracts were dried over $Na_2SO_4$ and concentrated in vacuo. Crude product was purified by silica gel column chromatography with a gradient from 25% EtOAc in hexanes to 100% EtOAc and then to 20% MeOH in EtOAc. Product typically elutes between 10%-20% MeOH in EtOAc. Typical isolated yield was ~80-85%.

Tetraethyl (((2-(3-nitrophenyl)thieno[2,3-d]pyrimidin-4-yl)amino)methylene)bis(phosphonate) (5a, $R^a$=3-nitrophenyl, R=H) (Scheme 6)

Tetraethyl (((2-(methylthio)thieno[2,3-d]pyrimidin-4-yl)amino)methylene)bis(phosphonate)(4, $R^a$=SMe, R=H; 1.0 eq), 3-nitrophenylboronic acid (2.5 eq), CuTC (3.0 eq) and Pd(dppf)$Cl_2 \cdot CH_2Cl_2$ (0.10 eq) were charged into an oven-dried round bottom flask. The flask was evacuated and purged with Ar, followed by addition of dry dioxane (5.5 mL per 1.0 mmol of 4). The flask was sealed and heated at 50° C. for 4 h (under Ar balloon). The reaction mixture was cooled to rt, diluted with EtOAc, and filtered through celite. The filtrate was collected and washed with 10% aqueous $NH_4OH$ (thrice), followed by brine. The combined organic extracts were dried over $Na_2SO_4$ and concentrated in vacuo. Crude product was purified by silica gel column chromatography (product eluted at 15% MeOH in EtOAc). Product was isolated as light brown solid (80% yield). $^1H$ NMR (500 MHz, DMSO-$d_6$) δ 9.12 (t, J=1.9 Hz, 1H), 8.85 (d, J=9.6 Hz, —NH), 8.80 (d, J=7.9 Hz, 1H), 8.35 (ddd, J=8.2, 2.4, 0.9 Hz, 1H), 8.14 (d, J=6.0 Hz, 1H), 7.84 (t, J=8.0 Hz, 1H), 7.72 (d, J=6.0 Hz, 1H), 5.99 (td, J=23.5, 9.6 Hz, 1H), 4.19-4.07 (m, 8H), 1.22-1.11 (m, 12H). $^{31}P$ NMR (203 MHz, DMSO-$d_6$) δ 16.9. $^{13}C$ NMR (126 MHz, DMSO-d6) δ 167.8, 156.5 (t, J=4.0 Hz), 156.4, 148.7, 139.6, 134.1, 130.8, 125.3, 124.9, 122.4, 120.8, 116.4, 63.4-63.2 (m), 45.0 (t, J=147.2 Hz), 16.7-16.6 (m). MS [$ESI^+$] m/z: 559.1 [M+H]$^+$.

General Protocol for Amide Bond Formation Using Either Method A or Method B:

Method A: To a stirring solution of 5d in Scheme 6, for example, tetraethyl (((2-(3-aminophenyl)thieno[2,3-d]pyrimidin-4-yl)amino)methylene)bis(phosphonate) (0.15 mmol) in dry DCM (1.5 mL) at 0° C. was added dry $Et_3N$ (0.45 mmol). The acid chloride (Ar—COCl) (0.18 mmol) was then added dropwise. The solution was stirred and allowed to warm to RT (reaction progress was monitored by TLC and/or LC-MS). Once complete (typically, after ~1 h), the reaction was poured into saturated aqueous $NaHCO_3$ solution and extracted with EtOAc (twice), washed with brine, dried over $Na_2SO_4$ and concentrated under vacuum. Crude product was purified by silica gel column chromatography with a gradient from 25% EtOAc in hexanes to 100% EtOAc and then to 20% MeOH in EtOAc. Product typically elutes between 10%-20% MeOH in EtOAc. Isolated yield was typically 75% to quantitative. Alternatively, aryl carboxylic acid (instead of an acid chloride) was used in the reaction using HATU or HBTU as the coupling reagent following a similar method described for Method B.

Method B: To the mixture of 5b, in Scheme 6, for example, 3-(4-((bis(diethoxyphosphoryl)methyl)amino)thieno[2,3-d]pyrimidin-2-yl)benzoic acid, (0.09 mmol) and amine (Ar—$NH_2$) (0.1 mmol) in dry DMF (2.0 mL) was added DIPEA (0.18 mmol) followed by HBTU (0.1 mmol). The solution was stirred at RT until completion (typically after ~1-2 h). Brine was added to the reaction mixture and was extracted with EtOAc. The organic phase was washed with sat. $NH_4Cl$ solution, brine, dried over $Na_2SO$, and concentrated in vacuo. Crude product was purified by silica-gel column chromatography as described for Method A, above. Isolated yield was typically 60-80%.

3-(4-((bis(diethoxyphosphoryl)methyl)amino)thieno[2,3-d]pyrimidin-2-yl)benzoic acid (5b, Scheme 2)

Step 1: Intermediate 4 was reacted with (3-((benzyloxy)carbonyl)phenyl)boronic acid using the general protocol for the Liebesking-Srogl cross coupling reaction described above to obtain intermediates such as the benzyl 3-(4-((bis(diethoxyphosphoryl)methyl)amino)thieno[2,3-d]pyrimidin-2-yl)benzoate intermediate, which was isolated as a yellow solid. $^1H$ NMR (500 MHz, $CD_3OD$) δ9.09 (s, 1H), 8.66 (d, J=7.8 Hz, 1H), 8.14 (dd, J=7.7, 1.1 Hz, 1H), 7.72 (d, J=6.0 Hz, 1H), 7.64-7.58 (m, 1H), 7.55 (dd, J=6.0, 1.5 Hz, 1H), 7.49 (d, J=7.9 Hz, 2H), 7.41 (t, J=7.5 Hz, 2H), 7.36-7.32 (m, 1H), 6.19 (t, J=23.5 Hz, 1H), 5.42 (s, 2H), 4.24-4.18 (m, 8H), 1.27-1.21 (m, 12H). $^{31}P$ NMR (203 MHz, $CD_3OD$) δ 17.17 (s). $^{13}C$ NMR (126 MHz, $CD_3OD$) δ 169.5, 167.5, 159.4, 157.4 (t, J=3.9 Hz), 139.7, 137.6, 133.6, 132.2, 131.8, 130.1, 129.9, 129.7, 129.3, 129.3, 125.3, 119.8, 117.1, 67.9, 65.2-65.1 (m), 45.5 (t, J=150.0 Hz), 16.7-16.6 (m). MS [$ESI^-$] m/z: 648.3 [M–H]$^-$.

Step 2: Synthesis of 3-(4-((bis(diethoxyphosphoryl)methyl)amino)thieno[2,3-d]pyrimidin-2-yl)benzoic acid (5b, Scheme 2)

A solution of the above product, benzyl 3-(4-((bis(diethoxyphosphoryl)methyl)amino)thieno[2,3-d]pyrimidin-2-yl)benzoate (271 mg, 0.42 mmol), in neat TFA (4.6 mL) was stirred at 80° C. for 14 h (monitored by TLC). TFA was then removed by evaporation in vacuo and the residue was dissolved in DCM and then evaporated under reduced pressure (done at least twice). Crude product was purified by silica gel column chromatography using a gradient of 50% EtOAc in hexanes to 100% EtOAc and then to 15% MeOH in EtOAc. Product was isolated as a light brown solid (quantitative yield). $^1H$ NMR (400 MHz, $CDCl_3$ with ~0.1% $CD_3OD$) δ 9.20 (s, 1H), 8.70 (d, J=7.9 Hz, 1H), 8.19 (d, J=7.7 Hz, 1H), 7.70 (d, J=6.0 Hz, 1H), 7.59 (t, J=7.8 Hz, 1H), 7.40 (d, J=6.0 Hz, 1H), 6.08 (t, J=22.2 Hz, 1H), 4.29-4.18 (m, 8H), 1.29 (t, J=7.0 Hz, 6H), 1.20 (t, J=7.0 Hz, 6H). $^{31}P$ NMR (203 MHz, $CDCl_3$) δ 17.50 (s). $^{13}C$ NMR (126 MHz, $CDCl_3$ with ~0.1% $CD_3OD$) δ 169.2, 168.3, 158.4, 155.8, 138.4, 132.7, 131.5, 129.8, 128.6, 123.8, 118.8, 115.9, 115.8, 64.2 (br), 44.1 (t, J=147.0 Hz, 1H), 16.2 (br). MS [$ESI^+$] m/z: 558.1 [M+H]$^+$.

Tetraethyl (((2-(3-aminophenyl)thieno[2,3-d]pyrimidin-4-yl)amino)methylene)bis(phosphonate) (5d; Q=CH, q=1; R=H) (Scheme 6)

A pressure vessel was charged with tetraethyl (((2-(3-nitrophenyl)thieno[2,3-d]pyrimidin-4-yl)amino)methylene)bis(phosphonate) (5a, $R^b$=3-$NO_2$, Q=CH, q=1, R=H; 1.0 eq) and EtOH (0.1 M). $SnCl_2 \cdot 2H_2O$ (5.0 eq) was then added and the mixture was stirred at 80° C. for 2-3 h, cooled to rt and the mixture was slowly added to sat. $NaHCO_3$ solution (10.0 mL) and then extracted with EtOAc (thrice). The combined organic phase was washed with brine, dried over $MgSO_4$, filtered, and concentrated in vacuo. Product was isolated as a yellow solid (80% yield) and used in the next step without further purification. $^1H$ NMR (500 MHz, DMSO-$d_6$) δ 8.52 (d, J=9.7 Hz, 1H), 8.06 (d, J=6.0 Hz, 1H), 7.64-7.62 (m, 1H), 7.58 (d, J=6.0 Hz, 1H), 7.53 (d, J=7.7 Hz, 1H), 7.14 (t, J=7.8

Hz, 1H), 6.67 (dd, J=7.9, 1.5 Hz, 1H), 6.01 (td, J=23.5, 9.7 Hz, 1H), 5.22 (s, 2H), 4.15-4.05 (m, 8H), 1.18-1.10 (m, 12H). $^{31}$P NMR (203 MHz, DMSO-d6) δ 17.18 (s). MS [ESI$^+$] m/z: 529.1 [M+H]$^+$.

General procedures for the preparation of the tetraethyl bisphosphonate ester intermediates from the C-4 amine, followed by deprotection of the esters to give the phosphonic acids were carried out as previously reported [as examples refer to (a) Leung, et al. *J. Med. Chem.* 2013, 56, 7939-7950. (b) Leung, et al *Bioorg. Med. Chem.* 2013, 21, 2229-2240.]

Comparative Examples (((2-(furan-2-yl)thieno[2,3-d]pyrimidin-4-yl)amino) methylene)bis(phosphonic acid) (C-1) (Table 1)

Prepared using the method shown in Scheme 1. Isolated as a light brown solid (73% yield). $^1$H NMR (500 MHz, D$_2$O) δ 7.71 (s, 1H), 7.45 (d, J=5.9 Hz, 1H), 7.40 (d, J=5.9 Hz, 1H), 7.35 (d, J=3.2 Hz, 1H), 6.63 (br, 1H), 5.22 (t, J=20.3 Hz, 1H). $^{31}$P NMR (203 MHz, D$_2$O): δ 12.9. $^{13}$C NMR (125 MHz, D$_2$O): δ 163.4, 156.5, 151.4, 150.1, 145.6, 123.5, 118.8, 115.6, 114.0, 112.5, 48.8 (t, J=130.5 Hz). MS (ESI$^+$) m/z: 392.1 [M+H]$^+$.

(((2-(pyridin-4-yl)thieno[2,3-d]pyrimidin-4-yl) amino)methylene)bis(phosphonic acid) (C-2) (Table 1)

Prepared using this method shown in Scheme 1. Isolated as a yellow solid (76% yield). $^1$H NMR (400 MHz, D$_2$O): δ 8.60 (br, 2H), 8.24 (br, 2H), 7.58 (d, J=6.0 Hz, 1H), 7.52 (d, J=5.9 Hz, 1H), 5.26 (t, J=19.4 Hz, 1H). $^{31}$P NMR (162 MHz, D$_2$O): δ 13.7. $^{13}$C NMR (100 MHz, D$_2$O): δ 165.4, 157.4, 156.9, 148.5, 146.5, 124.4, 122.8, 118.8, 116.5, 48.8 (t, J=124.0 Hz). MS (ESI$^+$) m/z: 403.1 [M+H]$^+$.

Representative Compounds of Formula I (((2-([1,1'-biphenyl]-3-yl)thieno[2,3-d]pyrimidin-4-yl)amino)methylene)bis(phosphonic acid) (I-1) (Table 2)

Prepared using the method shown in Scheme 6.

Step 1: Tetraethyl (((2-(3-bromophenyl)thieno[2,3-d]pyrimidin-4-yl)amino)methylene)bis(phosphonate) (5c, R$^b$=Br, R=H; 1 eq), [1,1'-biphenyl]-3-ylboronic acid (1.3 eq), Pd(PPh$_3$)$_4$ (10 mol %), and KF (2.5 eq) were placed in a microwave reactor vial and the mixture was purged with Argon (Ar). The mixture was added with MeOH (2.5 mL per 0.10 mmol of 5c) and purged again with Ar. The reaction mixture was heated via a microwave (120° C.) for 20 min. The reaction mixture was cooled down, filtered through celite, and concentrated to dryness under vacuum. Crude product was purified by silica gel column chromatography using a solvent gradient of 5% to 100% EtOAc in hexanes and then from 0% to 20% MeOH in EtOAc. Tetraethyl (((2-([1,1'-biphenyl]-3-yl)thieno[2,3-d]pyrimidin-4-yl) amino)methylene)bis(phosphonate) (R$^2$=[1,1'-biphenyl]-3-yl; R=H) was isolated as a light yellow solid (82% yield). $^1$H NMR (500 MHz, CDCl$_3$) δ 8.74 (s, 1H), 8.45 (d, J=7.8 Hz, 1H), 7.73-7.69 (m, 3H), 7.57 (t, J=7.7 Hz, 1H), 7.48 (t, J=7.6 Hz, 2H), 7.40-7.36 (m, 3H), 6.02-5.91 (m, 2H; —NH and α-CH to the bisphosphonate), 4.30-4.13 (m, 8H), 1.29-1.22 (m, 12H). $^{31}$P NMR (203 MHz, CDCl$_3$) δ 16.76.

Step 2: Deprotection of tetraethyl bisphosphonate ester. Final product (I-1) was afforded as a light brown solid (75% yield). $^1$H NMR (500 MHz, D$_2$O) δ 8.52 (s, 1H), 8.31 (d, J=7.7 Hz, 1H), 7.88-7.76 (m, 3H), 7.66 (t, J=7.8 Hz, 1H), 7.60 (d, J=5.9 Hz, 1H), 7.55 (t, J=7.7 Hz, 2H), 7.48 (d, J=6.0 Hz, 1H), 7.44 (d, J=7.4 Hz, 1H), 5.19 (t, J=17.7 Hz, 1H). $^{31}$P NMR (203 MHz, D$_2$O): δ 13.9. $^{13}$C NMR (125 MHz, D$_2$O): δ 165.7 160.4, 157.0, 141.0, 140.3, 138.3, 129.4, 129.1, 129.0, 127.8, 127.5, 127.1, 126.4, 123.2, 118.8, 115.7. Cα observed by HSQC. HSQC ($^1$H-$^{13}$C): $^1$H δ 5.19 correlates with $^{13}$C δ 49.0. MS (ESI$^+$) m/z: 478.2 [M+H]$^+$.

(((2-(3-(phenylsulfonamido)phenyl)thieno[2,3-d] pyrimidin-4-yl)amino)methylene)bis(phosphonic acid) (I-2) (Table 2)

Prepared using the method shown in Scheme 6.

Step 1: To the solution of tetraethyl (((2-(3-aminophenyl) thieno[2,3-d]pyrimidin-4-yl)amino)methylene)bis(phosphonate) (5d, Q=CH, q=1, 3-amino; R=H; 1.0 eq) in dry DCM (1.3 mL per 0.1 mmol 5d) at 0° C. was added pyridine (7.5 eq). Benzenesulfonyl chloride (1.2 eq) was then added and the reaction was allowed to warm to rt (reaction progress was monitored by TLC). Once complete (typically, after ~1-2 h), the reaction was poured into sat. NaHCO$_3$ solution, extracted with EtOAc (thrice), washed with 1M HCl, and the combined organic phase was dried over MgSO$_4$, and then concentrated in vacuo. Crude product was purified by silica gel column chromatography (product eluted at 5% MeOH in EtOAc). Tetraethyl (((2-(3-(phenylsulfonamido)phenyl) thieno[2,3-d]pyrimidin-4-yl)amino)methylene)bis(phosphonate) was isolated as a cream-color solid (73%). $^1$H NMR (500 MHz, DMSO-d$_6$) δ 10.61 (s, —NH), 8.58 (d, J=9.7 Hz, —NH), 8.22 (d, J=8.8 Hz, 2H), 8.05 (d, J=6.0 Hz, 1H), 7.84-7.82 (m, 2H), 7.63-7.55 (m, 4H), 7.24 (d, J=8.8 Hz, 2H), 5.94 (td, J=23.3, 9.4 Hz, 1H), 4.13-4.04 (m, 8H), 1.16-1.08 (m, 12H). $^{31}$P NMR (203 MHz, DMSO-d$_6$) δ 17.12 (s).

Step 2: Deprotection of tetraethyl bisphosphonate ester. Final product (I-2) was afforded as a cream solid (88% yield). $^1$H NMR (500 MHz, D$_2$O) δ 8.20 (d, J=8.3 Hz, 2H), 7.87 (d, J=7.6 Hz, 2H), 7.68-7.63 (m, 1H), 7.59-7.56 (m, 3H), 7.45 (d, J=5.8 Hz, 1H), 7.22 (d, J=8.4 Hz, 2H), 5.15 (t, J=17.0 Hz, 1H). $^{31}$P NMR (203 MHz, D$_2$O) δ 13.87 (s). $^{13}$C NMR (101 MHz, D$_2$O) δ 165.7, 159.7, 156.9, 140.4, 138.2, 133.4 (two carbons), 129.4 (two carbons), 129.3, 129.2, 126.8, 122.8, 121.3, 118.8, 115.5. C-α to the bisphosphonate was observed by HSQC. HSQC ($^1$H-$^{13}$C): $^1$H at δ 5.15 correlates to $^{13}$C-α at δ 47.0. HRMS [ESI$^+$] calculated for C$_{19}$H$_{16}$N$_4$Na$_3$O$_8$P$_2$S$_2$ m/z, 622.95724; found 622.95769 [M+3 Na]$^+$.

(((2-(3-(thiophene-2-carboxamido)phenyl)thieno[2, 3-d]pyrimidin-4-yl)amino)methylene)bis(phosphonic acid) (I-3) (Table 2)

Prepared using the method shown in Scheme 6.

Step 1: To the mixture of tetraethyl (((2-(3-aminophenyl) thieno[2,3-d]pyrimidin-4-yl)amino)methylene)bis(phosphonate) (5d, Z=CH, n=1, 3-amino; RH; 1.0 eq) and 2-thiophenecarboxylic acid (1.1 eq) in dry DMF (2.0 mL per 0.1 mmol 6) was added DIPEA (2.0 eq) followed by HBTU (1.1 eq) under an Ar balloon. The solution was stirred at rt for 4 h (monitored by TLC and LC-MS). The reaction was then added with brine (10 mL) and was extracted with EtOAc (20.0 mL; twice). The combined organic phases were washed with sat. NH$_4$Cl solution (10 mL), brine, dried over Na$_2$SO$_4$ and concentrated in vacuo. Crude product was purified by silica-gel column chromatography with a gradient from 25% EtOAc in hexanes to 100% EtOAc and then to 20% MeOH in EtOAc (product eluted at 10% MeOH in EtOAc). Tetraethyl (((2-(3-(thiophene-2-carboxamido)phenyl)thieno[2,3-d]pyrimidin-4-yl)amino)methylene)bis(phosphonate) was isolated as a yellow solid (77%). $^1$H NMR (500 MHz, DMSO-$d_6$) δ 10.41 (s, —NH), 8.80 (t, J=1.8 Hz, 1H), 8.66 (d, J=9.7 Hz, —NH), 8.12 (d, J=7.9 Hz, 1H), 8.10-8.09 (m, 2H), 7.89-7.87 (m, 2H), 7.64 (d, J=6.0 Hz, 1H), 7.51 (t, J=7.9 Hz, 1H), 7.25 (dd, J=4.9, 3.8 Hz, 1H), 6.06 (td, J=23.4, 9.7 Hz, 1H), 4.18-4.06 (m, 8H), 1.20-1.10 (m, 12H). $^{31}$P NMR (203 MHz, DMSO-$d_6$) δ 16.97 (s). MS [ESI$^+$] m/z: 639.1 [M+H$^+$]$^+$.

Step 2: Deprotection of tetraethyl bisphosphonate ester. Final product (I-3) was afforded as yellow solid (71% yield). $^1$H NMR (400 MHz, D$_2$O) δ 8.35 (s, 1H), 8.17 (d, J=7.9 Hz, 1H), 7.94 (dd, J=3.7, 0.8 Hz, 1H), 7.86 (dd, J=8.0, 1.2 Hz, 1H), 7.80 (dd, J=5.0, 0.9 Hz, 1H), 7.64-7.60 (m, 2H), 7.49 (d, J=6.0 Hz, 1H), 7.27 (dd, J=4.9, 3.9 Hz, 1H), 5.14 (t, J=18.8 Hz, 1H). $^{31}$P NMR (203 MHz, D$_2$O) δ 13.81 (s). $^{13}$C NMR (101 MHz, D$_2$O) δ 165.5, 163.3, 159.8, 156.7, 138.7, 137.6, 137.2, 132.2, 130.4, 129.5, 128.4, 125.2, 124.3, 123.0, 121.9, 119.0, 115.9. C-α to the bisphosphonate was observed by HSQC. HSQC ($^1$H-$^{13}$C): $^1$H at δ 5.14 correlates to $^{13}$C-α at δ 49.5. HRMS [ESI$^+$] calculated for $C_{18}H_{14}N_4Na_3O_7P_2S_2$ m/z, 592.94667; found 592.94813 [M+3Na]$^+$.

(((2-(3-(cyclohexanecarboxamido)phenyl)thieno[2,3-d]pyrimidin-4-yl)amino)methylene)bis(phosphonic acid) (I-4) (Table 2)

Prepared following the protocol described for I-3. Step 1: The intermediate, tetraethyl (((2-(3-(cyclohexanecarboxamido)phenyl)thieno[2,3-d]pyrimidin-4-yl)amino)methylene)bis(phosphonate) ($R^c$=3-(cyclohexanecarboxamido) phenyl; R=H) was isolated as a yellow solid (68% yield). $^1$H NMR (500 MHz, DMSO-d6) δ 9.97 (s, —NH), 8.68 (t, J=1.8 Hz, 1H), 8.62 (d, J=9.7 Hz, —NH), 8.09 (d, J=6.0 Hz, 1H), 8.03 (d, J=7.9 Hz, 1H), 7.71 (ddd, J=8.1, 2.0, 0.9 Hz, 1H), 7.62 (d, J=6.0 Hz, 1H), 7.42 (t, J=7.9 Hz, 1H), 6.04 (td, J=23.4, 9.7 Hz, 1H), 4.18-4.06 (m, 8H), 2.37 (tt, J=11.6, 3.4 Hz, 1H), 1.78-1.65 (m, 5H), 1.48-1.20 (m, 5H), 1.19-1.09 (m, 12H). $^{31}$P NMR (203 MHz, DMSO-d6) δ 16.98 (s). MS [ESI$^+$] m/z: 639.2 [M+H]$^+$.

Step 2: Final product (I-4) was afforded as a yellow solid (81% yield). $^1$H NMR (500 MHz, D$_2$O) δ 8.25 (s, 1H), 8.14 (d, J=7.9 Hz, 1H), 7.82 (d, J=8.1 Hz, 1H), 7.64-7.59 (m, 2H), 7.50 (d, J=5.9 Hz, 1H), 5.11 (t, J=19.1 Hz, 1H), 2.49 (tt, J=11.8, 3.3 Hz, 1H), 1.99-1.73 (m, 5H), 1.56-1.27 (m, 5H). $^{31}$P NMR (203 MHz, D$_2$O) δ 13.77 (s). $^{13}$C NMR (101 MHz, D$_2$O) δ 179.1, 165.6, 159.9, 157.0, 138.6, 137.5, 129.5, 124.9, 123.8, 123.1, 121.4, 118.9, 115.8, 45.8, 29.1, 25.3, 25.2. C-α to the bisphosphonate was observed by HSQC. HSQC ($^1$H-$^{13}$C): $^1$H at δ 5.11 correlates to $^{13}$C-α at δ 49.0. HRMS [ESI$^+$] calculated for $C_{20}H_{22}N_4Na_3O_7P_2S$ m/z, 593.03720; found 593.03804 [M+3 Na]$^+$.

(((2-(3-(4-methoxybenzamido)phenyl)thieno[2,3-d]pyrimidin-4-yl)amino)methylene)bis(phosphonic acid) (I-5) (Table 2)

Prepared using the method shown in Scheme 6.

Step 1: To a stirring solution of tetraethyl (((2-(3-aminophenyl)thieno[2,3-d]pyrimidin-4-yl)amino)methylene)bis(phosphonate) (5d, Q=CH, q=1, 3-amino; R H; 1.0 eq) in dry DCM (6.5 mL per 1 mmol of 5d) at 0° C. was added dry Et$_3$N (3.0 eq). Para-methoxybenzoyl chloride (1.2 eq) was then added dropwise under Ar balloon. The solution was stirred and allowed to warm to RT (reaction progress was monitored by TLC or LC-MS). Once complete (typically, after ~1 h), the reaction mixture was poured into sat. NaHCO$_3$ solution and extracted with EtOAc (twice), washed with brine, dried over Na$_2$SO$_4$ and concentrated under vacuum. Crude product was purified by silica gel column chromatography with a gradient from 25% EtOAc in hexanes to 100% EtOAc and then to 20% MeOH in EtOAc (product eluted at 15% MeOH in EtOAc).

Tetraethyl (((2-(3-(4-methoxybenzamido)phenyl)thieno[2,3-d]pyrimidin-4-yl)amino)methylene)bis(phosphonate) was isolated as a yellow solid (quantitative yield). $^1$H NMR (500 MHz, DMSO-$d_6$) δ 10.27 (s, —NH), 8.84 (t, J=1.7 Hz, 1H), 8.65 (d, J=9.7 Hz, —NH), 8.11-8.09 (m, 2H), 8.02 (d, J=8.8 Hz, 2H), 7.90 (dd, J=6.9, 1.2 Hz, 1H), 7.64 (d, J=6.0 Hz, 1H), 7.49 (t, J=7.9 Hz, 1H), 7.08 (d, J=8.9 Hz, 2H), 6.06 (td, J=23.4, 9.7 Hz, 1H), 4.18-4.07 (m, 8H), 3.85 (s, 3H), 1.19-1.10 (m, 12H). $^{31}$P NMR (203 MHz, DMSO-d6) δ 17.01 (s). MS [ESI$^+$] m/z: 663.2 [M+H]$^+$.

Step 2: Deprotection of tetraethyl bisphosphonate ester. Final product (I-5) was afforded as a beige solid (81%). $^1$H NMR (400 MHz, D$_2$O) δ 8.36 (s, 1H), 8.19 (d, J=7.8 Hz, 1H), 7.98 (d, J=8.8 Hz, 2H), 7.91 (d, J=8.1 Hz, 1H), 7.68-7.60 (m, 2H), 7.50 (d, J=6.0 Hz, 1H), 7.17 (d, J=8.9 Hz, 2H), 5.11 (t, J=19.0 Hz, 1H), 3.94 (s, 3H). $^{31}$P NMR (162 MHz, D$_2$O) δ 13.78 (s). $^{13}$C NMR (126 MHz, D$_2$O) δ 169.1, 165.0, 162.2, 160.0, 156.8, 138.7, 137.6, 129.6, 129.5, 126.3, 125.1, 124.4, 122.6, 122.0, 119.2, 116.0, 114.1, 55.5. C-α to the bisphosphonate was observed by HSQC. HSQC ($^1$H-$^{13}$C): $^1$H at δ 5.11 correlates to $^{13}$C-α at δ 50.0. HRMS [ESI$^+$] calculated for $C_{21}H_{18}N_4Na_3O_8P_2S$ m/z, 617.00082; found 617.00181 [M+3 Na]$^+$.

(((2-(3-(phenylcarbamoyl)phenyl)thieno[2,3-d]pyrimidin-4-yl)amino)methylene)bis(phosphonic acid) (I-34) (Table 2)

Prepared using the method shown in Scheme 2.

Step 1: A solution of 5d [tetraethyl (((2-(3-aminophenyl)thieno[2,3-d]pyrimidin-4-yl)amino)methylene)bis(phosphonate)] was reacted with the 4-fluorobenzoic acid in dry DMF in the presence of DIPEA (2 eq) and HBTU (1.1 eq) under argon balloon at RT. The reaction was followed by TLC, upon completion of the reaction, brine (10 ml) was added and the mixture is extracted with ethyl acetate. The organic phase was washed with saturated ammonium chloride (10 ml), brine, dried over sodium sulfate and concentrated in vacuo. Crude product was purified by silica-gel column chromatography using a Combiflash instrument. Product eluted at 15% methanol in ethyl acetate and was obtained as a yellow solid (48 mg, 65%). $^1$H NMR (500 MHz, CDCl$_3$) δ 8.39 (s, 1H), 8.28 (d, J=7.9 Hz, 1H), 8.14 (d, J=7.6 Hz, 1H), 8.03-7.90 (m, 3H), 7.52 (t, J=8.0 Hz, 1H), 7.37 (d, J=6.0 Hz, 1H), 7.21 (t, J=8.5 Hz, 2H), 5.97 (d, J=9.9 Hz, 1H), 5.78 (s, 1H), 4.35-4.08 (m, 8H), 1.29-1.19 (m, 12H). $^{31}$P NMR (203 MHz, CDCl$_3$) δ 16.84.

After deprotection of the tetraethyl esters, the final compound I-34 was isolated as a beige powder (26.1 mg, 63%). $^1$H NMR (400 MHz, D$_2$O) δ 8.37 (s, 1H), 8.20 (d, J=7.9 Hz, 1H), 8.05-7.98 (m, 2H), 7.93 (d, J=8.1 Hz, 1H), 7.70-7.60 (m, 2H), 7.51 (d, J=6.0 Hz, 1H), 7.39-7.29 (m, 2H), 5.17 (t, J=19.0 Hz, 1H). $^{31}$P NMR (162 MHz, D$_2$O) δ 13.93 (s). $^{13}$C NMR (126 MHz, D$_2$O) δ 168.5, 165.8, 165.4, 163.8, 159.7, 156.9, 138.5, 137.4, 130.1, 130.0, 129.4, 125.1, 124.1, 122.9, 121.7, 118.9, 115.8, 115.7, 115.5, 49.5 (t, J=122.7

Hz). HRMS [ESI⁻] calculated for $C_{20}H_{15}FN_4NaO_7P_2S$ m/z [M-2H+Na]⁻ 559.0024; found 559.0010 [M-2H+Na]⁻.

(((2-(3-(phenylcarbamoyl)phenyl)thieno[2,3-d]pyrimidin-4-yl)amino)methylene)bis(phosphonic acid) (I-6) (Table 2)

Tetraethyl (((2-(3-(phenylcarbamoyl)phenyl)thieno[2,3-d]pyrimidin-4-yl)amino)methylene)bis(phosphonate) was isolated as light yellow solid (84% yield). ¹H NMR (400 MHz, DMSO-d₆) δ 10.47 (s, —NH), 8.95 (s, 1H), 8.75 (d, J=9.6 Hz, —NH), 8.57 (d, J=7.9 Hz, 1H), 8.10 (d, J=5.7 Hz, 1H), 8.07 (d, J=7.9 Hz, 1H), 7.82 (d, J=7.7 Hz, 2H), 7.71-7.66 (m, 2H), 7.39-7.35 (m, 2H), 7.12 (t, J=7.4 Hz, 1H), 6.03 (br, 1H), 4.18-4.00 (m, 8H), 1.19-1.08 (m, 12H). ³¹P NMR (162 MHz, DMSO-d₆) δ 17.05 (s). ¹³C NMR (126 MHz, DMSO-d₆) δ 167.6, 165.5, 157.5, 156.0 (t, J=3.7 Hz), 139.2, 137.7, 135.5, 130.4, 129.4, 128.7, 128.6, 127.1, 123.8, 123.7, 120.3, 120.2, 115.5, 62.9-62.7 (m), 16.2-16.1 (m). C-α to the bisphosphonate was observed by HSQC. HSQC (¹H-¹³C): ¹H at δ 6.03 correlates to ¹³C-α at δ 45.1. MS [ESI⁺] m/z: 633.2 [M+H]⁺.

Step 2: Deprotection of tetraethyl bisphosphonate ester. Final product (I-6) was isolated as off-white solid (67%). ¹H NMR (400 MHz, D₂O) δ 8.81 (s, 1H), 8.58 (d, J=7.9 Hz, 1H), 8.06 (d, J=7.8 Hz, 1H), 7.76 (t, J=7.8 Hz, 1H), 7.66-7.63 (m, 3H), 7.56-7.52 (m, 3H), 7.36 (t, J=7.4 Hz, 1H), 5.20 (t, J=19.0 Hz, 1H). ³¹P NMR (203 MHz, D₂O) δ 13.91 (s). ¹³C NMR (126 MHz, D₂O) δ 169.4, 165.5, 159.7, 157.0, 138.3, 136.9, 134.4, 132.0, 129.4, 129.3, 129.2, 126.9, 126.0, 123.2, 123.0, 119.0, 115.9, 49.3. HRMS [ESI⁺] calculated for $C_{20}H_{16}N_4Na_3O_7P_2S$ m/z, 586.9903; found 586.9903 [M+3 Na]⁺.

(((2-(3-(3-(4-fluorophenyl)ureido)phenyl)thieno[2,3-d]pyrimidin-4-yl)amino)methylene)bis(phosphonic acid) (I-7) (Table 2)

Prepared using the method shown in Scheme 6.

Step 1: To the mixture of triphosgene (1.0 eq) in dry toluene (0.05 M) was added 4-fluoroaniline (1.5 eq) at RT under Ar. Et₃N (1.1 eq) was then added dropwise and the reaction mixture was refluxed for 4 h. The solvent was removed in vacua and the residue was re-dissolved in dry DCM (1.0-2.0 mL). This was then added to the solution of tetraethyl (((2-(3-aminophenyl)thieno[2,3-d]pyrimidin-4-yl)amino)methylene)bis(phosphonate) (5d, Q=CH, q=1, 3-amino; R=H; 0.80 eq) and Et₃N (1.2 eq) in dry DCM (1.0 mL per 0.1 mmol 5d) in an ice-bath. The resulting mixture was stirred at rt until completion (typically, after 12 h). The solvent was then removed in vacuo and the residue was dissolved in EtOAc, washed with saturated NH₄Cl, brine, dried over Na₂SO₄, and the organic extract was collected and concentrated in vacuo. Crude product was purified by silica-gel chromatography using a Combiflash instrument (product eluted at ~10% MeOH in EtOAc). Tetraethyl (((2-(3-(3-(4-fluorophenyl)ureido)phenyl)thieno[2,3-d]pyrimidin-4-yl)amino)methylene)bis(phosphonate)) was isolated as a yellow solid (71% yield). ¹H NMR (500 MHz, CDCl₃) δ 8.12-8.01 (m, 4H), 8.08 (s, 1H), 7.79 (s, 1H), 7.42-7.37 (m, 3H), 7.28 (d, J=7.8 Hz, 1H), 7.21 (d, J=5.6 Hz, 1H), 6.91 (t, J=8.7 Hz, 2H), 6.74 (br_s, 1H), 6.20 (t, J=25.8 Hz, 1H), 4.32-4.20 (m, 8H), 1.29-1.24 (m, 12H). ³¹P NMR (203 MHz, CDCl₃) δ 17.14 (s). MS [ESI⁺] m/z: 666.2 [M+H]⁺.

Step 2: Deprotection of tetraethyl bisphosphonate ester. Final product (I-7) was afforded as a yellow solid (74% yield). ¹H NMR (400 MHz, DMSO-d₆) δ 8.90 (br_s, 1H), 8.73 (br_s, 1H), 8.34 (s, 1H), 8.05 (d, J=7.8 Hz, 1H), 7.89 (br, 1H), 7.73 (d, J=7.5 Hz, 2H), 7.57 (d, J=5.6 Hz, 1H), 7.50-7.47 (m, 2H), 7.41 (t, J=7.9 Hz, 1H), 7.12 (t, J=8.7 Hz, 2H), 5.62 (br_, 1H). ³¹P NMR (162 MHz, DMSO-d₆) δ 13.98 (s). MS [ESI⁺] m/z: 554.0 [M+H]⁺.

(((2-(3-(4-methylbenzamido)phenyl)thieno[2,3-d]pyrimidin-4-yl)amino)methylene)bis(phosphonic acid) (I-18) (Table 2)

Step 1: Tetraethyl (((2-(3-(4-methylbenzamido)phenyl)thieno[2,3-d]pyrimidin-4-yl)amino)methylene)bis(phosphonate) was isolated as a yellow solid. ¹H NMR (500 MHz, DMSO-d₆) δ 10.34 (s, —NH), 8.85 (t, J=1.8 Hz, 1H), 8.65 (d, J=9.7 Hz, —NH), 8.12-8.09 (m, 2H), 7.93 (d, J=8.2 Hz, 2H), 7.91 (ddd, J=8.1, 2.1, 1.0 Hz, 1H), 7.64 (d, J=6.0 Hz, 1H), 7.50 (t, J=7.9 Hz, 1H), 7.35 (d, J=7.9 Hz, 2H), 6.06 (td, J=23.4, 9.7 Hz, 1H), 4.18-4.05 (m, 8H), 2.40 (s, 3H), 1.19-1.10 (m, 12H). ³¹P NMR (203 MHz, DMSO-d₆) δ 17.00 (s). MS [ESI⁺] m/z: 647.2 [M+H]⁺.

Step 2: Compound I-18 was isolated as a light yellow solid. ¹H NMR (500 MHz, D₂O) δ 8.38 (s, 1H), 8.20 (d, J=7.6 Hz, 1H), 7.93 (d, J=7.1 Hz, 1H), 7.89 (d, J=7.9 Hz, 2H), 7.68-7.63 (m, 2H), 7.51 (d, J=5.9 Hz, 1H), 7.46 (d, J=7.9 Hz, 2H), 5.15 (t, J=18.9 Hz, 1H), 2.47 (s, 3H). ³¹P NMR (203 MHz, D₂O) δ 13.82 (s). ¹³C NMR (101 MHz, D₂O) δ 169.3, 165.6, 159.5, 156.8, 143.5, 138.3, 137.5, 130.7, 129.4, 129.3, 127.5, 125.0, 124.1, 123.3, 121.6, 118.8, 115.8, 48.9 (t, J=124.8 Hz), 20.6. HRMS [ESI⁺] calculated for $C_{21}H_{18}N_4Na_3O_7P_2S$ m/z 601.00590; found 601.00773 [M+3 Na]⁺.

(((2-(3-((4-methoxyphenyl)carbamoyl)phenyl)thieno[2,3-d]pyrimidin-4-yl)amino)methylene)bis(phosphonic acid) (I-36) (Table 2)

Step 1: Tetraethyl (((2-(3-((4-methoxyphenyl)carbamoyl)phenyl)thieno[2,3-d]pyrimidin-4-yl)amino)methylene)bis(phosphonate) was isolated as a light brown solid. ¹H NMR (500 MHz, CDCl₃ with ~0.1% CD₃OD) δ 9.01 (s, 1H), 8.67 (br_s, 1H), 8.59 (d, J=7.8 Hz, 1H), 8.11 (d, J=7.6 Hz, 1H), 7.68 (d, J=8.8 Hz, 2H), 7.61 (t, J=7.7 Hz, 1H), 7.45 (d, J=5.3 Hz, 1H), 7.37 (d, J=6.0 Hz, 1H), 6.92 (d, J=9.0 Hz, 2H), 5.86 (t, J=22.3 Hz, 1H), 4.27-4.10 (m, 8H), 3.82 (s, 3H), 1.26 (t, J=7.1 Hz, 6H), 1.21 (t, J=7.1 Hz, 6H). ³¹P NMR (203 MHz, CDCl₃) δ 17.10 (s). MS [ESI⁺] m/z: 663.4 [M+H]⁺.

Step 2: Compound I-36 was isolated as off-white solid. ¹H NMR (500 MHz, D₂O) δ 8.74 (s, 1H), 8.54 (d, J=7.8 Hz, 1H), 8.00 (d, J=7.7 Hz, 1H), 7.72 (t, J=7.8 Hz, 1H), 7.62 (d, J=5.9 Hz, 1H), 7.51-7.49 (m, 3H), 7.06 (d, J=8.9 Hz, 2H), 5.18 (t, J=18.9 Hz, 1H), 3.86 (s, 3H). ¹³C NMR (126 MHz, D₂O) δ 169.3, 165.5, 159.7, 157.0, 156.7, 138.3, 134.3, 132.0, 130.1, 129.3, 129.3, 126.8, 124.8, 123.2, 118.9, 115.9, 114.4, 55.5. HSQC (¹H-¹³C): ¹H at δ 5.18 correlates to ¹³C-α at δ 49.3. ³¹P NMR (203 MHz, D₂O) δ 13.91 (s). HRMS [ESI⁺] calculated for $C_{21}H_{18}N_4Na_3O_8P_2S$ m/z, 617.00082; found 617.00090 [M+3Na]⁺.

(((2-(3-((3-fluoro-4-methoxyphenyl)carbamoyl)phenyl)thieno[2,3-d]pyrimidin-4-yl)amino)methylene)bis(phosphonic acid) (I-37) (Table 2)

Step 1: Tetraethyl (((2-(3-((3-fluoro-4-methoxyphenyl)carbamoyl)phenyl)thieno[2,3-d]pyrimidin-4-yl)amino)methylene)bis(phosphonate) was isolated as a yellow solid. ¹H NMR (500 MHz, CDCl₃) δ 9.28 (s, 1H), 9.10 (br_s, 1H), 8.62 (d, J=7.8 Hz, 1H), 8.14 (d, J=7.7 Hz, 1H), 7.70 (dd, J=13.1, 2.3 Hz, 1H), 7.66 (d, J=8.7 Hz, 1H), 7.59 (t, J=7.7 Hz, 1H), 7.42 (d, J=5.8 Hz, 1H), 7.27 (d, J=6.0 Hz, 1H), 6.94 (t, J=9.1 Hz, 1H), 6.77 (br_s, 1H), 5.63 (td, J=22.9, 7.7 Hz, 1H), 4.24-4.11 (m, 8H), 1.24-1.20 (m, 12H). $^{31}$P NMR (203 MHz, CDCl$_3$) δ 17.27 (s). $^{13}$C NMR (126 MHz, CDCl$_3$) δ 168.4, 165.3, 158.5, 155.8 (t, J=3.3 Hz), 152.2 (d, J=244.1 Hz), 144.3 (d, J=10.9 Hz), 138.0, 134.7, 132.6 (d, J=9.4 Hz), 131.1, 130.2, 129.1, 126.8, 123.9, 117.9, 116.3 (d, J=3.4 Hz), 115.5, 113.7 (d, J=2.5 Hz), 109.7 (d, J=22.6 Hz), 63.9-63.7 (m), 56.7, 46.9 (t, J=147.9 Hz), 16.5-16.4 (m). MS [ESI$^+$] m/z: 681.3 [M+H]$^+$.

Step 2: Compound I-37 was isolated as a light yellow solid. $^1$H NMR (500 MHz, D$_2$O) δ 8.77 (s, 1H), 8.55 (d, J=7.8 Hz, 1H), 8.03 (d, J=7.8 Hz, 1H), 7.74 (t, J=7.8 Hz, 1H), 7.64 (d, J=5.9 Hz, 1H), 7.53-7.51 (m, 2H), 7.34 (d, J=8.5 Hz, 1H), 7.23 (t, J=9.1 Hz, 1H), 5.21 (t, J=18.5 Hz, 1H), 3.95 (s, 3H). $^{31}$P NMR (203 MHz, D$_2$O) δ 13.90 (s). $^{13}$C NMR (126 MHz, D$_2$O) δ 168.8, 165.5, 159.5, 157.0, 151.3 (d, J=242.1 Hz), 144.3 (d, J=10.9 Hz), 138.1, 133.9, 132.0, 130.5 (d, J=9.4 Hz), 129.3, 129.2, 126.8, 123.2, 118.7, 118.7 (d, J=3.1 Hz). 115.8, 113.9 (d, J=1.9 Hz), 111.0 (d, J=21.8 Hz), 56.3. HSQC ($^1$H-$^{13}$C): $^1$H at δ 5.19 correlates to $^{13}$C-α at δ 49.0. HRMS [ESI$^+$] calculated for C$_{21}$H$_{17}$O$_8$N$_4$FNa$_3$P$_2$S m/z, 634.99140; found 634.99164 [M+3 Na]$^+$.

Synthesis of 2-(methylthio)thieno[3,2-d]pyrimidin-4 (3H)-one (intermediate 10 in Scheme 2)

Methyl-3-amino-2-thiophenecarboxylate (1.00 g, 6.36 mmol) was added to 4M hydrochloric acid in dioxane (9.5 ml), followed by methyl thiocyanate (465 mg, 6.36 mmol). The resulting suspension was heated to 90° C. in a sealed pressure tube for 24 h. The reaction was followed by TLC, upon completion the mixture was allowed to cool to RT and the resulting white precipitate was collected by vacuum filtration. The solid was washed with ethanol followed by hexane. The resulting white solid (1.19 g, 94%) was used in the next step without any further purification.

$^1$H NMR (500 MHz, DMSO-d$_6$) δ 8.14 (d, J=5.2 Hz, 1H), 7.31 (d, J=5.2 Hz, 1H), 2.54 (s, 3H). $^{13}$C NMR (126 MHz, DMSO) δ 158.2, 157.7, 157.3, 135.1, 124.5, 119.1, 12.9.

4-chloro-2-(methylthio)thieno[3,2-d]pyrimidine (intermediate 11 in Scheme 2)

Phosphorus oxychloride (17.9 ml, 192 mmol) was added to compound 10 (3.80 g, 19.2 mmol) in a reaction flask and heated at 106° C. (reflux) for 12 h. The reaction was followed by TLC. When reaction was completed, the phosphorus oxychloride was removed by distillation and the remaining reaction mixture was cooled down to 0° C., then it was quenched by dropwise addition of saturated aqueous sodium bicarbonate until pH 7 was obtained. The aqueous layer was extracted with DCM (thrice) and the combined organic layers were washed with brine and then concentrated under reduced pressure. The product was obtained as a white powder (3.04 g, 73%). $^1$H NMR (500 MHz, CDCl$_3$) δ 7.98 (d, J=5.5 Hz, 1H), 7.45 (d, J=5.5 Hz, 1H), 2.65 (s, 3H). $^{13}$C NMR (126 MHz, CDCl$_3$) δ 168.9, 162.5, 154.6, 137.5, 126.1, 124.2, 14.7. MS [ESI$^+$] m/z: 217.03 and 219.03 [M+H]$^+$.

2-(methylthio)thieno[3,2-d]pyrimidin-4-amine (intermediate 12 in Scheme 2)

Ammonium hydroxide 28% (18.7 ml, 592 mmol) was added to intermediate 11 (1.28 g, 5.93 mmol). The reaction was heated to 90° C. for 12 h (overnight). The reaction was followed by TLC. The mixture was then allowed to cool to RT, filtered, washed with water and air dried. The product was obtained as a light green powder (1.06 g, 91%). $^1$H NMR (500 MHz, DMSO) δ 8.06 (d, J=5.4 Hz, 1H), 7.48 (s, 2H), 7.26 (d, J=5.3 Hz, 1H), 2.46 (s, 3H). $^{13}$C NMR (126 MHz, DMSO) δ 166.7, 160.5, 157.7, 133.7, 123.6, 110.8, 13.3. MS [ESI$^+$] m/z: 198.05 [M+H]$^+$.

Tetraethyl (((2-(methylthio)thieno[3,2-d]pyrimidin-4-yl)amino)methylene) bis(phosphonate) (intermediate 13 in Scheme 2)

A pressure vessel charged with compound 12 (750 mg, 3.79 mmol) in toluene (2.2 ml) was added to diethyl phosphite (3.4 ml, 26.5 mmol) and triethyl orthoformate (1.1 ml, 6.45 mmol). The mixture was heated at 130° C. for 48 h and monitored by TLC and LC-MS. Cooled down and concentrated in vacuo. Crude product was purified by silica gel column chromatography. The product elutes at 20% methanol in ethyl acetate. Product was obtained as yellow solid (1.00 g, 55%). $^1$H NMR (500 MHz, CDCl$_3$) δ 7.73 (d, J=5.3 Hz, 1H), 7.33 (d, J=5.3 Hz, 1H), 5.70 (td, J=21.9, 9.8 Hz, 1H), 5.49 (d, J=9.2 Hz, 1H), 4.29-4.12 (m, 8H), 2.58 (s, 3H), 1.33-1.22 (m, 12H). $^{31}$P NMR (203 MHz, CDCl$_3$) δ 16.37. $^{13}$C NMR (126 MHz, CDCl$_3$) δ 167.9, 161.4, 155.1, 132.4, 124.6, 112.1, 63.9 (m), 44.7 (t, J=146.8 Hz), 16.5 (m), 14.4. MS [EST$^+$] m/z: 484.19 [M+H]$^+$.

(((2-(3-((3-fluoro-4-methoxyphenyl)carbamoyl)phenyl)thieno[3,2-d]pyrimidin-4-yl)amino)methylene) bis(phosphonic acid) (I42) (Table 2)

Tetraethyl (((2-(3-((3-fluoro-4-methoxyphenyl)carbamoyl)phenyl)thieno[3,2-d]pyrimidin-4-yl)amino)methylene) bis(phosphonate) was isolated as a light yellow solid (39.3 mg, 56%). $^1$H NMR (500 MHz, CDCl$_3$) δ 9.37 (s, 1H), 9.26 (s, 1H), 8.56 (d, J=7.8 Hz, 1H), 8.09 (d, J=7.7 Hz, 1H), 7.71 (d, J=5.3 Hz, 1H), 7.67 (dd, J=13.1, 2.1 Hz, 1H), 7.61 (d, J=8.5 Hz, 1H), 7.51 (t, J=7.7 Hz, 1H), 7.43 (d, J=5.3 Hz, 1H), 6.86 (t, J=9.1 Hz, 1H), 6.54 (s, 1H), 5.62 (t, J=18.3 Hz, 1H), 4.15 (dd, J=42.1, 11.0 Hz, 8H), 3.83 (s, 3H), 1.18 (dd, J=13.0, 7.0 Hz, 12H). $^{31}$P NMR (203 MHz, CDCl$_3$) δ 17.06. $^{13}$C NMR (126 MHz, CDCl$_3$) δ 165.4, 161.4, 159.7, 155.9 (t, J=3.78 Hz), 152.9, 150.9, 144.0 (d, J=11.34 Hz), 138.1, 134.6, 132.5 (t, J=10.08 Hz), 130.9, 129.8, 128.8, 127.0, 125.3, 116.2 (d, J=2.52 Hz), 114.2, 113.5 (d, J=2.52 Hz), 109.5 (d, J=22.68 Hz), 63.7 (m), 56.6, 46.8 (t, J=148.7 Hz), 16.3 (m). MS (ESI$^+$): (m/z) [M+H]$^+$ 681.42; MS (ESI$^-$): (m/z) [M−H]$^-$ 679.30

After deprotection of the above tetraethyl ester intermediate, compound I-42 was isolated as a white solid (15.8 mg, 57%).

$^1$H NMR (400 MHz, DMSO-d$_6$) δ 10.46 (s, 1H), 8.96 (s, 1H), 8.63 (d, J=7.8 Hz, 1H), 8.24 (d, J=5.2 Hz, 1H), 8.05 (d, J=7.7 Hz, 1H), 7.79 (dd, J=13.8, 2.4 Hz, 1H), 7.69 (t, J=7.8 Hz, 1H), 7.55 (d, J=5.3 Hz, 2H), 7.18 (t, J=9.4 Hz, 1H), 5.60-5.44 (m, 2H), 3.84 (s, 3H). $^{31}$P NMR (162 MHz, DMSO-d$_6$) δ 13.46. HRMS (ESI−) calculated for C$_{23}$H$_{10}$FN$_{12}$P$_2$S m/z [M−H]$^-$ 567.0337; found m/z 567.0328.

Ethyl 5-((ethoxycarbonyl)amino)thiazole-4-carboxylate (intermediate 18, Scheme 3); based on literature procedures (Shu, L. et al. *Heterocycles*. 2012, 85, 1721-1726).

Anhydrous THF (10 ml) was added to a two-necked flask containing t-BuOK (546 mg, 4.86 mmol) under argon atmosphere. The mixture was cooled to −40° C. then ethyl isocyanoacetate (500 mg, 4.42 mmol) was added dropwise at such that the temperature did not exceed −35° C. Afterwards, ethoxycarbonyl isothiocyanate (609 mg, 4.64 mmol) was also added to the mixture dropwise. The resulting mixture was stirred for 1.5 hour letting the temperature free to rise to 0° C. The reaction was quenched via addition of glacial acetic acid (2.5 ml). The mixture was diluted with ethyl acetate and water, extracted twice with ethyl acetate, washed with brine and dried over sodium sulfate. The solution was concentrated under vacuo and purified by silica-gel column chromatography. The product was obtained as an orange solid (821 mg, 76%). $^1$H NMR (500 MHz, DMSO-$d_6$) δ 10.01 (s, 1H), 8.59 (s, 1H), 4.33 (q, J=7.1 Hz, 2H), 4.26 (q, J=7.1 Hz, 2H), 1.31 (t, J=7.1 Hz, 3H), 1.28 (t, J=7.1 Hz, 3H). $^{13}$C NMR (126 MHz, DMSO-$d_6$) δ 163.73, 152.59, 146.51, 145.11, 126.81, 62.73, 60.83, 14.18, 14.13. MS [ESI$^+$] m/z: 245.40 [M+H]$^+$.

Ethyl (4-carbamoylthiazol-5-yl)carbamate (intermediate 19, Scheme 3); based on literature procedures (Shu, L. et al. Heterocycles. 2012, 85, 1721-1726).

In a pressure vessel, compound 18 was dissolved in ethanol (0.8 ml) and stirred at 40° C. until all the solid was completely dissolved. To this solution water (1.6 ml) was added, followed by ammonium hydroxide (5.8 ml, 84 mmol), and then heated at 80° C. for 30 min. After cooling to room temperature, the resulting solid was collected by filtration, rinsed with several portions of water, and dried in vacuo. Product 19 was isolated as a white solid (510 mg, 71%). $^1$H NMR (500 MHz, DMSO-$d_6$) δ 10.89 (s, 1H), 8.58 (s, 1H), 7.83 (d, J=49.4 Hz, 2H), 4.23 (q, J=7.1 Hz, 2H), 1.27 (t, J=7.1 Hz, 3H). MS [ESI$^+$] m/z: 216.10 [M+H]$^+$.

3a,7a-dihydrothiazolo[5,4-d]pyrimidine-5,7(4H,6H)-dione (intermediate 20, Scheme 3); based on literature procedures (Shu, L. et al. Heterocycles. 2012, 85, 1721-1726).

A round-bottom flask was charged with t-BuOK (625.6 mg, 5.58 mmol) and N,N-dimethylacetamide (10 mL), followed by compound 19 (400 mg, 1.86 mmol). The mixture was stirred at 100° C. under argon atmosphere for 1 hour. The reaction was then cooled to room temperature and filtered. The residue was rinsed with water and dried in vacuo. The product was isolated as an off-white solid (267 mg, 85%). $^1$H NMR (500 MHz, DMSO-$d_6$) δ 11.97 (s, 1H), 11.29 (s, 1H), 8.71 (s, 1H). MS (ESI+): (m/z) [M+H]$^+$ 170; MS (ESI$^-$): (m/z) [M−H]$^-$ 167.98

5,7-dichlorothiazolo[5,4-d]pyrimidine (intermediate 21, Scheme 3); based on literature procedure by Arnott, E. A. et al. J. Org. Chem. 2011, 76, 1653-1661.

A two-necked flask with a condenser was charged with compound 20 (500 mg, 2.96 mmol) and purged with argon. Phosphorus oxychloride (4.1 mL, 44.34 mmol) was then added at RT followed by the slow addition of DIPEA (0.7 ml, 3.84 mmol). The mixture was stirred at RT for 1 h and then heated to 95° C. for 2.5 h. Phosphorus oxychloride was then distilled off. The oily residue was then dissolved in ethyl acetate and washed with aqueous sodium bicarbonate (2×). Organic layer were collected, dried with sodium sulfate and concentrated in vacuo. The product was isolated as an off-white solid (353 mg, 58%). $^1$H NMR (400 MHz, DMSO-$d_6$) δ 9.70 (s, 1H). MS [ESI$^+$] m/z: 205.97 and 207.93 [M+H]$^+$.

5-chloro-N-(2,4-dimethoxybenzyl)thiazolo[5,4-d]pyrimidin-7-amine (intermediate 22, Scheme 3)

A mixture of compound 21 (1.00 g, 4.85 mmol), dimethoxybenzylamine (1.06 g, 6.31 mmol) and DIPEA (1.27 mL, 7.28 mmol) in DMSO (13 mL) was stirred at rt for 3 h. The mixture was poured into water (55 mL), cooled at 0° C. for 20 min and then filtered. The solid obtained was washed with water. The product was then dried in vacuo. Crude product was purified by silica-gel column chromatography and isolated as a light yellow solid. $^1$H NMR (500 MHz, CDCl$_3$) δ 8.66 (s, 1H), 7.30 (d, J=8.1 Hz, 1H), 6.81 (s, 1H), 6.44 (d, J=10.7 Hz, 2H), 4.73 (d, J=5.8 Hz, 2H), 3.84 (s, 3H), 3.80 (s, 3H). $^{13}$C NMR (126 MHz, CDCl$_3$) δ 161.9, 160.9, 158.8, 156.9, 156.3, 150.6, 131.0, 130.1, 117.7, 104.0, 98.7, 55.49, 55.46, 40.5. MS [ESI$^+$] m/z: 337.15 and 339.14 [M+H]$^+$.

Synthesis for building blocks for the preparation of purine-based (Scheme 4) and pyrrolopyrimidine-based (Scheme 5) compounds, examples include, but are not limited to examples I-44 and I-45, respectively, in Table 2

Synthesis of 2,6-dichloro-7H-purine (27, Scheme 4) was based on literature procedures with minor modifications (for an example, refer to Zheng, Q. et al. Org. Proc. Res. Dev., 2004, 8, 962-963.

Xanthine (26, 1.00 g, 6.58 mmol) and POCl$_3$ (6.20 mL, 66.8 mmol) were mixed at room temperature and then slowly heated to 50° C. under argon. To the reaction mixture, DBU (5.96 mL, 39.9 mmol) was added drop-wise under vigorous stirring. The mixture was heated to reflux (108° C.) for 6 h (after 120 min all of xanthine was dissolved, and the reaction mixture formed a brown solution). Then the reaction mixture was cooled to 50° C. and slowly transferred to ice-water (70 g) under vigorous stirring. The brown solution obtained was neutralized to pH=4 with 50% aqueous NaOH solution and then filtered through a pad of Celite. The light yellow aqueous solution was extracted with ethyl acetate (2×40 mL). The organic extracts were combined and concentrated under vacuum. Compound 27 (432 mg, 35% yield) was obtained as a yellow solid. $^1$H-NMR (400 MHz, DMSO-$d_6$): δ 8.74 (s, 1H). MS (m/z): [M]$^+$ 189.01

Synthesis of 2,6-dichloro-7-methyl-7H-purine (28) and 2,6-dichloro-9-methyl-9H-purine (29, (Scheme 4)

To a solution of dichloropurine 27 (1.36 g, 7.20 mmol) was dissolved in acetone (22.7 mL) and potassium carbonate (1.49 mg, 10.8 mmol) was added at room temperature. Methyl iodide (537 μl, 8.67 mmol) was added and the mixture was stirred for 1.5 h at room temperature. The reaction mixture was concentrated, water was added to the residue and stirred for 5 min, and then extracted with ethyl acetate (2×100 ml). The combined organic layers were dried on MgSO$_4$, filtered and concentrated under reduced pressure. The crude residue was purified by column chromatography. Compound 29 was the major product formed (952 mg, 65%) and was obtained as off-white solid and compound 28 was the minor product (389 mg, 27%) also isolated pure as an off-white solid; these results are consistant with the literature (for example WO 2010/034706) Compound 29: $^1$H-NMR (400 MHz, CDCl$_3$) δ 8.01 (s, 1H), 3.91 (s, 3H). MS (m/z): [M]$^+$ 203.05. Compound 28: $^1$H-NMR (400 MHz, CDCl$_3$) δ 8.20 (s, 1H), 4.16 (s, 3H). MS (m/z): [M]$^+$ 203.05.

Synthesis of 2-chloro-N-(2,4-dimethoxybenzyl)-9-methyl-9H-purin-6-amine (intermediate 30, Scheme 4)

A solution of compound 29 (1.21 g, 5.96 mmol) in DMSO (15 mL) and 2,4-dimethoxybenzylamine (1.16 mL, 7.74 mmol) was added DIPEA (1.78 mL, 8.91 mmol) at room temperature and stirred at 6 h at the same temperature. To the reaction mixture was added H$_2$O (20 mL) and shaken well, a white precipitate was observed. Cooled the mixture at 0° C. for 20 min filtered through the filter paper and the solid was washed with water (3×). The precipitate was dried to obtain 30 (1.79 g, 90%) as a white solid.

$^1$H-NMR (400 MHz, CD$_3$OD) δ 7.97 (s, 1H), 7.25 (d, J=8.2 Hz, 1H), 6.55 (d, J=2.3 Hz, 1H), 6.51-6.39 (m, 1H), 4.65 (s, 2H), 3.85 (s, 3H), 3.77 (s, 3H), 3.75 (s, 3H); LCMS (m/z) [M+H]$^+$333.24.

Synthesis of 1,7-dihydro-2H-pyrrolo[2,3-d]pyrimidine-2, 4(3H)-dione (intermediate 33, Scheme 5) was based on literature procedures (Hatcher, J. M. et al. *ACS Med. Chem. Lett.* 2015, 6, 584-589); it would be obvious to chemists that the tautomer of 33 is 7H-pyrrolo[2,3-d]pyrimidine-2,4-diol]

To a suspended solution of 6-aminouracil (32, 6.35 g, 50.0 mmol) and sodium acetate (4.10 g, 50.0 mmol) in H$_2$O (50 mL) at a temperature of 72° C. was added a solution of chloroacetaldehyde (50% in water, 11.8 g, 75.2 mmol) drop-wise. The reaction mixture was heated to 80° C. and stirring was continued for 60 min. After cooling the reaction mixture to room temperature, the resulting solid was collected by filtration, washed with water and acetone, and dried under vacuum to afford 33 as a light-brown solid (6.46 g, 86%). $^1$H-NMR (400 MHz, DMSO-d$_6$) δ 11.45 (s, 1H), 11.10 (s, 1H), 10.48 (s, 1H), 6.64-6.51 (m, 1H), 6.22 (t, J=2.5 Hz, 1H); MS (m/z) [M+H]$^+$ 152.06.

Synthesis of 2,4-dichloro-7H-pyrrolo[2,3-d]pyrimidine (34, Scheme 5)

To a suspension of 33 (5.75 g, 38.0 mmol) in toluene (30 mL) under argon, was added POCl$_3$ (10.6 mL, 114 mmol). To the mixture DIPEA (13.3 mL, 76.1 mmol) was added drop-wise over a period of 2.5 h at 70° C., and then the temperature was increased to 108° C. and stirring continued for 14 h. The reaction mixture was cooled to room temperature and then poured into a mixture of 150 mL ethyl acetate and 200 mL ice cold water, and then filtered through a pad of Celite. The aqueous layer was extracted with ethyl acetate (3×200 mL) and the combined organic layers were washed with brine and concentrated to give the 34 (3.42 g, 48%) as a light-brown solid. $^1$H-NMR (400 MHz, DMSO-d$_6$) δ 12.79 (s, 1H), 7.94-7.24 (m, 1H), 6.66 (ddd, J=5.3, 3.5, 1.7 Hz, 1H); MS (m/z): [M$^+$] 188.03.

Synthesis of 2,4-dichloro-7-methyl-7H-pyrrolo[2,3-d]pyrimidine (35, Scheme 5)

To a solution of 2,4-dichloro-7H-pyrrolo[2,3-d]pyrimidine 34 (237 mg, 1.26 mmol) in CH$_3$CN (1 mL) was added NaH (33.3 mg, 1.39 mmol) portion-wise at 0° C. The reaction mixture was stirred at room temperature for 20 min until gas evolution was ceased. Methyl iodide (86.4 μl, 1.39 mmol) was added and stirred the reaction mixture for 1 h at room temperature. To the reaction mixture was added water and extracted with ethyl acetate (2×30 mL). The combined organic layers were dried over MgSO$_4$, and then concentrated under vacuum. The resultant crude residue was purified by silica-gel column chromatography to afford 35 (144 mg, 58%) as white solid. $^1$H-NMR (400 MHz, DMSO-d$_6$) δ 7.76 (d, J=3.6 Hz, 1H), 6.71 (d, J=3.6 Hz, 1H), 3.81 (s, 3H); MS: (m/z) [M+H]$^+$ 204.02.

Synthesis of 2-chloro-7-methyl-7H-pyrrolo[2,3-d]pyrimidin-4-amine (36, Scheme 5)

To a solution of 35 (40.6 mg, 0.200 mmol) in dioxane (0.4 mL) in a pressure vial was added 30% aqueous NH$_4$OH solution (1.5 mL). The mixture was heated to 90° C. and stirred for 23 h. The reaction mixture was cooled to room temperature and then concentrated under vacuum. The obtained crude residue was purified by silica-gel column chromatography to afford 24 (32.8 mg, 89%) as a white solid. $^1$H-NMR (400 MHz, DMSO-d$_6$) δ 7.45 (s, 2H), 7.11 (d, J=3.4 Hz, 1H), 6.52 (d, J=3.4 Hz, 1H), 3.64 (s, 3H); MS (m/z): [M+H]$^+$ 183.10.

Example 2: Expression and Purification of Recombinant hGGPPS

The hGGPPS enzyme was expressed and purified via a slightly modified protocol described previously (Kavanagh, et al. *J. Biol. Chem.*, 2006, 281, 22004-22012). The plasmid containing N-terminally hexahistidine-tagged human GGPPS was transformed into *E. coli* BL21 (DE3) competent cells containing kantamycin in Luria-Bertani (LB) medium and was grown overnight at 37° C. Terrific broth medium (1L) containing 1 mL of 50 mM kantamycin was inoculated with 10 mL overnight seed culture and grown at 37° C. until optical density (OD)$_{600}$ equals 1 at which point the temperature was reduced to 18° C. The culture was induced with 0.5 mM isopropyl 1-thio-β-D-galactopyranoside and allowed to shake overnight. Cells were pelleted via centrifugation and were incubated in the freezer (−20° C.) overnight or at −80° C. until frozen. The frozen cell pellet was subjected to the addition of protease inhibitor, Complete Mini-EDTA free pellet (Roche Life Science), and 20 mL of binding buffer (50 mM HEPES, 500 mM NaCl, 5 mM imidazole, 5% glycerol, 10 mM β-mercaptoethanol, pH adjusted to 7.5). The cells were then sonicated, centrifuged and filtered. The His-tagged protein was loaded onto Ni-NTA agarose column, washed with binding buffer and eluted with buffer containing (50 mM HEPES, 500 mM NaCl, 250 mM imidazole, 5% glycerol, 10 mM β-mercaptoethanol, pH adjusted to 7.5). The collected protein was further purified by gel filtration chromatography using a Superdex 200 gel column with buffer containing 10 mM HEPES, 500 mM NaCl, 5%-20% glycerol, 2 mM β-mercaptoethanol, pH adjusted to 7.5. The protein was concentrated with spin-column concentrator.

Example 3: In Vitro hGGPPS Inhibition Assay

The assay was based on a literature procedure (Kavanagh, et al. *J. Biol. Chem.*, 2006, 281, 22004-22012) with minor modifications. All assays were run in triplicate using recombinant human GGPPS (80 ng), FPP (10 μM), IPP (8.3 μM; $^3$H-IPP, 40 mCi/mmoL) in a final volume of 100 μL buffer containing 50 mM Tris pH 7.7, 2 mM MgCl$_2$, 1 mM TCEP, 5 μg/mL BSA and 0.2% (w/v) Tween 20. The enzyme and test compound were pre-incubated in the assay buffer in a volume of 80 μL at 37° C. for 10 mins. Afterwards, the substrates (FPP, IPP) were added to start the reaction, which also bring the compound, substrate, and buffer contents to the desired final concentrations as indicated above. The assay mixture was then incubated at 37° C. for 15 mins (Note: the incubation time is based from the curve determined each time a new batch of enzyme is produced). Assays were terminated by the addition of 200 μL of HCl/MeOH (1:4) and incubated for 10 min at 37° C. The mixture was then extracted with 700 μL of petroleum ether, dried through a plug of anhydrous Mg$_2$SO$_4$ and 300 μL of the dried ligroin phase was combined with 8 mL of scintillation cocktail. Finally, the radioactivity was counted using a Beckman Coulter LS6500 liquid scintillation counter.

Reagents for the Enzymatic Assay: Petroleum ether (high boiling point, 60°-80° C.) was purchased from Sigma Aldrich, liquid scintillation cocktail was purchased from MP Biomedicals (Ecolite Cat #: 882475), $^3$H-IPP was obtained from American Radiolabeled Chemicals (ART 0377A; 1 mCi/mL), and unlabeled IPP and FPP were purchased from Isoprenoids, Lc. as their tri-ammonium salts.

hGGPPS wild-type enzyme: The wild-type hGGPPS enzyme was stored at −80° C. as a 1 μg/μL stock solution in the eluent buffer (10 mM HEPES, pH 7.5, 500 mM NaCl, 5%-20% glycerol, 2.0 mM β-mercaptoethanol).

IPP solution: $^3$H-IPP was diluted with unlabeled IPP (a.k.a. cold IPP) to a specific activity of 40 mCi/mmol and 82.7 μM concentration (radiolabeled+unlabeled IPP) in 10 mM Tris pH 7.7. It was stored at −10° C., warmed to 0° C. and kept on ice during the assay.

FPP solution: FPP was dissolved and diluted to a 100 μM concentration in 10 mM Tris pH 7.7. It was stored at −10° C., warmed to 0° C. and kept on ice during the assay.

In vitro hFPPS assay was carried out based on Method 2 (M2) as previously described (Leung et al. *J. Med. Chem.*, 2013, 56, 7939-7950). Cell culture and viability assays and apoptosis in human myeloma cell lines were also based on previous procedures (Leung et al. *J. Med. Chem.*, 2013, 56, 7939-7950; Lin et al. *J. Med. Chem.*, 2012, 55, 3201-3215). Determination of total Tau and phosphorylated Tau levels in AD brain in the presence of test compounds at different concentrations and LDH assays were also conducted based on previously described procedures (de Schutter et al. *J. Med. Chem.*, 2014, 57, 5764-5776).

Results and Discussion

The results of the above biological screening assays are reported in Tables 1, 2 and 3. The initial biological screening of representative compounds of the application was carried out using a routine hGGPPS inhibition assay at a fixed concentration of 1 μM and 100 nM, in parallel with the literature compound 1 (ZOL) as the positive control. Representative examples are shown in Table 3. Selectivity against hFPPS and a full-dose $IC_{50}$ curves were determined for select compounds of Formula I (Table 3). Consistent with previous observations (Leung et al. *Bioorg. Med. Chem.*, 2013, 21, 2229-2240), substitution at C-2 or C-6 (pyrimidine numbering) with a simple phenyl group (e.g. comparative compounds C-5 and C-10) inhibit both hFPPS and hGGPPS enzymes with almost equivalent potencies. A C-5 phenyl substituted analog, on the other hand, was inactive to both enzymes (data not shown). It should also be noted that previous structure-activity relationship (SAR) studies focused on the identification of potent and selective inhibitors of hFPPS, which suggested that substitution at C-5 with other aromatic groups was unfavorable; consequently, substitution at C-5 was not explored further. Replacement of the C-2 phenyl with heterocyclic groups showed that the more lipophilic moieties [phenyl comparative compound C-5 and a corresponding C-2 thiophene comparative compound C-2 vs C-2 pyridine comparative compound C-6) have better hGGPPS activity, in general (Table 1)]. The C-2 and C-6 side chains were then expanded to optimize the binding occupancy in consideration of the larger hGGPPS active site and it was found that while the potency is almost the same, the bulkier substituents improved the selectivity to hGGPPS when positioned at C-2 (e.g. I-13 vs comparative compound C-5, Table 3). On the other hand, incorporation of the same amide substituent at the C-6 position was found detrimental to the inhibitory activity for both enzymes (e.g. comparative compound C-11 vs I-13, Table 3). Given these results, attention was focused on the C-2 position. Results for expanded analogs that contain a sulfonamide- (e.g. I-11), urea (e.g. I-7) and amide-linker bearing a variety of different substituents (e.g. phenyl-based, for example, I-5, I-13, I-18, and, heterocycles I-3 and I-14, and cycloalkyl or heterocycloalkyl, for example I-4, I-15, I-30, I-46 and I-47) resulted in compounds with good activity for inhibiting hGGPPS (Table 2).

In summary, starting from the original "hits" (for example comparative compound C-5, which is substituted with a phenyl at the C-2 of the thienopyrimidine core), selectivity was improved for inhibiting hGGPPS vs hFPPS by approximately 30-fold and 55-fold, in the case of compounds I-13 and I-6, respectively (Table 3). Many of these compounds also inhibited the proliferation of MM human cancer cells with $EC_{50}$ values in the submicromolar range (Table 3).

Example 4: Protocol for Multiple Myeloma (MM) Cell Culture and Viability Assays

Various MM cancer cell lines (Table 3 and FIGS. 5 and 6) were cultured in RPMI-1640 medium supplemented with 10% fetal bovine serum (Gibco BRL, Gaithersburg, Md.) supplemented with 2 mM L-glutamine in a 5% $CO_2$ atmosphere at 37° C. $EC_{50}$ values for each target compound were determined using a commercial MTS proliferation assay (Promega, Madison, Wis.) following the manufacturer's instructions. Briefly, compounds were diluted directly into culture medium and then applied to cells that were seeded in 96-well plates at a density 5,000 cells per well. Cells were incubated with the indicated final concentration of compound in a total media volume of 100 μl/well for 72 hours prior to the addition of the MTS reagent. Plates were incubated at 37° C. in the presence 5% $CO_2$ for 2 hours prior to recording OD490 using a Tecan Infinite M200Pro microplate reader. Results were analyzed to obtain dose-response curves and $EC_{50}$ calculations using GraphPad PRISM version 5 for the MacIntosh (GraphPad Software, San Diego, Calif.).

Example 5: Alternative Protocol for Various Cancer Cell Culture and Viability Assays (Table 4)

1) Cell Culture

NCI-ADR-RES cells were obtained from National Cancer Institute (NCI) and all other cell lines were obtained from the American Type Culture Collection (ATCC). NHBE cells were maintained in Bronchial Epithelial Cell Growth Medium (BEGM) supplemented with 10% FBS (Multicell) and 2 mM L-glutamine (Gibco/Life Technologies). All other cells were maintained in culture using Roswell Park Memorial Institute (RPMI) 1640 media supplemented with 10% FBS (Multicell), Penicillin (100 U/mL), Streptomycin (100 ug/mL) and 2 mM L-glutamine (Gibco/Life Technologies). Cells were plated in logarithmic growth phase in each well of clear bottom multiwell plates and cultured 16-24 h before drug treatment. Serial dilutions of compounds were made in DMSO before dilution in proper media and then added to cultured cells in order to reach a maximum of 0.2% DMSO. Cells were incubated with drugs for 72 hours. Information regarding the various cell lines tested is provided in the Table 4.

2) Determination of Cell Viability

Cell viability was determined by cellular quantitation of adenosine triphosphate (ATP) using the CellTiter-Glo Luminescent Cell Viability Assay Kit (Promega Corporation, Cat. No. G7571). Briefly, the CellTiter-Glo «one-mix-measure» reagent, containing both the cell permeabilizing agent and the Ultra-Glo luciferase, was added to the cell culture according to manufacturers' instructions allowing the free ATP to be released from viable cells and subsequently converted into luminescence. The luminescence generated in the reaction is directly proportional to cell viability and was quantified in a luminometer (PHERAstar FS, BMG Labtech)

3) Data Analysis

To calculate the relative growth inhibition induced by drug treatment, the mean value of relative light units (RLU) for replicate samples in the CellTiter-Glo assay at each dose was divided by the mean RLU value obtained from vehicle treated cells to give percent viability. Sigmoidal dose response curves and $IC_{50}$ values were generated using non-linear regression analysis (5 parameter fit) and GraphPad Prism Version 6 (GraphPad Software Inc., San Diego, Calif.).

4) Results

Figure 3:
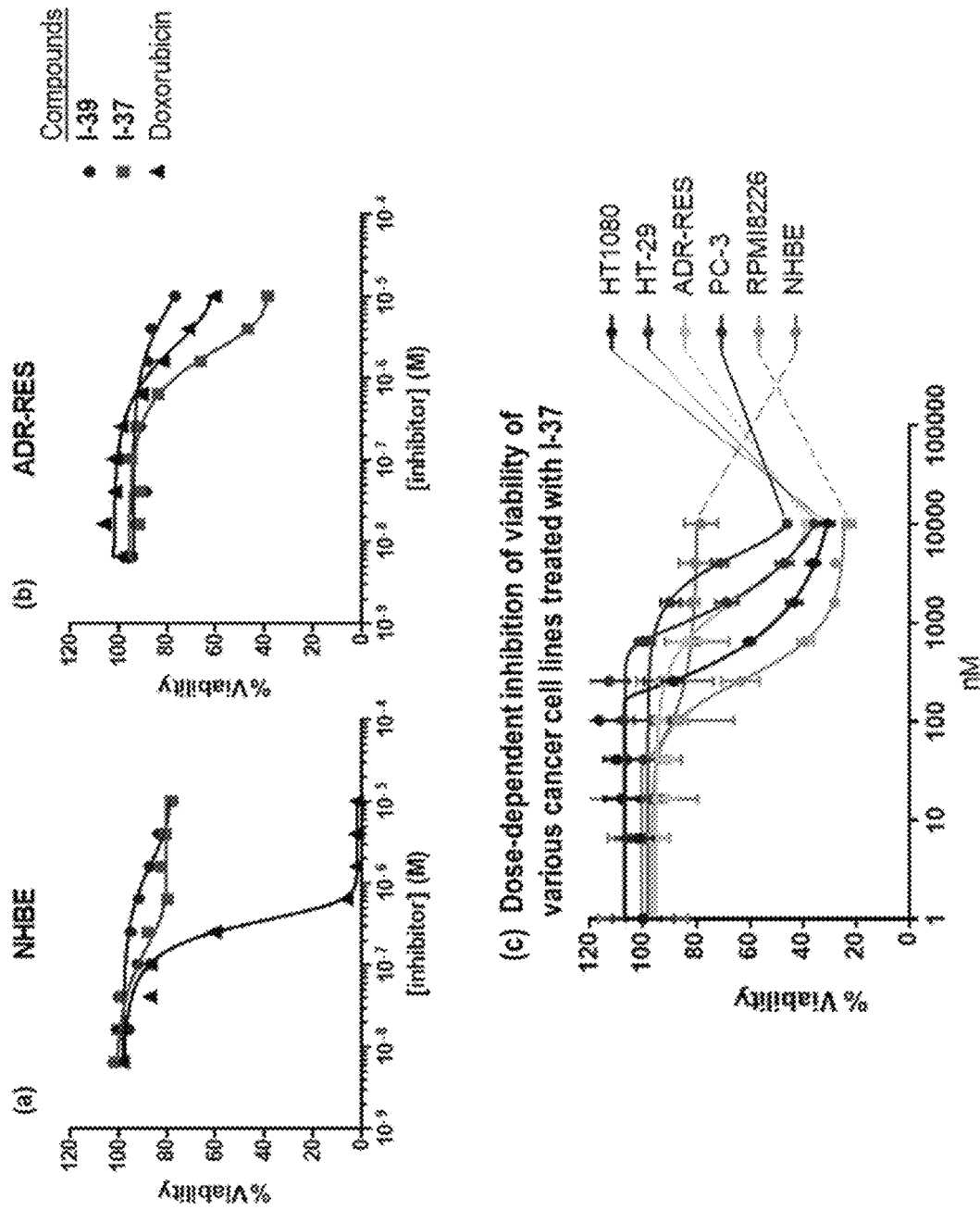
FIG. 3a,b shows a comparison of the antiproliferative effect of doxorubicin and two exemplary compounds I-37 and I-39 on (a) normal human bronchial cells (NHBE cells), (b) ovarian cancer cells expressing high levels of multi-drug resistance pumps (ADR-RES cells).
FIG. 3c shows the antiproliferative effect exemplary compounds I-37 in various cancer cell lines; the cell lines used are described in Table 4.
Figure 4:
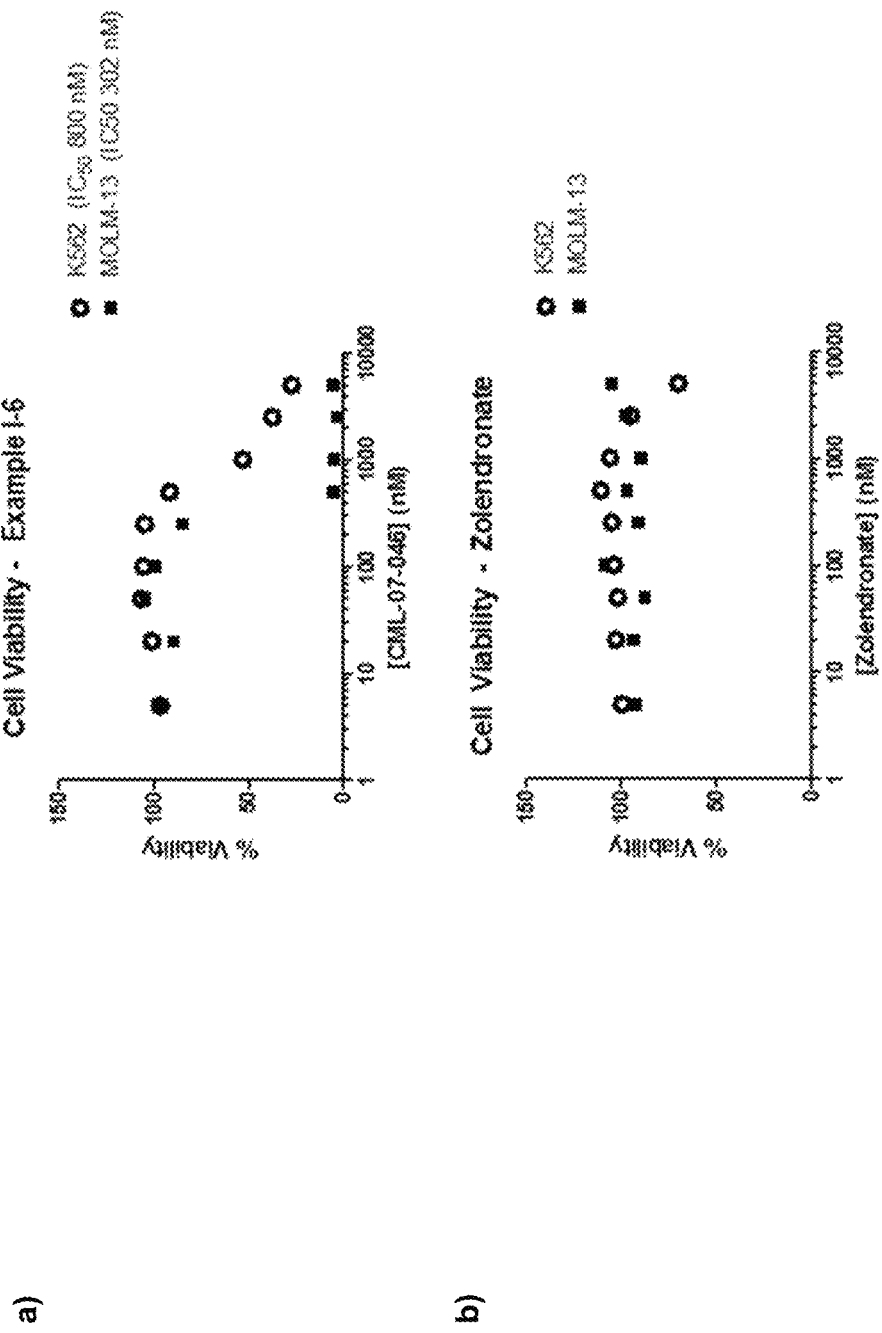
FIG. 4 shows the antitumour effects of exemplary compound I-6 and zolendronate in chronic myelogenous leukemia cells (K562) and acute monocytic leukemia cells (MOLM-13).
Figure 5:
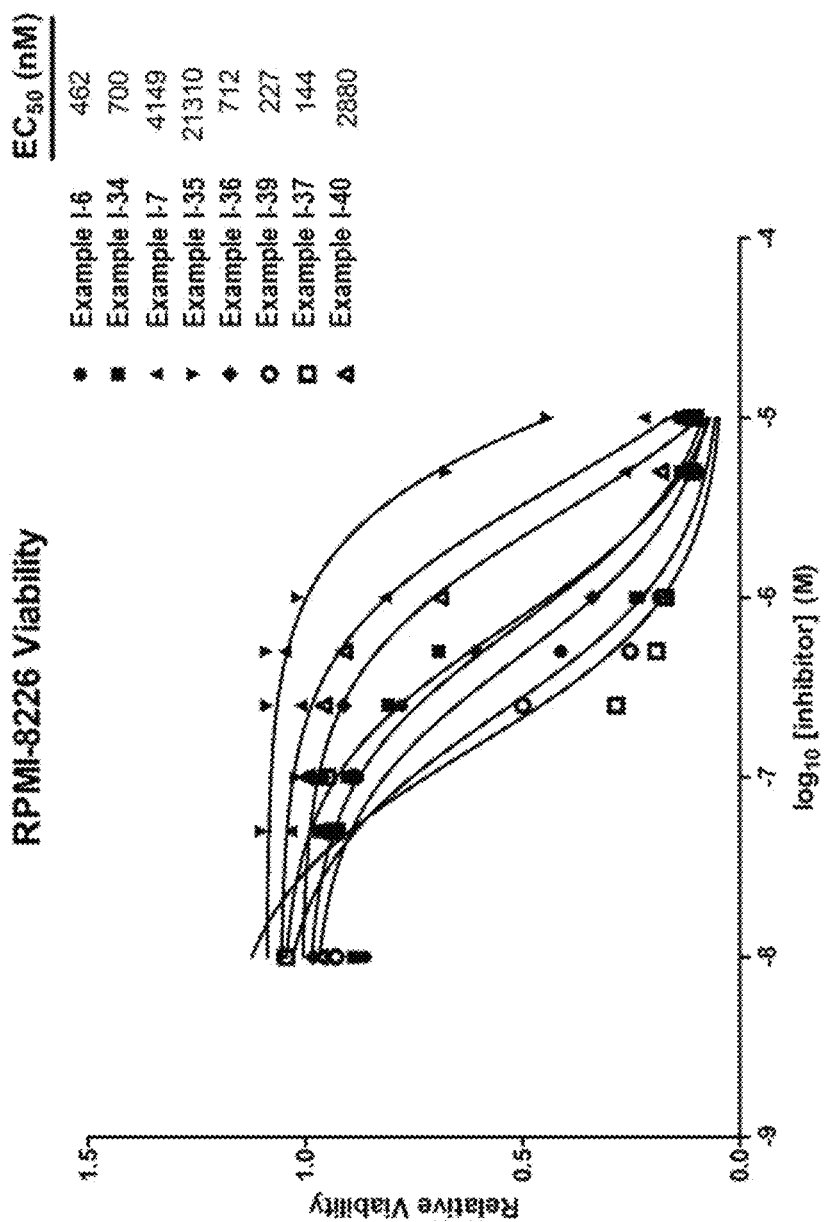
FIG. 5 shows the antitumour effects of exemplary compounds I-6, I-34, I-7, I-35, I-36, I-39, I-37, and I-40 in multiple myeloma cells (RPMI-8226).

The $EC_{50}$ values of compounds of the application are shown in FIGS. 4, and 5. FIG. 3, panels a and b indicate that compared to the common antitumour drug doxorubicin, compounds of the application, exemplified by I-37 inhibit a variety of cancer types, are less toxic to normal human bronchial cells (NHBE; FIG. 3a) and are equivalent or more effective in some cancer cell lines that are drug resistant to doxorubicin, such as ovarian cancer cells ADR-RES (FIG. 3b). Additionally, FIG. 3c shows that compounds of the application, exemplified by I-37 inhibit a variety of cancer types. The data in FIG. 4 shows that compound I-6 (panel a) is also more effective in blocking viability of cancer cells compared to zolendronate (ZOL) (panel b) for chronic myelogenous leukemia (K562) and acute monocytic leukemia (MOLM-13) cells. $EC_{50}$ values against MM cells RPMI-8226 for compounds I-6, I-34, I-7, I-35, I-36, I-39, I-37, and I-40 are shown in FIG. 5.

Example 6: Apoptosis Assay In Multiple Myeloma Cell Assay

To determine the ability of compounds of the application to induce MM cell lines to undergo apoptosis, cells were seeded at a density of $7.5 \times 10^5$/mL in medium supplemented with 10% FBS with increasing concentrations of compound (i.e. compound that inhibits hGGPPS) or vehicle alone. Following a 72 h incubation, apoptosis was determined by double staining with APC Annexin V (BD Biosciences, Mississauga ON) and eFluor 780 Viability dye (ThermoFisher Scientific) according to the manufacturer's directions. Stained samples were acquired on a BD FACSCanto II instrument (BD Biosciences, Mississauga ON) and post-acquisition analyses were performed using FlowJo (V10) software. Apoptosis of multiple myeloma cells was also determined by flow cytometry by double staining cells with Allophycocyanin (APC) conjugated Annexin V and a V450 conjugated Mouse Anti-Human CD138 monoclonal antibody, following the manufacturer's instructions (BD Biosciences, Mississauga ON).

Figure 6:
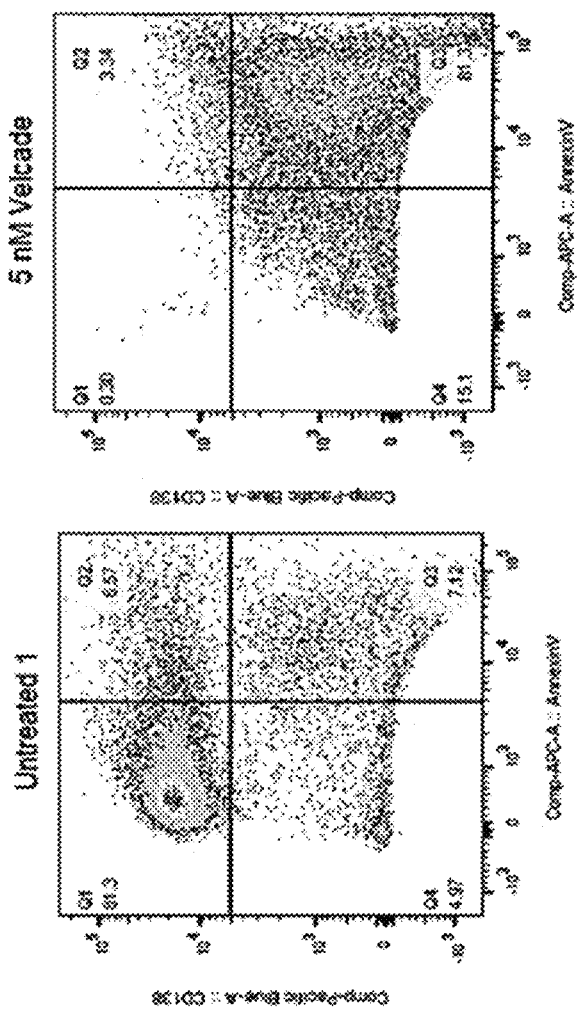
FIG. 6 shows an example of flow cytometry data for detection of cell apoptosis, using the multiple myeloma cell line RPMI-8226. Control experiments with untreated multiple myeloma cells and cells treated with the drug Vercade (a potent antitumor agent for the treatment of multiple myeloma) were run in parallel.

The apoptosis data of compound I-24 at different concentrations (100 nM, 500 nM, and 1 µM) in multiple myeloma cells are shown in FIG. 6. Untreated cells and 5 nM Velcade were used as negative and positive controls, respectively. The data demonstrate that compounds of the application can induce apoptosis. However, the MM cells could be rescued from apoptosis by the addition of geranylgeraniol (GGOH), but only when apoptosis was induced by compounds of this application, not by velcade, which has a different mechanism of action. This observations (i.e. the rescued of cells from apoptosis by the addition of GGOH as an external substitute of the missing catalytic product of hGGPPS) confirming specificity of intracellular target engagement by the compounds disclose in this application.

Example 7: Western Blot Analysis

Multiple myeloma cells were cultured in RPMI-1640 media supplemented with 10% FBS and L-glutamine and were maintained at 37° C. in 5% $CO_2$ atmosphere in the presence and absence of the indicated concentration of test compound. These experiments were performed to demonstrate intracellular down-regulation of Rap1A prenylation upon treatment with compounds of this application. Geranylgeraniol co-treatment (GGOH; 10 µM) served as a specificity control to demonstrate bypass of hGGPPS inhibitor treatment and specific target engagement in cells, which was directly associated with hGGPPS inhibition. In other words, cells could be rescued from apoptosis upon co-treatment of these cells with a hGGPPS inhibitor plus GGOH. Cells were harvested by centrifugation after the indicated treatment duration. Harvested cells were immediately washed with ice cold PBS, centrifuged, and then resuspended in ice cold RIPA lysis buffer (Pierce cat #89900). Equal amounts of cleared protein lysate were then separated by SDS-PAGE, transferred to PVDF membranes, and then membranes were incubated with primary antibody overnight at 4° C. After extensive washing, membranes were exposed to HRP-conjugated secondary antibodies for 1 hour at room temperature. Finally, after extensive washing standard chemiluminescence reagents and techniques were employed to visualize the bound secondary antibodies.

Example 8: Preclinical Profiling: Metabolic Stability in Liver Microsomes of hGGPPS Inhibitors As an example, the metabolic stability of inhibitor I-37 was evaluated in liver microsomes from three species. After incubation of the compound with liver microsomes, the parent compound and any metabolites with a bisphosphonate moiety were converted to the corresponding trimethyl silyl ester with trimethylsilyl diazomethane, following the protocol previously reported for the determination of bisphosphonate-type drug concentrations in human plasma (see: Ghassabian, S. et al. *J. Chromatogr. B* 2012, 881-882, 34-41). Samples were analyzed by LC-MS/MS using loperamide as a reference (half-life clearance of 8-15 min in all three liver microsome incubations). The half-life clearance of I-37 in male CD-1 mouse liver microsomes (MLM). Sprague-Dawley rat liver microsomes (RLM) and human liver microsomes (HLM) was found to be 128 min, 187 min and 154 min, respectively. Significantly higher lipophilicity was also observed for our thienopyrimidine hGPPS inhibitor as compare to current N-BP drugs. For example, a difference in relative retention time of more than 7 min was observed on a C-18 reversed phase HPLC column between compounds I-37 and the drug zolodronic acid, typically expected to translate into better cell-membrane permeability for compound I-37 (by passive diffusion).

Example 9: In Vivo Study (Compound I-37)

In vivo experiments were performed according to the guidelines of the Canadian Council on Animal Care and approved by the Animal Care Committee of the Research Institute of the McGill University Health Centre as per protocol number 2012-7242. Mice were all bred and maintained in a pathogen-free standard animal facility with a light/dark cycle of 12 hours and provided with food and water ad libitum. Vk*MYC/KaLwRij mice with an M-peak higher than 13% (and aged between 52 and 77 weeks) were used for this in vivo study. Mice were placed in groups of two (treated with 1 mg/kg, 5 mg/kg of I-37) and received a 17 doses (15 day treatment course with a two day drug holiday during the weekend, followed by a two day re-treatment before sacrifice [number of mice per group of 3, age and gender matched, intraperitoneal injection]. Mice were euthanized after 24 h of receiving the last dose or as instructed per protocol in case of toxicity effects. Mice were anesthetized with ketamine and terminal blood collection was achieved by cardiac puncture. At cardiac puncture, whole blood from all mice was collected in order to obtain serum and peripheral blood mononuclear cells (PBMCs).

Serum extraction: Blood was spun in a microcentrifuge at 6000 rpm for 15 minutes to obtain serum. Serum was used to run Serum Protein Electrophoresis (SPEP) and the remaining sample was stored in freezer at −80° C.

Isolation of peripheral blood mononuclear cells: Ammonium chloride was used to lyse red blood cells (RBCs) from whole blood while PBMCs were not thus lysed. Whole blood was diluted in 20 ml of ammonium chloride (155 mM $NH_4Cl$) and mixed by gentle vortexing for 10 minutes at room temperature. Cell solution was centrifuged at 400×g for 5 minutes and two washes with PBS were performed to remove ammonium chloride. PBMCs were harvested, lysed and analysed Western Blot to measure unprenylated Rap1A, following the same procedure as in the case of the MM RPMI-8226 cells described above.

Example 10: Phosphorylation of the Tau Protein

As demonstrated in FIG. 7 and Table 5, compounds disclosed in this application, exemplified by I-5, selectively inhibit hGGPPS and downregulate phosphorylation of the tau protein (P-Tau) in human immortalized neurons (SH-SYSY neurons) to a greater extent than equipotent inhibitors of hFPPS, such as compound 6-1 of WO2014/078957, in spite of structural similarities and very similar physico-chemical properties such as Clog P values. Compared to zoledronic acid, the hGGPPS-selective I-5 is equally effective at reducing tau protein phosphorylation but exhibits much lower toxicity (Table 5). Table 5 contains inhibition data reflecting the decrease in phosphorylated Tau protein to Total Tau protein levels in immortalized human neurons (SH-SYSY) treated with prior art compound 6-1 (an hFPPS inhibitors of WO2014/078957) compared to the exemplary hGGPPS inhibitor compound 6-I-5 of the present application and their corresponding toxicity data to these cells based on LDH toxicity. The experimental details for these types of assays were previously reported by De Schutter et al. *J. Med. Chem.* 2014, 57, 5764-5776.

Different embodiments of the application have been shown by the above example. Those skilled in the art could develop alternatives to the methods mentioned above that are within the scope of the application and defined claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Structures and Activity Data for hGGPPS Inhibition for Comparative and Reference Compounds

| Example | STRUCTURE | hGGPPS $IC_{50}$ (µM) |
|---|---|---|
| Literature Compound 1 (mixture of E/Z isomers) Positive control | 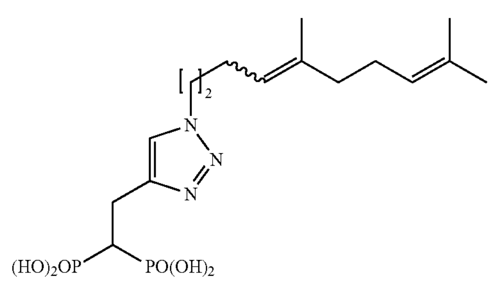 | A |
| Zolendronic acid (ZOL) | 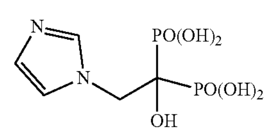 | C |
| Risedronic acid RIS | 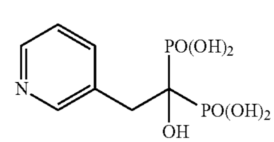 | C |

TABLE 1-continued
Structures and Activity Data for hGGPPS Inhibition for Comparative and Reference Compounds
| Example | STRUCTURE | hGGPPS IC$_{50}$ (μM) |
|---|---|---|
| C-1 | 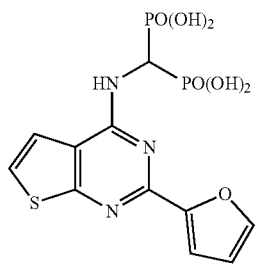 | B |
| C-2 | 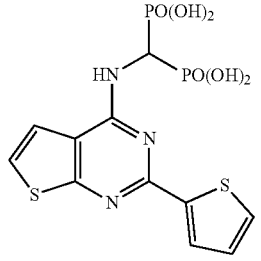 | A |
| C-3 | 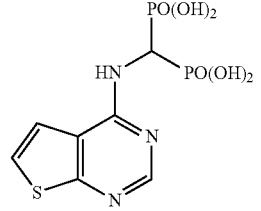 | C |
| C-4 | 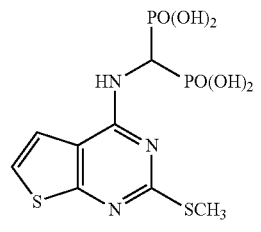 | C |
| C-5 | 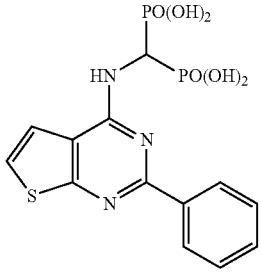 | A |

TABLE 1-continued

Structures and Activity Data for hGGPPS Inhibition for Comparative and Reference Compounds

| Example | STRUCTURE | hGGPPS IC$_{50}$ (μM) |
|---|---|---|
| C-6 | 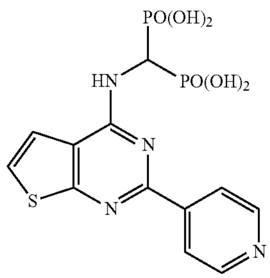 | B |
| C-7 | 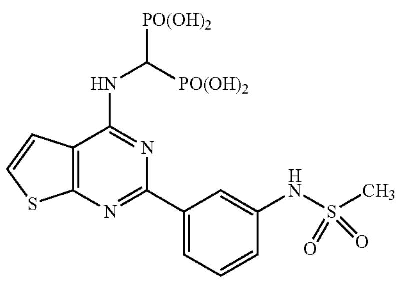 | B |
| C-9 | 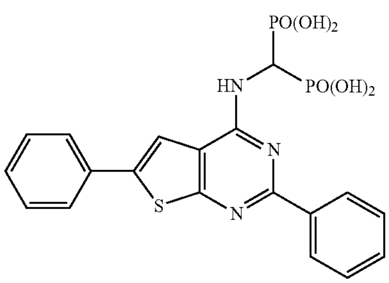 | B |
| C-10 | 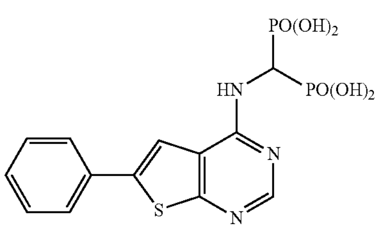 | A |
| C-11 | 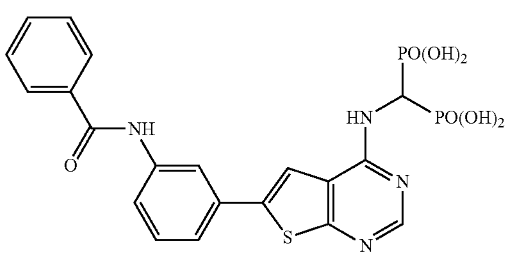 | C |

TABLE 1-continued

Structures and Activity Data for hGGPPS Inhibition for Comparative and Reference Compounds

| Example | STRUCTURE | hGGPPS IC$_{50}$ (µM) |
|---|---|---|
| C-12 | 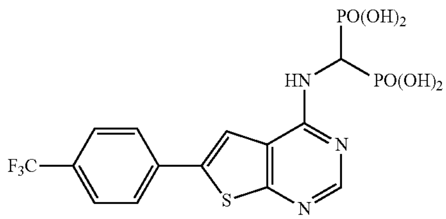 | B |
| C-13 | 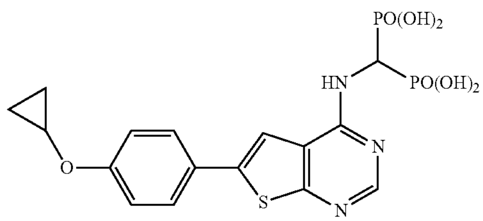 | B |

A: IC$_{50}$ = ≤0.1 µM;
B: 0.1-5 µM;
C: IC$_{50}$ = ≥5 µM;
ND = not determined

TABLE 2

Activity Data for hGGPPS Inhibition For Representative Compounds of Formula I

| I-1 | | A |
|---|---|---|
| I-2 | 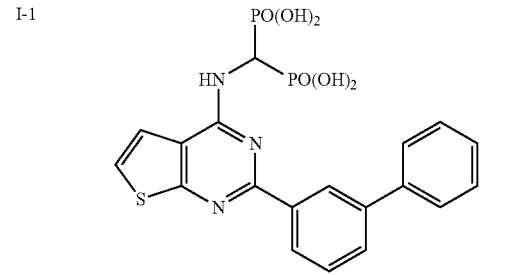 | B |
| I-3 | 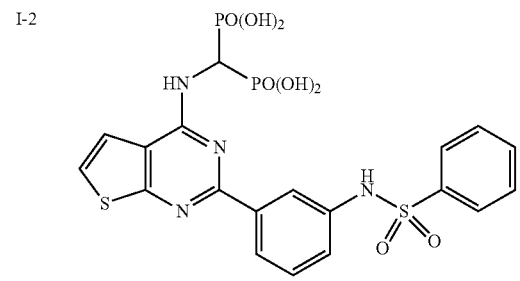 | A |

TABLE 2-continued

Activity Data for hGGPPS Inhibition For Representative Compounds of Formula I

| I-4 | 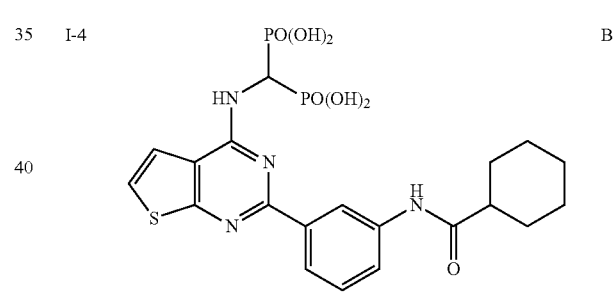 | B |
|---|---|---|
| I-5 | 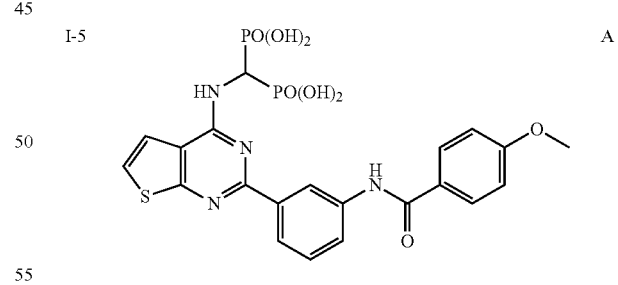 | A |
| I-6 | 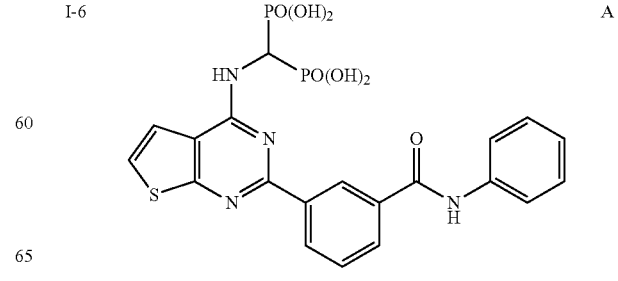 | A |

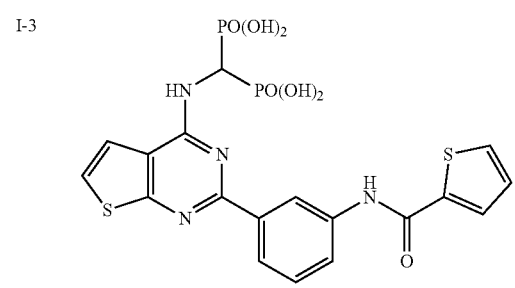

TABLE 2-continued

Activity Data for hGGPPS Inhibition For Representative Compounds of Formula I

| Compound | Structure | Activity |
|---|---|---|
| I-7 | thieno[2,3-d]pyrimidine with 4-NH-CH(PO(OH)₂)₂ and 2-(3-(3-(4-fluorophenyl)ureido)phenyl) | A |
| I-8 | thieno[2,3-d]pyrimidine with 4-NH-CH(PO(OH)₂)₂ and 2-(biphenyl-4-yl) | A |
| I-9 | thieno[2,3-d]pyrimidine with 4-NH-CH(PO(OH)₂)₂ and 2-(3-(4-isopropoxyphenyl)phenyl) | A |
| I-10 | thieno[2,3-d]pyrimidine with 4-NH-CH(PO(OH)₂)₂ and 2-(4-(phenylsulfonamido)phenyl) | B |
| I-11 | thieno[2,3-d]pyrimidine with 4-NH-CH(PO(OH)₂)₂ and 2-(4-(4-methylphenylsulfonamido)phenyl) | B |
| I-12 | thieno[2,3-d]pyrimidine with 4-NH-CH(PO(OH)₂)₂ and 2-(4-benzamidophenyl) | B |
| I-13 | thieno[2,3-d]pyrimidine with 4-NH-CH(PO(OH)₂)₂ and 2-(3-benzamidophenyl) | A |
| I-14 | thieno[2,3-d]pyrimidine with 4-NH-CH(PO(OH)₂)₂ and 2-(3-(picolinamido)phenyl) | B |
| I-15 | thieno[2,3-d]pyrimidine with 4-NH-CH(PO(OH)₂)₂ and 2-(3-(cyclopropanecarboxamido)phenyl) | B |
| I-16 | thieno[2,3-d]pyrimidine with 4-NH-CH(PO(OH)₂)₂ and 2-(3-(2-methylbenzamido)phenyl) | B |

TABLE 2-continued
Activity Data for hGGPPS Inhibition For Representative Compounds of Formula I
| | | |
|---|---|---|
| I-17 | 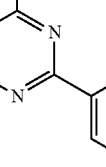 | B |
| I-18 | 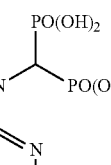 | A |
| I-19 | 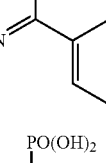 | A |
| I-20 | 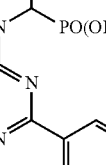 | B |
| I-21 | 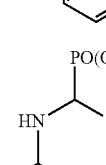 | A |
| I-22 | 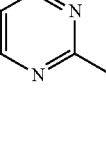 | A |
| I-23 | 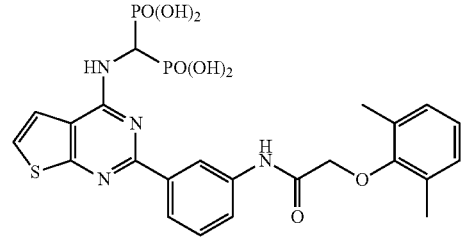 | A |
| I-24 | 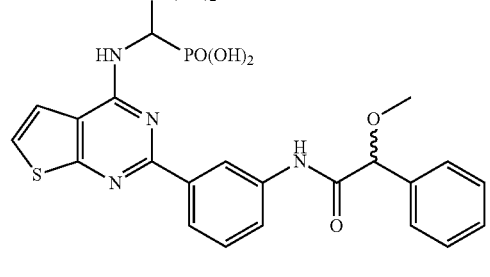 | A |
| I-25 | 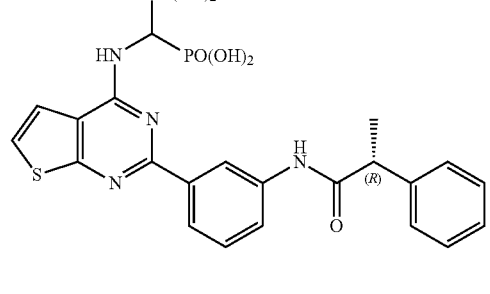 | A |
| I-26 | 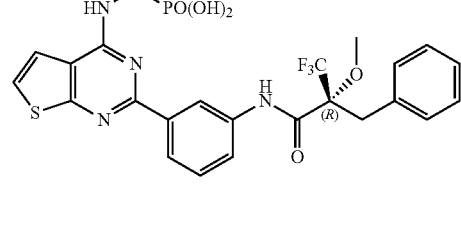 | B |
| I-27 | 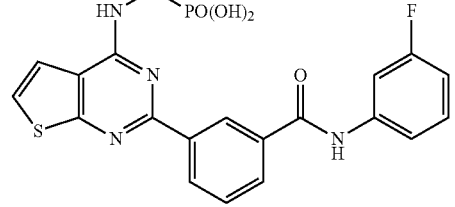 | A |

TABLE 2-continued

Activity Data for hGGPPS Inhibition For Representative Compounds of Formula I

| ID | Structure | Activity |
|---|---|---|
| I-28 | thieno[2,3-d]pyrimidine with 4-[NH-CH(PO(OH)$_2$)$_2$] and 2-[3-(C(O)NH-3,5-dimethylphenyl)phenyl] | A |
| I-29 | thieno[2,3-d]pyrimidine with 4-[NH-CH(PO(OH)$_2$)$_2$] and 2-[3-(C(O)-piperidin-1-yl)phenyl] | B |
| I-30 | thieno[2,3-d]pyrimidine with 4-[NH-CH(PO(OH)$_2$)$_2$] and 2-[3-(C(O)-(4-phenylpiperidin-1-yl))phenyl] | A |
| I-31 | thieno[2,3-d]pyrimidine with 4-[NH-CH(P(O)(OEt)(OH))$_2$] and 2-[3-(C(O)NH-phenyl)phenyl] | C |
| I-32 | thieno[2,3-d]pyrimidine with 4-[NH-CH(PO(OH)$_2$)$_2$] and 2-[3-(NH-C(O)-CH$_2$-pyridin-3-yl)phenyl] | B |
| I-33 | thieno[2,3-d]pyrimidine with 4-[NH-CH(PO(OH)$_2$)$_2$] and 2-[3-(NH-C(O)-quinolin-3-yl)phenyl] | A |
| I-34 | thieno[2,3-d]pyrimidine with 4-[NH-CH(PO(OH)$_2$)$_2$] and 2-[3-(NH-C(O)-4-fluorophenyl)phenyl] | A |
| I-35 | thieno[2,3-d]pyrimidine with 4-[NH-CH(PO(OH)$_2$)$_2$] and 2-[3-(NH-C(O)-(5-CF$_3$-pyridin-2-yl))phenyl] | A |
| I-36 | thieno[2,3-d]pyrimidine with 4-[NH-CH(PO(OH)$_2$)$_2$] and 2-[3-(NH-C(O)-4-CF$_3$-phenyl)phenyl] | A |
| I-37 | thieno[2,3-d]pyrimidine with 4-[NH-CH(PO(OH)$_2$)$_2$] and 2-[3-(C(O)NH-(3-fluoro-4-methoxyphenyl))phenyl] | A |
| I-38 | thieno[2,3-d]pyrimidine with 4-[NH-CH(PO(OH)$_2$)$_2$] and 2-[3-(C(O)NH-benzothiazol-2-yl)phenyl] | B |

TABLE 2-continued
Activity Data for hGGPPS Inhibition For Representative Compounds of Formula I
| | | |
|---|---|---|
| I-39 | 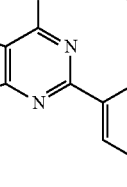 | A |
| I-40 | | B |
| I-41 | | A |
| I-42 | | A |
| I-43 | | A |
| I-44 | | B |
| I-45 | 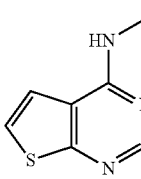 | B |
| I-46 | | A |
| I-47 | | B |
| I-48 | | B |
A: $IC_{50} = \leq 0.1\ \mu M$;
B: $0.1\text{-}5\ \mu M$;
C: $IC_{50} = \geq 5\ \mu M$;
ND = not determined

TABLE 3

Potency and Selectivity of Select Compounds

| Compound | PPS IC$_{50}$ (μM) | GGPPS IC$_{50}$ (μM)[a] | Ratio of hFPPS IC$_{50}$ vs hGGPPS IC$_{50}$ | MM cells EC$_{50}$, μM[b] | | |
|---|---|---|---|---|---|---|
| | | | | JJN3 | RPMI-8226 | KMS28PE |
| ZOL | 0.004[c] | >50 | >1 × 10$^{-4}$ | 5.0 | 11.0 | 6.4 |
| RIS | 0.011 | ~350[d] | >3 × 10$^{-4}$ | 10.0 | 13.0 | 10.6 |
| C-5 | 0.54 | 0.082 | ~7 | nd | nd | nd |
| C-10 | 0.20 | 0.094 | ~2 | nd | nd | nd |
| C-11 | >10 | >10 | nd | nd | >10 | nd |
| C-12 | 0.023 | ~10,000 | >4 × 10$^{-5}$ | >10 | >50 | nd |
| C-13 | 0.014 | ~10,000 | >7 × 10$^{-5}$ | >10 | >50 | nd |
| I-13 | 2.0 | 0.064 | 31 | 0.50 | 0.10 | 0.55 |
| I-18 | 2.4 | 0.10 | 24 | 0.60 | 0.12 | 0.62 |
| I-5 | 1.0 | 0.085 | 12 | 1.30 | 0.38 | 1.4 |
| I-6 | 3.0 | 0.053 | 57 | 0.34 | 0.11 | 0.70 |
| I-36 | 2.6 | 0.10 | 26 | 0.70 | 0.71 | nd |
| I-37 | 1.4 | 0.086 | 16 | 0.51 | 0.15 | 0.17 |
| I-42 | nd | 0.085 | — | nd | 0.20 | nd |
| I-43 | nd | 0.065 | — | nd | 0.14 | nd |

[a]IC$_{50}$ values were determined using the wild-type hGGPPS enzyme, average of n ≥ 3 determinations;
[b]Average of n ≥ 8 determinations, R$^2$ values in the range of 0.94-0.99;
[c]IC$_{50}$ value from Kavanagh et. al. *Proc. Natl. Acad. Sci.* 2006, 103, 7829-7834;
[d]IC$_{50}$ value from Szabo et. al. *J. Med. Chem.* 2002, 45, 2185-2196.
nd = not determined

TABLE 4

Cell Lines Used in Viability Assays

| Cell Lines | Cancer or Normal | KRAS Status |
|---|---|---|
| HT1080 | Fibrosarcoma | Activated (NRAS) |
| HT-29 | Colorectal | Wt KRAS overexpression |
| MiaPaCa-2 | Pancreatic | Mutated |
| HCT-116 | Colorectal | Mutated |
| T98G | Brain | |
| MDA-MB-231 | Breast | Mutated |
| A549 | Non small cell lung | Mutated |
| ADR-RES | Ovarian | Express high levels of multiple drug resistant pumps |
| PC-3 | Prostate | |
| NHBE | Human bronchial cells (normal) | |
| RPMI-8226 | Multiple myeloma | |

TABLE 5

| Compounds | Reduction in P-Tau/Total-tau protein | LDH Toxicity Assay (relative toxicity compared to the control samples) |
|---|---|---|
| Zoledronic acid | 50% | Very high |
| | 9% | None observed |
| | 43% | None observed |

The invention claimed is:

1. A compound of Formula I, or a pharmaceutically acceptable salt, solvate and/or prodrug thereof:

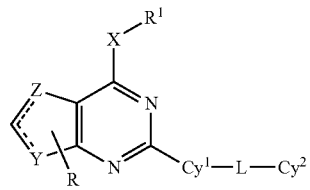

(I)

wherein:
R is selected from H, $C_{1-2}$alkyl and $C_{1-2}$fluoroalkyl;
$R^1$ is $(CR^5R^{5'})PO(OR^6)_2$, wherein $R^5$ is selected from $PO(OR^{6'})_2$, $CO_2R^{6'}$, $C(O)NHR^7$, $SO_3R^7$ and $SO_2NHR^7$; $R^{5'}$ is selected from H, OH and halo; $R^6$ and $R^{6'}$ are independently selected from H and $C_{1-6}$alkyl; and $R^7$ is selected from H, OH and $C_{1-6}$alkyl;
X is selected from O, $CH_2$, NH and $N(C_{1-4}$alkyl);
Z and Y are independently selected from S, O, $NR^3$ and $CR^3R^{3'}$;
$Cy^1$ is selected from $C_{6-10}$aryl, $C_{5-10}$heteroaryl, $C_{3-10}$cycloalkyl and $C_{3-10}$heterocycloalkyl, each of which are unsubstituted or substituted with one or two substituents independently selected from halo, cyano, hydroxyl, $NH_2$, $NHC_{1-6}$alkyl, $NHC_{3-6}$cycloalkyl, $N(C_{1-6}$alkyl)($C_{1-6}$alkyl), $C_{1-6}$fluoroalkyl, $C_{1-6}$alkyl, $C_{3-6}$cycloalkyl, $C_{1-6}$fluoroalkoxy, $C_{3-6}$cycloalkoxy and $C_{1-6}$alkoxy;
$Cy^2$ is selected from $C_{3-10}$cycloalkyl, $C_{3-10}$heterocycloalkyl, $C_{6-10}$aryl and $C_{5-10}$heteroaryl, each of which is unsubstituted or substituted with one to three substituents independently selected from halo, cyano, hydroxyl, $NH_2$, $NHC_{1-6}$alkyl, $NHC_{3-6}$cycloalkyl, $N(C_{1-6}$alkyl)($C_{1-6}$alkyl), $C_{1-6}$fluoroalkyl, $C_{1-6}$alkyl, $C_{3-6}$cycloalkyl, $C_{1-6}$fluoroalkoxy, $C_{3-6}$cycloalkoxy, phenyl, $C_{3-6}$heterocycloalkyl, $C_{5-6}$heteroaryl and $C_{1-6}$alkoxy;
L is selected from a direct bond, C(O), O, AC(O) $(CR^4R^{4'})_m(A')_p$, $ASO_2(CR^4R^{4'})_m(A')_p$, C(O)A $(CR^4R^{4'})_m(A')_p$ and $SO_2A(CR^4R^{4'})_m(A')_p$;
$R^3$ and $R^{3'}$ are independently selected from H, $C_{3-6}$cycloalkyl and $C_{1-4}$alkyl, or when the atom to which $R^3$ is attached is sp$_2$ hybridized, $R^3$ is not present;
$R^4$ and $R^{4'}$ are independently selected from H, halo, $C_{1-4}$fluoroalkyl, $C_{1-4}$alkyl, $C_{3-6}$cycloalkyl, $C_{1-4}$fluoroalkoxy, $C_{3-6}$cycloalkoxy and $C_{1-4}$alkoxy;
m is selected from 0, 1 and 2;
p is selected from 0 and 1;
A is selected from NH and N($C_{1-4}$ alkyl);
A' is selected from O, NH and N($C_{1-4}$ alkyl) when m is 1 or 2 and A' is selected from NH and N($C_{1-4}$ alkyl) when m is 0; and ---- represents a single or double bond, provided that two double bonds are not adjacent to each other.

2. The compound of claim 1, wherein R is H.

3. The compound of claim 1, wherein $R^1$ is $(CR^5R^{5'})PO(OR^6)_2$, wherein $R^5$ is selected from $PO(OR^{6'})_2$, $CO_2R^{6'}$, $C(O)NHR^7$, $SO_3R^7$ and $SO_2NHR^7$; $R^{5'}$ is H; $R^6$ and $R^{6'}$ are independently selected from H and $CH_3$; and $R^7$ is selected from H, OH and $CH_3$.

4. The compound of any one of claim 1, having the following structure:

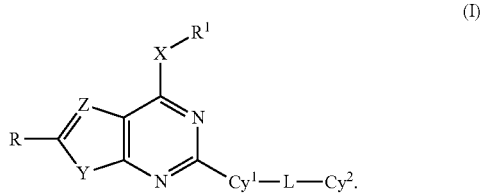

5. The compound of claim 1, wherein the bicyclic core is selected from:

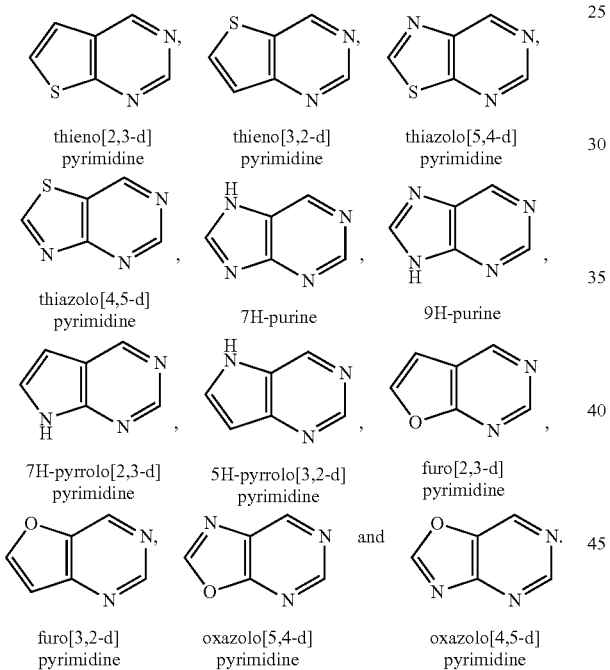

6. The compound of claim 1, wherein, $Cy^1$ is selected from phenyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridinyl, pyrazinyl, pyrimidinyl, triazinyl, pyrrolidinyl, piperazinyl, piperidinyl, morpholinyl and pyridazinyl, each of which is unsubstituted or substituted with one or two substituents.

7. The compound of claim 1, wherein L is selected from a direct bond, C(O), O, $AC(O)(CR^4R^{4'})_m(A')_p$, $ASO_2(CR^4R^{4'})_m(A')_p$, $C(O)A(CR^4R^{4'})_m(A')_p$ and $SO_2A(CR^4R^{4'})_m(A')_p$.

8. The compound of claim 1, wherein $R^4$ and $R^{4'}$ are independently selected from H, F, Cl, $CF_3$, $CH_3$, $CF_3O$ and $CH_3O$.

9. The compound of claim 1, wherein at least one of $R^4$ and $R^{4'}$ is H.

10. The compound of claim 1, wherein A' is O or NH when m is 1 or 2 and A' is selected from NH and $NCH_3$ when m is 0.

11. The compound of claim 1, wherein $Cy^2$ is selected from phenyl, naphthyl, cyclopropyl, cyclobutyl, cyclopentyl, cyclohexyl, 5-membered heteroaryl, 6-membered heteroaryl, 10-membered heteroaryl, 5-membered heterocycloalkyl and 6-membered heterocycloalkyl.

12. The compound of claim 1, wherein $Cy^1$ is unsubstituted or substituted one substituent selected from Cl, F, $NHCH_3$, $N(CH_3)_2$, $CF_3$, $CH_3$, $CH_3CH_2$, $(CH_3)_2CH_2$, $CH_3O$, $CH_3CH_2O$, $(CH_3)_2CH_2O$, $CF_3O$ and $CF_3O$.

13. The compound claim 1, wherein $Cy^2$ is unsubstituted or substituted with 1-3 substituents independently selected from Cl, F, phenyl, cyano, hydroxyl, $NH_2$, $NHCH_3$, $N(CH_3)_2$, $C_{1-4}$fluoroalkyl, $C_{1-4}$alkyl, $C_{1-4}$fluoroalkoxy and $C_{1-4}$alkoxy.

14. The compound of claim 1 selected from:

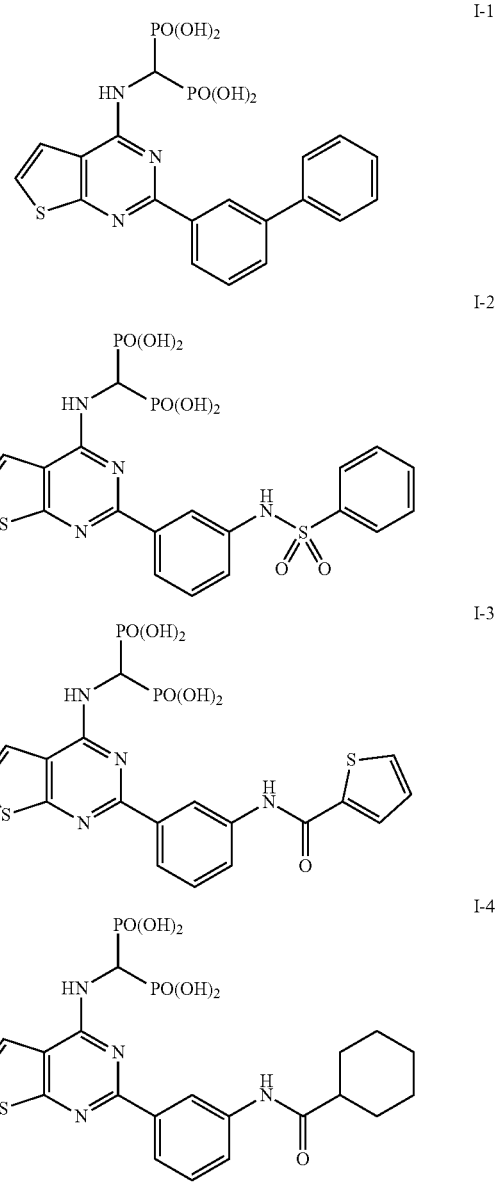

I-5
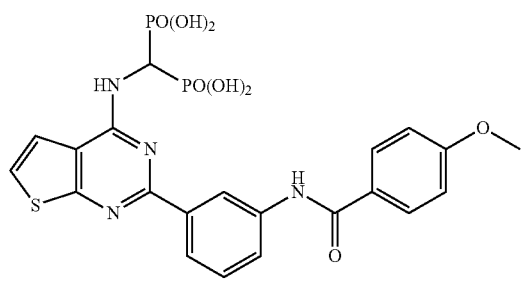
I-6
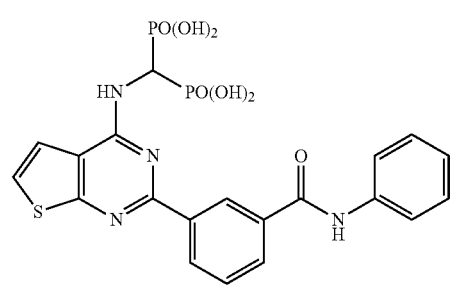
I-7
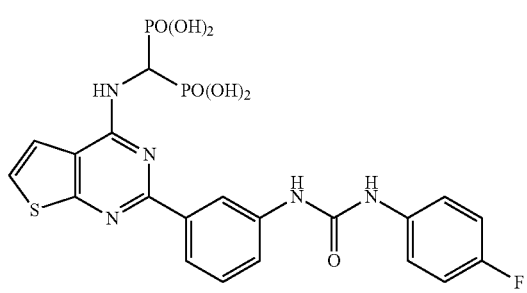
I-8
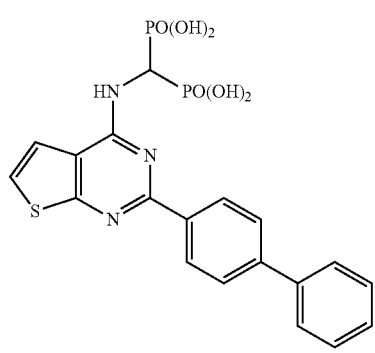
I-9
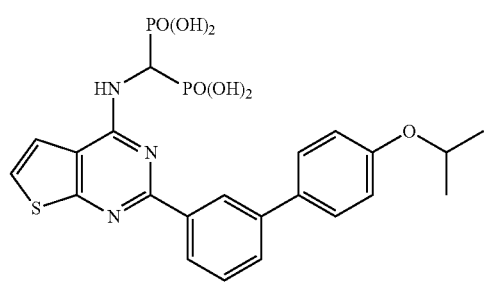
I-10
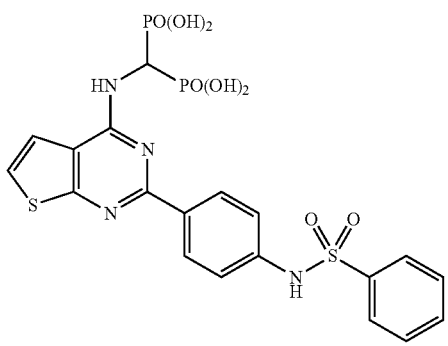
I-11
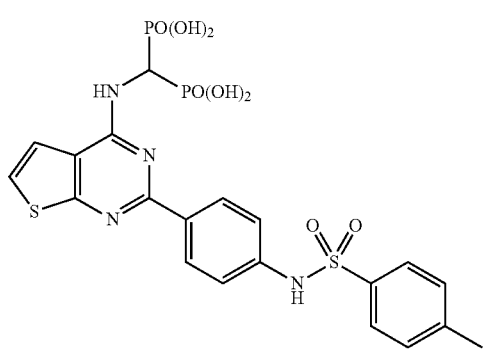
I-12
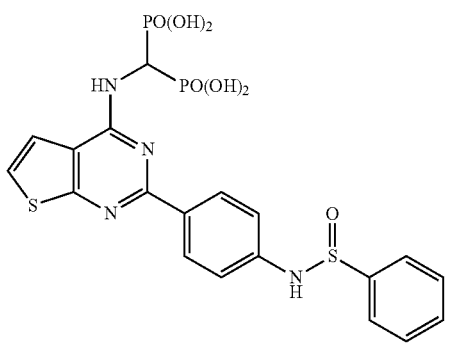
I-13
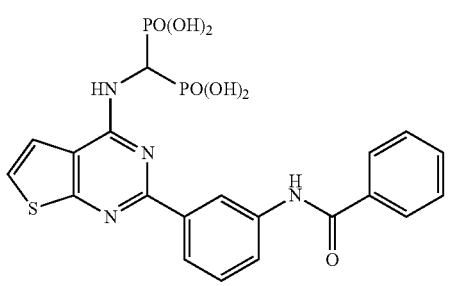
I-14
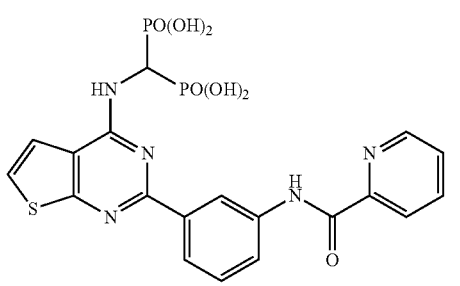

I-15
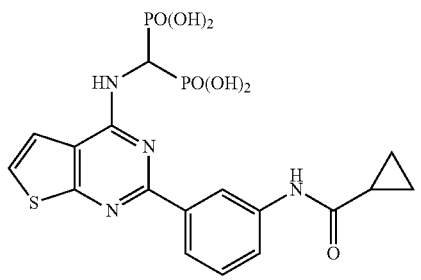
I-16
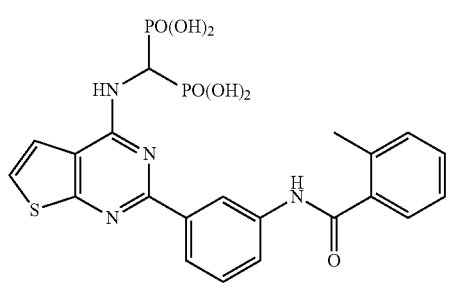
I-17
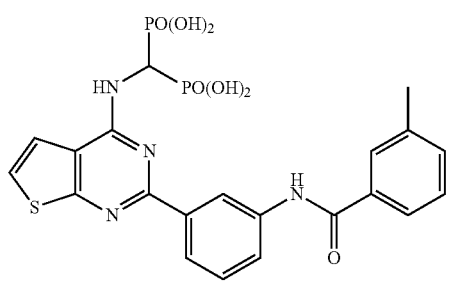
I-18
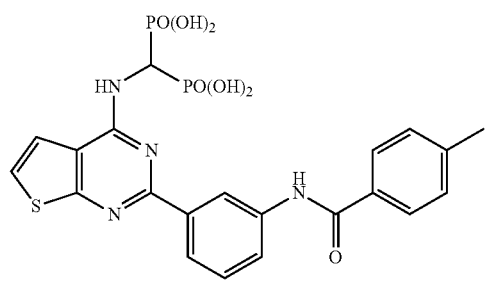
I-19
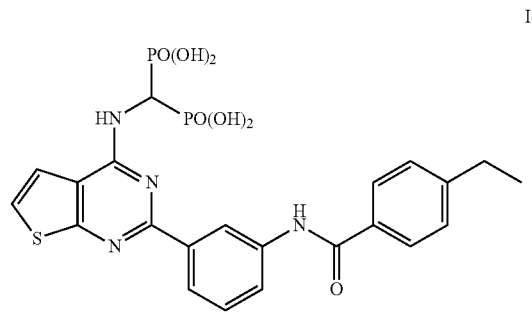
I-20
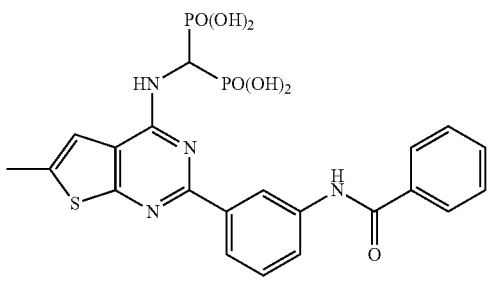
I-21
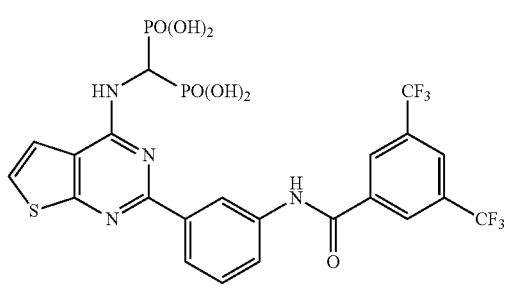
I-22
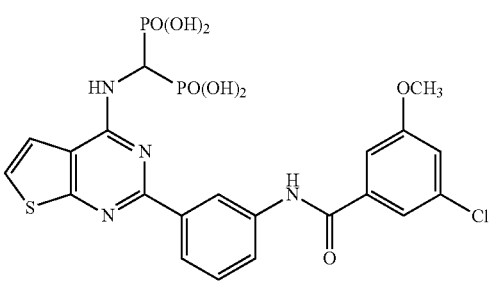
I-23
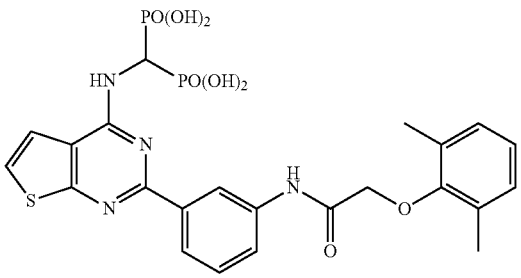
I-24
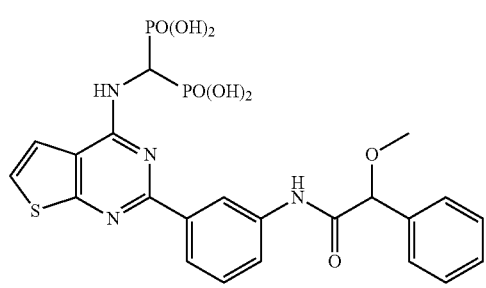

-continued
I-25
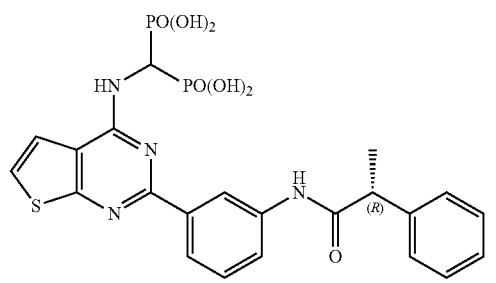
I-26
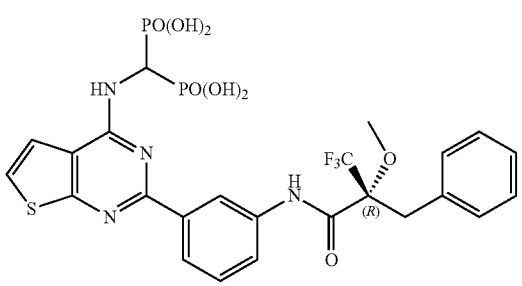
I-27
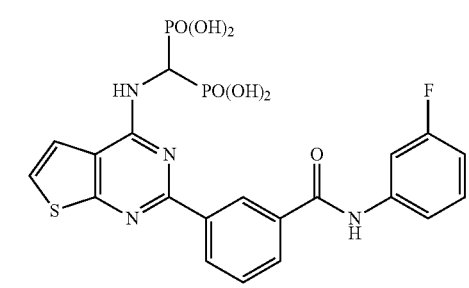
I-28
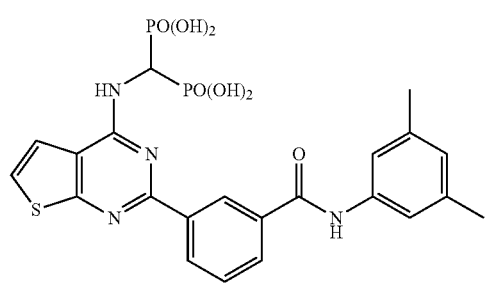
I-29
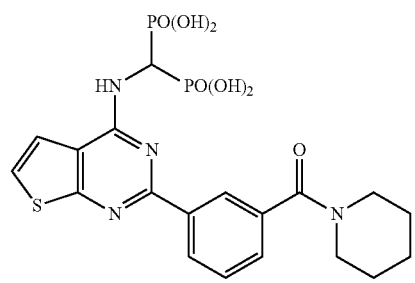
-continued
I-30
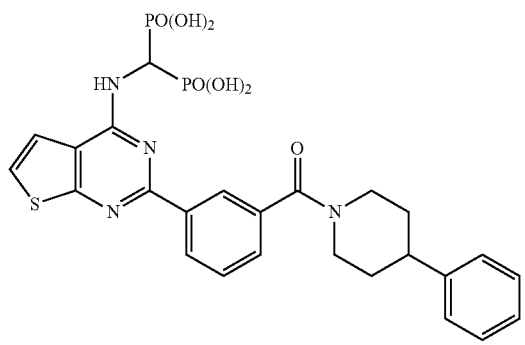
I-31
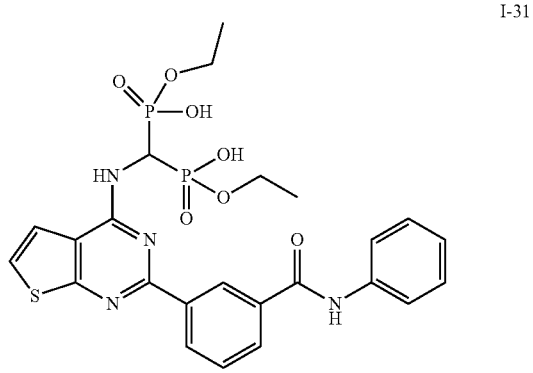
I-32
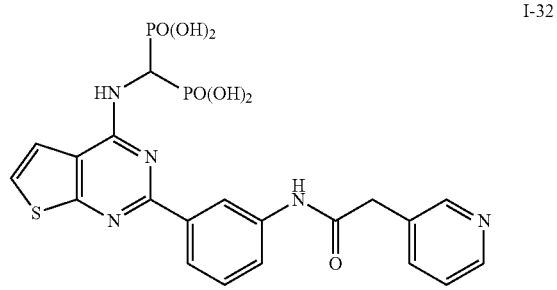
I-33
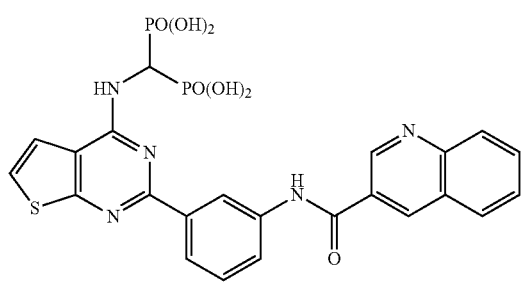
I-34
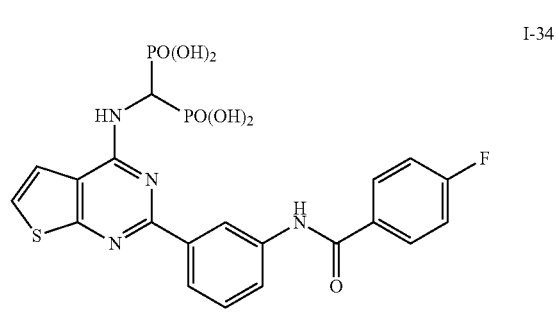

I-35
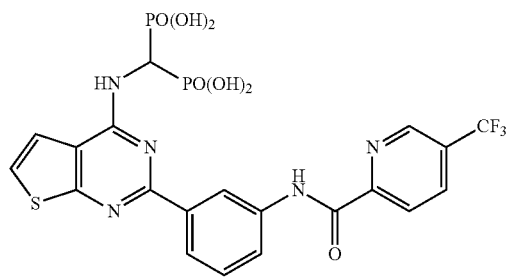
I-36
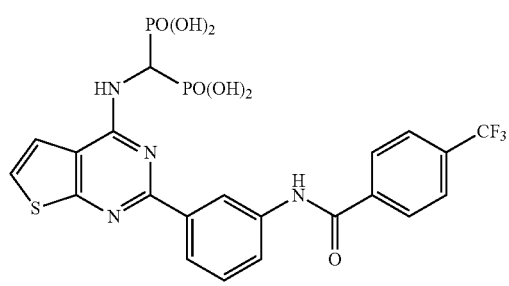
I-37
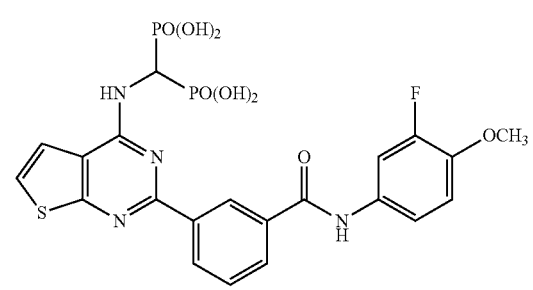
I-38
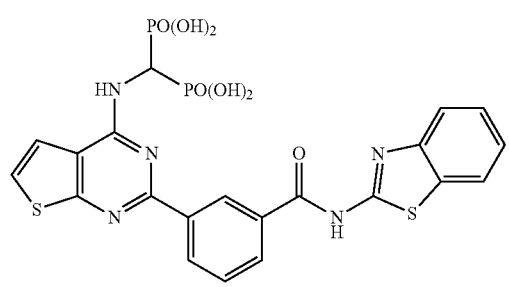
I-39
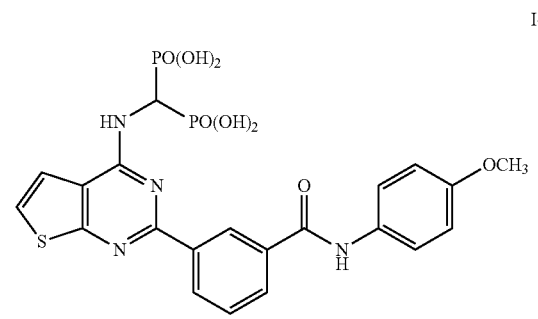
I-40
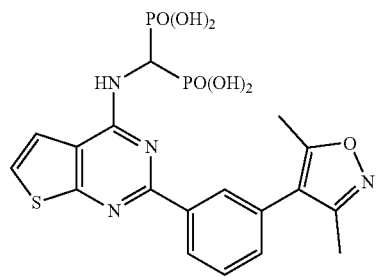
I-41
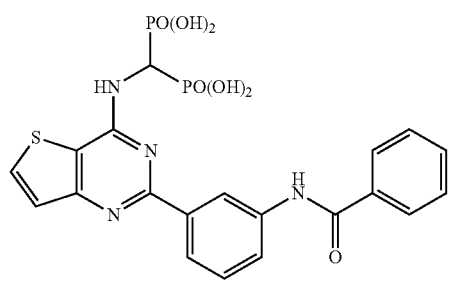
I-42
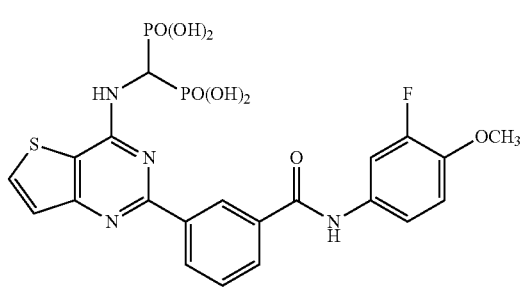
I-43
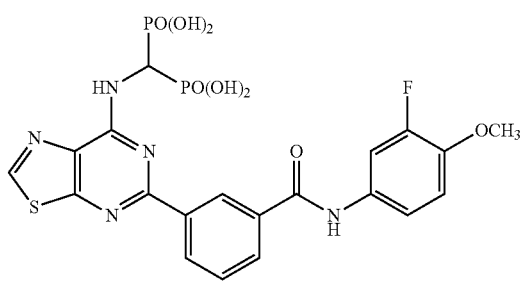
I-44
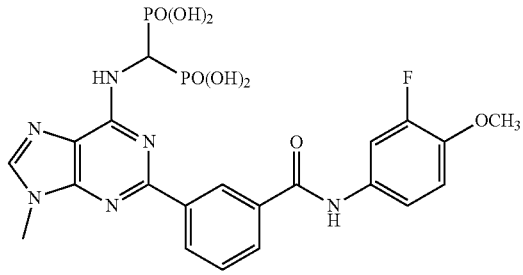

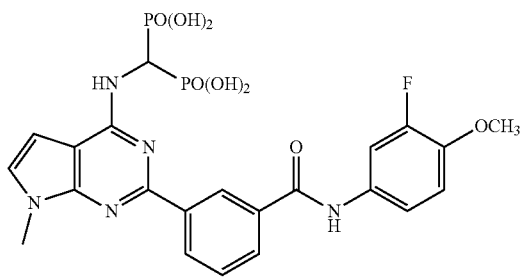

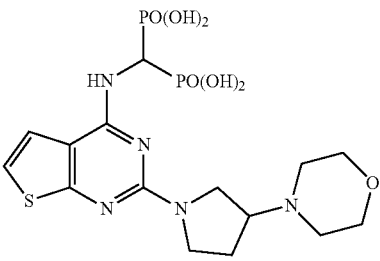

or pharmaceutically acceptable salts, solvates and prodrugs thereof.

15. A pharmaceutical composition comprising one or more compounds claim 1 and a pharmaceutically acceptable carrier.

16. A method of treating a disease, disorder or condition mediated by hGGPPS, or treatable by inhibiting geranylgeranylation of proteins, comprising administering a therapeutically effective amount of one or more compounds claim 1 to a subject in need thereof, wherein the disease, disorder or condition mediated by hGGPPS, or treatable by inhibiting geranylgeranylation, is cancer, Alzheimer's Disease or osteoporosis.

17. The method claim 16, wherein the disease, disorder or condition mediated by hGGPPS, or treatable by inhibiting geranylgeranylation, is cancer.

18. The method of claim 17, wherein the cancer is a hematological cancer or a solid tumor cancer.

19. The method of claim 17, wherein the cancer is multiple myeloma, chronic myelogenous leukemia, acute monocytic leukemia, ovarian cancer, pancreatic cancer, fibrosarcoma, colorectal cancer, brain cancer or non-small cell lung cancer.

* * * * *